US012064460B2

(12) United States Patent
Itoh et al.

(10) Patent No.: US 12,064,460 B2
(45) Date of Patent: Aug. 20, 2024

(54) ADENO-ASSOCIATED VIRUS VIRION FOR TREATMENT OF TAY-SACHS DISEASE AND SANDHOFF DISEASE

(71) Applicants: TOKUSHIMA UNIVERSITY, Tokushima (JP); JICHI MEDICAL UNIVERSITY, Tokyo (JP); GENE THERAPY RESEARCH INSTITUTION CO., LTD., Kanagawa (JP)

(72) Inventors: Kohji Itoh, Tokushima (JP); Daisuke Tsuji, Tokushima (JP); Shinichi Muramatsu, Tochigi (JP); Katsuhito Asai, Kanagawa (JP)

(73) Assignees: TOKUSHIMA UNIVERSITY, Tokushima (JP); JICHI MEDICAL UNIVERSITY, Tokyo (JP); GENE THERAPY RESEARCH INSTITUTION CO., LTD., Kanagawa (JP)

( * ) Notice: Subject to any disclaimer, the term of this patent is extended or adjusted under 35 U.S.C. 154(b) by 991 days.

(21) Appl. No.: 16/964,142

(22) PCT Filed: Jan. 25, 2019

(86) PCT No.: PCT/JP2019/002428
§ 371 (c)(1),
(2) Date: Jul. 22, 2020

(87) PCT Pub. No.: WO2019/146745
PCT Pub. Date: Aug. 1, 2019

(65) Prior Publication Data

US 2021/0030823 A1 Feb. 4, 2021

(30) Foreign Application Priority Data

Jan. 26, 2018 (JP) ................................ 2018-011705

(51) Int. Cl.
*A61K 35/76* (2015.01)
*A61P 25/28* (2006.01)
*C12N 7/00* (2006.01)

(52) U.S. Cl.
CPC .............. *A61K 35/76* (2013.01); *A61P 25/28* (2018.01); *C12N 7/00* (2013.01); *C12N 2750/14121* (2013.01); *C12N 2750/14143* (2013.01); *C12N 2750/14171* (2013.01)

(58) Field of Classification Search
CPC .. A61K 35/76; A61K 48/005; A61K 48/0075; A61P 25/28; C12N 7/00; C12N 2750/14121; C12N 2750/14143; C12N 2750/14171; C12N 9/2402; C12N 15/86; C12Y 302/01052; A01K 2217/075; A01K 2227/105; A01K 2267/0318; A01K 67/0276; C07K 2319/02
See application file for complete search history.

(56) References Cited

U.S. PATENT DOCUMENTS

| | | | | |
|---|---|---|---|---|
| 6,498,244 B1 * | 12/2002 | Patel | ...................... | A61P 43/00 435/235.1 |
| 10,400,227 B2 * | 9/2019 | Mahuran | ................ | A61K 38/47 |
| 2003/0219414 A1 | 11/2003 | Podsakoff et al. | | |
| 2005/0064539 A1 | 3/2005 | Chiba et al. | | |
| 2010/0286233 A1 | 11/2010 | Kyrkanides et al. | | |
| 2013/0224836 A1 | 8/2013 | Muramatsu | | |
| 2015/0258180 A1 * | 9/2015 | Mahuran | ................ | A61K 38/47 435/320.1 |

FOREIGN PATENT DOCUMENTS

| | | |
|---|---|---|
| EP | 2634253 A1 | 9/2013 |
| EP | 2910632 A1 | 8/2015 |
| JP | 2002-369692 A | 12/2002 |

(Continued)

OTHER PUBLICATIONS

Matsuoka K, Tamura T, Tsuji D, Dohzono Y, Kitakaze K, Ohno K, Saito S, Sakuraba H, Itoh K. Therapeutic potential of intracerebroventricular replacement of modified human β-hexosaminidase B for GM2 gangliosidosis. Mol Ther. Jun. 2011;19(6):1017-24. Epub Apr. 12, 2011. (Year: 2011).*

(Continued)

*Primary Examiner* — Rachel B Gill
(74) *Attorney, Agent, or Firm* — Crowell & Moring LLP

(57) ABSTRACT

According to a conventional method for treatment of Sandhoff disease and Tay-Sachs disease comprising administering a modified β-subunit to a patient in the form of a protein, it is necessary that administration be performed frequently. This invention relates to a recombinant adeno-associated virus virion comprising: capsomere comprising a protein capable of forming a virus virion; and a polynucleotide packaged in the capsomere comprising a promoter sequence and nucleotide sequences operably linked to the promoter sequence encoding a first amino acid sequence derived from the amino acid sequence of the β-subunit of wild-type human β-hexosaminidase composed of amino acids 55 to 556 in the sequence as shown in SEQ ID NO: 28 by substitution of amino acids 312 to 318 with glycine, serine, glutamic acid, proline, serine, glycine, and threonine in that order and a second amino acid sequence, which is an amino acid sequence of a signal peptide linked to the N terminus of the first amino acid.

9 Claims, 32 Drawing Sheets
(8 of 32 Drawing Sheet(s) Filed in Color)
Specification includes a Sequence Listing.

(56) References Cited

FOREIGN PATENT DOCUMENTS

| | | | |
|---|---|---|---|
| JP | 2009-538279 | A | 11/2009 |
| JP | 2015-523998 | A | 8/2015 |
| JP | 2016-526045 | A | 9/2016 |
| WO | WO 01/36603 | A2 | 5/2001 |
| WO | WO2010/082622 | A | 7/2010 |
| WO | WO2012/057363 | A1 | 5/2012 |
| WO | WO2013/192317 | A2 | 12/2013 |
| WO | WO2014/061735 | A1 | 4/2014 |
| WO | WO2014/194132 | A1 | 12/2014 |

OTHER PUBLICATIONS

Gray-Edwards HL, Brunson BL, Holland M, Hespel AM, Bradbury AM, McCurdy VJ, Beadlescomb PM, Randle AN, Salibi N, et. al. Mucopolysaccharidosis-like phenotype in feline Sandhoff disease and partial correction after AAV gene therapy. Mol Genet Metab. Sep.-Oct. 2015;116(1-2):80-7. Epub May 8, 2015. (Year: 2015).*

Kitakaze K, Tasaki C, Tajima Y, Hirokawa T, Tsuji D, Sakuraba H, Itoh K. Combined replacement effects of human modified β-hexosaminidase B and GM2 activator protein on GM2 gangliosidoses fibroblasts. Biochem Biophys Rep. Jun. 8, 2016;7:157-163. (Year: 2016).*

Dastsooz H, Alipour M, Mohammadi S, Kamgarpour F, Dehghanian F, Fardaei M. Identification of mutations in HEXA and HEXB in Sandhoff and Tay-Sachs diseases: a new large deletion caused by Alu elements in HEXA. Hum Genome Var. Mar. 15, 2018;5:18003. (Year: 2018).*

Mansouri-Movahed F, Akhoundi F, Nikpour P, Garshasbi M, Emadi-Baygi M. Identification of a novel HEXB Mutation in an Iranian Family with suspected patient to GM2-gangliosidoses. Clin Case Rep. Aug. 11, 2020;8(12):2583-2591. (Year: 2020).*

Zampieri S, Cattarossi S, Oller Ramirez AM, Rosano C, Lourenco CM, Passon N, Moroni I, Uziel G, et. al. Sequence and copy number analyses of HEXB gene in patients affected by Sandhoff disease: functional characterization of 9 novel sequence variants. PLoS One. 2012;7(7):e41516. Epub Jul. 27, 2012. (Year: 2012).*

Hoffmann MD, Zdechlik AC, He Y, Nedrud D, Aslanidi G, Gordon W, Schmidt D. Multiparametric domain insertional profiling of Adeno-Associated Virus VP1. bioRxiv [Preprint]. Apr. 21, 2023:2023. (Year: 2023).*

Rabinowitz JE, Xiao W, Samulski RJ. Insertional mutagenesis of AAV2 capsid and the production of recombinant virus. Virology. Dec. 20, 1999;265(2):274-85. (Year: 1999).*

Li C, Samulski RJ. Engineering adeno-associated virus vectors for gene therapy. Nat Rev Genet. Apr. 2020;21(4):255-272. doi: 10.1038/s41576-019-0205-4. Epub Feb. 10, 2020. (Year: 2020).*

Grieger JC, Johnson JS, Gurda-Whitaker B, et. al. Surface-exposed adeno-associated virus Vp1-NLS capsid fusion protein rescues infectivity of noninfectious wild-type Vp2/Vp3 and Vp3-only capsids but not that of fivefold pore mutant virions. J Virol. Aug. 2007;81(15):7833-43. Epub May 16, 2007. (Year: 2007).*

Johnson JS, Li C, DiPrimio N, Weinberg MS, McCown TJ, Samulski RJ. Mutagenesis of adeno-associated virus type 2 capsid protein VP1 uncovers new roles for basic amino acids in trafficking and cell-specific transduction. J Virol. Sep. 2010;84(17):8888-902. Epub Jun. 23, 2010. (Year: 2010).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Sela-Culang I, Kunik V, Ofran Y. The structural basis of antibody-antigen recognition. Front Immunol. Oct. 8, 2013;4:302. (Year: 2013).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Batchu RB, Gruzdyn OV, Kung ST, Weaver DW, Gruber SA. Novel AAV-DJ Capsid Tyrosine Mutants with Enhanced Transgene Expression in a Pancreatic Cancer Cell Line. J Surg Res, vol. 186, Iss. 2, 2014, pp. 637-638. (Year: 2014).*

Office Action/Search Report in Japan Application No. 2019-567181, dated Oct. 26, 2021, 5 pages.

Hioki et al., "Efficient gene transuction of neurons by lentivirus with enhanced neuron-specific promoters," Gene Therapy, 2007, vol. 14, pp. 872-882, 11 pages.

Extended European Search Report in Europe Application No. 19744605.7, dated Oct. 18, 2021, 9 pages.

Tsuji et al., "Highly Phosphomannosylated Enzyme Replacement Therapy for GM2 Gangliosidosis", Ann. Neurol., Apr. 2011, vol. 69, No. 4, pp. 691-701.

Matsuoka et al., "Therapeutic Potential of Intracerebroventricular Replacement of Modified Human β-Hexosaminidase B for GM2 Gangliosidosis", Mol. Ther., Jun. 2011, vol. 19, No. 6, pp. 1017-1024.

Tsuji, "GeneTherapy by Intracerebral AAV Injection for Inborn Errors of Metabolism", Farumashia, including English machine translation, 2007, vol. 43, No. 6, pp. 571-572.

Andersson, et al., "Sequencing, Expression, and Enzymatic Characterization of β-Hexosaminidase in Rabbit Lacrimal Gland and Primary Cultured Acinar Cells", Glycobiology, 2005, vol. 15, pp. 211-220.

International Search Report and Written Opinion, including English translation of Search Report, for Application No. PCT/JP2019/002428, dated Apr. 16, 2019, 11 pages.

* cited by examiner

| | Brain | Cerebellum | Brain stem | Heart | Lung | Liver | Spleen | Kidney |
|---|---|---|---|---|---|---|---|---|
| □WT | 966 | 370 | 563 | 158 | 385 | 182 | 1255 | 595 |
| ▨AAV(1week) | 2693 | 129 | 566 | 3400 | 253 | 755 | 555 | 134 |
| ■AAV(5weeks) | 20848 | 1295 | 16559 | 62521 | 5423 | 46870 | 26685 | 27560 |

| | Brain | Cerebellum | Brain stem | Heart | Lung | Liver | Spleen | Kidney |
|---|---|---|---|---|---|---|---|---|
| WT | 966 | 370 | 563 | 158 | 385 | 151 | 1255 | 595 |
| SD | 44 | 20 | 35 | 14 | 14 | 11 | 30 | 18 |
| AAV(5.75×10^9vg) | 1653 | 265 | 1321 | 22 | 106 | 60 | 51 | 67 |
| AAV(5.75×10^11vg) | 20848 | 1295 | 16559 | 62521 | 5423 | 46870 | 26685 | 27560 |

| | Brain | Cerebellum | Brain stem | Heart | Lung | Liver | Spleen | Kidney |
|---|---|---|---|---|---|---|---|---|
| WT | 966 | 370 | 563 | 158 | 385 | 151 | 1255 | 595 |
| SD | 44 | 20 | 35 | 14 | 14 | 11 | 30 | 18 |
| Het (P1 AAV intraventricular administration) | 24661 | 23040 | 32008 | 77063 | 3204 | 5113 | 2331 | 1399 |
| Het (P0 AAV intravenous administration) | 8475 | 21076 | 18450 | 304645 | 26464 | 10644 | 6265 | 8101 |

WT 16wks(n=3)
SD 16wks(n=4)
Hetero 10-week-old AAV $1.15 \times 10^{11}$ vg/mouse administration 17-week-old (n=2)

Fig. 13B

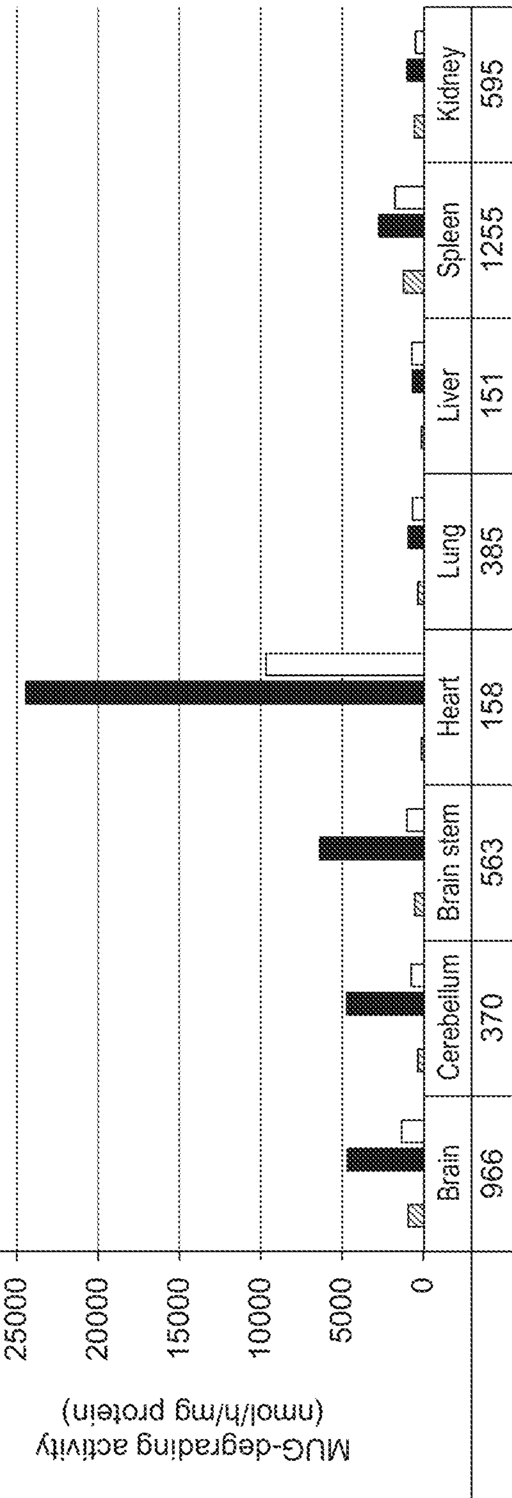

| | Brain | Cerebellum | Brain stem | Heart | Lung | Liver | Spleen | Kidney |
|---|---|---|---|---|---|---|---|---|
| WT | 966 | 370 | 563 | 158 | 385 | 151 | 1255 | 595 |
| SD | 44 | 20 | 35 | 14 | 14 | 11 | 30 | 18 |
| Het (P0 AAV intraventricular administration) | 4704 | 4713 | 6394 | 24456 | 936 | 680 | 2772 | 1012 |
| Het (P0 AAV intravenous administration) | 1344 | 765 | 1012 | 9680 | 684 | 709 | 1768 | 510 |

WT SD Het (P0 AAV intraventricular administration) Het (P0 AAV intravenous administration)

WT 16wks(n=3)
SD 16wks(n=4)
Hetero 10-week-old AAV 1.15 x $10^{11}$ vg/mouse single intraventricular administration 17-week-old (n=2)
Hetero 10-week-old AAV 1.15 x $10^{11}$ vg/mouse single intravenous administration 17-week-old (n=2)

β-Tubulin III···neuron marker, TBR1···cerebral cortex neuron marker, A2B5···glial progenitor cell marker, GFAP···astrocyte marker Anti-NAG(A)

Western blotting

- 10μg protein/lane
- 10% SDS-PAGEgel
- Detection reagent: ECL plus
- Detection sensitivity: standard
- Detection time: 8 sec

SEQUENCE LISTING

```
<160> NUMBER OF SEQ ID NOS: 29

<210> SEQ ID NO 1
<211> LENGTH: 2208
<212> TYPE: DNA
```

```
<213> ORGANISM: adeno-associated virus 1
<220> FEATURE:
<221> NAME/KEY: CDS
<222> LOCATION: (1)..(2208)
<223> OTHER INFORMATION: AAV1-VP1 Capsid

<400> SEQUENCE: 1

atg gct gcc gat ggt tat ctt cca gat tgg ctc gag gac aac ctc tct       48
Met Ala Ala Asp Gly Tyr Leu Pro Asp Trp Leu Glu Asp Asn Leu Ser
1               5                   10                  15

gag ggc att cgc gag tgg tgg gac ttg aaa cct gga gcc ccg aag ccc       96
Glu Gly Ile Arg Glu Trp Trp Asp Leu Lys Pro Gly Ala Pro Lys Pro
            20                  25                  30

aaa gcc aac cag caa aag cag gac gac ggc cgg ggt ctg gtg ctt cct      144
Lys Ala Asn Gln Gln Lys Gln Asp Asp Gly Arg Gly Leu Val Leu Pro
        35                  40                  45

ggc tac aag tac ctc gga ccc ttc aac gga ctc gac aag ggg gag ccc      192
Gly Tyr Lys Tyr Leu Gly Pro Phe Asn Gly Leu Asp Lys Gly Glu Pro
    50                  55                  60

gtc aac gcg gcg gac gca gcg gcc ctc gag cac gac aag gcc tac gac      240
Val Asn Ala Ala Asp Ala Ala Ala Leu Glu His Asp Lys Ala Tyr Asp
65                  70                  75                  80

cag cag ctc aaa gcg ggt gac aat ccg tac ctg cgg tat aac cac gcc      288
Gln Gln Leu Lys Ala Gly Asp Asn Pro Tyr Leu Arg Tyr Asn His Ala
                85                  90                  95

gac gcc gag ttt cag gag cgt ctg caa gaa gat acg tct ttt ggg ggc      336
Asp Ala Glu Phe Gln Glu Arg Leu Gln Glu Asp Thr Ser Phe Gly Gly
            100                 105                 110

aac ctc ggg cga gca gtc ttc cag gcc aag aag cgg gtt ctc gaa cct      384
Asn Leu Gly Arg Ala Val Phe Gln Ala Lys Lys Arg Val Leu Glu Pro
        115                 120                 125

ctc ggt ctg gtt gag gaa ggc gct aag acg gct cct gga aag aaa cgt      432
Leu Gly Leu Val Glu Glu Gly Ala Lys Thr Ala Pro Gly Lys Lys Arg
    130                 135                 140

ccg gta gag cag tcg cca caa gag cca gac tcc tcc tcg ggc atc ggc      480
Pro Val Glu Gln Ser Pro Gln Glu Pro Asp Ser Ser Ser Gly Ile Gly
145                 150                 155                 160

aag aca ggc cag cag ccc gct aaa aag aga ctc aat ttt ggt cag act      528
Lys Thr Gly Gln Gln Pro Ala Lys Lys Arg Leu Asn Phe Gly Gln Thr
                165                 170                 175

ggc gac tca gag tca gtc ccc gat cca caa cct ctc gga gaa cct cca      576
Gly Asp Ser Glu Ser Val Pro Asp Pro Gln Pro Leu Gly Glu Pro Pro
            180                 185                 190

gca acc ccc gct gct gtg gga cct act aca atg gct tca ggc ggt ggc      624
Ala Thr Pro Ala Ala Val Gly Pro Thr Thr Met Ala Ser Gly Gly Gly
        195                 200                 205

gca cca atg gca gac aat aac gaa ggc gcc gac gga gtg ggt aat gcc      672
Ala Pro Met Ala Asp Asn Asn Glu Gly Ala Asp Gly Val Gly Asn Ala
    210                 215                 220

tca gga aat tgg cat tgc gat tcc aca tgg ctg ggc gac aga gtc atc      720
Ser Gly Asn Trp His Cys Asp Ser Thr Trp Leu Gly Asp Arg Val Ile
225                 230                 235                 240

acc acc agc acc cgc acc tgg gcc ttg ccc acc tac aat aac cac ctc      768
Thr Thr Ser Thr Arg Thr Trp Ala Leu Pro Thr Tyr Asn Asn His Leu
                245                 250                 255

tac aag caa atc tcc agt gct tca acg ggg gcc agc aac gac aac cac      816
Tyr Lys Gln Ile Ser Ser Ala Ser Thr Gly Ala Ser Asn Asp Asn His
            260                 265                 270

tac ttc ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
        275                 280                 285
```

-continued

```
cac tgc cac ttt tca cca cgt gac tgg cag cga ctc atc aac aac aat      912
His Cys His Phe Ser Pro Arg Asp Trp Gln Arg Leu Ile Asn Asn Asn
    290                 295                 300

tgg gga ttc cgg ccc aag aga ctc aac ttc aaa ctc ttc aac atc caa      960
Trp Gly Phe Arg Pro Lys Arg Leu Asn Phe Lys Leu Phe Asn Ile Gln
305                 310                 315                 320

gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335

ctt acc agc acg gtt caa gtc ttc tcg gac tcg gag tac cag ctt ccg     1056
Leu Thr Ser Thr Val Gln Val Phe Ser Asp Ser Glu Tyr Gln Leu Pro
            340                 345                 350

tac gtc ctc ggc tct gcg cac cag ggc tgc ctc cct ccg ttc ccg gcg     1104
Tyr Val Leu Gly Ser Ala His Gln Gly Cys Leu Pro Pro Phe Pro Ala
        355                 360                 365

gac gtg ttc atg att ccg caa tac ggc tac ctg acg ctc aac aat ggc     1152
Asp Val Phe Met Ile Pro Gln Tyr Gly Tyr Leu Thr Leu Asn Asn Gly
    370                 375                 380

agc caa gcc gtg gga cgt tca tcc ttt tac tgc ctg gaa tat ttc cct     1200
Ser Gln Ala Val Gly Arg Ser Ser Phe Tyr Cys Leu Glu Tyr Phe Pro
385                 390                 395                 400

tct cag atg ctg aga acg ggc aac aac ttt acc ttc agc tac acc ttt     1248
Ser Gln Met Leu Arg Thr Gly Asn Asn Phe Thr Phe Ser Tyr Thr Phe
                405                 410                 415

gag gaa gtg cct ttc cac agc agc tac gcg cac agc cag agc ctg gac     1296
Glu Glu Val Pro Phe His Ser Ser Tyr Ala His Ser Gln Ser Leu Asp
            420                 425                 430

cgg ctg atg aat cct ctc atc gac caa tac ctg tat tac ctg aac aga     1344
Arg Leu Met Asn Pro Leu Ile Asp Gln Tyr Leu Tyr Tyr Leu Asn Arg
        435                 440                 445

act caa aat cag tcc gga agt gcc caa aac aag gac ttg ctg ttt agc     1392
Thr Gln Asn Gln Ser Gly Ser Ala Gln Asn Lys Asp Leu Leu Phe Ser
    450                 455                 460

cgt ggg tct cca gct ggc atg tct gtt cag ccc aaa aac tgg cta cct     1440
Arg Gly Ser Pro Ala Gly Met Ser Val Gln Pro Lys Asn Trp Leu Pro
465                 470                 475                 480

gga ccc tgt tat cgg cag cag cgc gtt tct aaa aca aaa aca gac aac     1488
Gly Pro Cys Tyr Arg Gln Gln Arg Val Ser Lys Thr Lys Thr Asp Asn
                485                 490                 495

aac aac agc aat ttt acc tgg act ggt gct tca aaa tat aac ctc aat     1536
Asn Asn Ser Asn Phe Thr Trp Thr Gly Ala Ser Lys Tyr Asn Leu Asn
            500                 505                 510

ggg cgt gaa tcc atc atc aac cct ggc act gct atg gcc tca cac aaa     1584
Gly Arg Glu Ser Ile Ile Asn Pro Gly Thr Ala Met Ala Ser His Lys
        515                 520                 525

gac gac gaa gac aag ttc ttt ccc atg agc ggt gtc atg att ttt gga     1632
Asp Asp Glu Asp Lys Phe Phe Pro Met Ser Gly Val Met Ile Phe Gly
    530                 535                 540

aaa gag agc gcc gga gct tca aac act gca ttg gac aat gtc atg att     1680
Lys Glu Ser Ala Gly Ala Ser Asn Thr Ala Leu Asp Asn Val Met Ile
545                 550                 555                 560

aca gac gaa gag gaa att aaa gcc act aac cct gtg gcc acc gaa aga     1728
Thr Asp Glu Glu Glu Ile Lys Ala Thr Asn Pro Val Ala Thr Glu Arg
                565                 570                 575

ttt ggg acc gtg gca gtc aat ttc cag agc agc agc aca gac cct gcg     1776
Phe Gly Thr Val Ala Val Asn Phe Gln Ser Ser Ser Thr Asp Pro Ala
            580                 585                 590

acc gga gat gtg cat gct atg gga gca tta cct ggc atg gtg tgg caa     1824
Thr Gly Asp Val His Ala Met Gly Ala Leu Pro Gly Met Val Trp Gln
```

-continued

```
        595                 600                 605

gat aga gac gtg tac ctg cag ggt ccc att tgg gcc aaa att cct cac      1872
Asp Arg Asp Val Tyr Leu Gln Gly Pro Ile Trp Ala Lys Ile Pro His
    610                 615                 620

aca gat gga cac ttt cac ccg tct cct ctt atg ggc ggc ttt gga ctc      1920
Thr Asp Gly His Phe His Pro Ser Pro Leu Met Gly Gly Phe Gly Leu
625                 630                 635                 640

aag aac ccg cct cct cag atc ctc atc aaa aac acg cct gtt cct gcg      1968
Lys Asn Pro Pro Pro Gln Ile Leu Ile Lys Asn Thr Pro Val Pro Ala
                645                 650                 655

aat cct ccg gcg gag ttt tca gct aca aag ttt gct tca ttc atc acc      2016
Asn Pro Pro Ala Glu Phe Ser Ala Thr Lys Phe Ala Ser Phe Ile Thr
            660                 665                 670

caa tac tcc aca gga caa gtg agt gtg gaa att gaa tgg gag ctg cag      2064
Gln Tyr Ser Thr Gly Gln Val Ser Val Glu Ile Glu Trp Glu Leu Gln
        675                 680                 685

aaa gaa aac agc aag cgc tgg aat ccc gaa gtg cag tac aca tcc aat      2112
Lys Glu Asn Ser Lys Arg Trp Asn Pro Glu Val Gln Tyr Thr Ser Asn
    690                 695                 700

tat gca aaa tct gcc aac gtt gat ttt act gtg gac aac aat gga ctt      2160
Tyr Ala Lys Ser Ala Asn Val Asp Phe Thr Val Asp Asn Asn Gly Leu
705                 710                 715                 720

tat act gag cct cgc ccc att ggc acc cgt tac ctt acc cgt ccc ctg      2208
Tyr Thr Glu Pro Arg Pro Ile Gly Thr Arg Tyr Leu Thr Arg Pro Leu
                725                 730                 735


<210> SEQ ID NO 2
<211> LENGTH: 736
<212> TYPE: PRT
<213> ORGANISM: adeno-associated virus 1

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
```

-continued

```
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620
```

```
Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 3
<211> LENGTH: 2205
<212> TYPE: DNA
<213> ORGANISM: adeno-associated virus 2
<220> FEATURE:
<221> NAME/KEY: CDS
<222> LOCATION: (1)..(2205)
<223> OTHER INFORMATION: AAV2-VP1 Capsid

<400> SEQUENCE: 3

atg gct gcc gat ggt tat ctt cca gat tgg ctc gag gac act ctc tct       48
Met Ala Ala Asp Gly Tyr Leu Pro Asp Trp Leu Glu Asp Thr Leu Ser
1               5                   10                  15

gaa gga ata aga cag tgg tgg aag ctc aaa cct ggc cca cca cca cca       96
Glu Gly Ile Arg Gln Trp Trp Lys Leu Lys Pro Gly Pro Pro Pro Pro
            20                  25                  30

aag ccc gca gag cgg cat aag gac gac agc agg ggt ctt gtg ctt cct      144
Lys Pro Ala Glu Arg His Lys Asp Asp Ser Arg Gly Leu Val Leu Pro
        35                  40                  45

ggg tac aag tac ctc gga ccc ttc aac gga ctc gac aag gga gag ccg      192
Gly Tyr Lys Tyr Leu Gly Pro Phe Asn Gly Leu Asp Lys Gly Glu Pro
    50                  55                  60

gtc aac gag gca gac gcc gcg gcc ctc gag cac gac aaa gcc tac gac      240
Val Asn Glu Ala Asp Ala Ala Ala Leu Glu His Asp Lys Ala Tyr Asp
65                  70                  75                  80

cgg cag ctc gac agc gga gac aac ccg tac ctc aag tac aac cac gcc      288
Arg Gln Leu Asp Ser Gly Asp Asn Pro Tyr Leu Lys Tyr Asn His Ala
                85                  90                  95

gac gcg gag ttt cag gag cgc ctt aaa gaa gat acg tct ttt ggg ggc      336
Asp Ala Glu Phe Gln Glu Arg Leu Lys Glu Asp Thr Ser Phe Gly Gly
            100                 105                 110

aac ctc gga cga gca gtc ttc cag gcg aaa aag agg gtt ctt gaa cct      384
Asn Leu Gly Arg Ala Val Phe Gln Ala Lys Lys Arg Val Leu Glu Pro
        115                 120                 125

ctg ggc ctg gtt gag gaa cct gtt aag acg gct ccg gga aaa aag agg      432
Leu Gly Leu Val Glu Glu Pro Val Lys Thr Ala Pro Gly Lys Lys Arg
    130                 135                 140

ccg gta gag cac tct cct gtg gag cca gac tcc tcc tcg gga acc gga      480
Pro Val Glu His Ser Pro Val Glu Pro Asp Ser Ser Ser Gly Thr Gly
145                 150                 155                 160

aag gcg ggc cag cag cct gca aga aaa aga ttg aat ttt ggt cag act      528
Lys Ala Gly Gln Gln Pro Ala Arg Lys Arg Leu Asn Phe Gly Gln Thr
                165                 170                 175

gga gac gca gac tca gta cct gac ccc cag cct ctc gga cag cca cca      576
```

-continued

```
Gly Asp Ala Asp Ser Val Pro Asp Pro Gln Pro Leu Gly Gln Pro Pro
            180                 185                 190

gca gcc ccc tct ggt ctg gga act aat acg atg gct aca ggc agt ggc      624
Ala Ala Pro Ser Gly Leu Gly Thr Asn Thr Met Ala Thr Gly Ser Gly
        195                 200                 205

gca cca atg gca gac aat aac gag ggc gcc gac gga gtg ggt aat tcc      672
Ala Pro Met Ala Asp Asn Asn Glu Gly Ala Asp Gly Val Gly Asn Ser
    210                 215                 220

tcg gga aat tgg cat tgc gat tcc aca tgg atg ggc gac aga gtc atc      720
Ser Gly Asn Trp His Cys Asp Ser Thr Trp Met Gly Asp Arg Val Ile
225                 230                 235                 240

acc acc agc acc cga acc tgg gcc ctg ccc acc tac aac aac cac ctc      768
Thr Thr Ser Thr Arg Thr Trp Ala Leu Pro Thr Tyr Asn Asn His Leu
                245                 250                 255

tac aaa caa att tcc agc caa tca gga gcc tcg aac gac aat cac tac      816
Tyr Lys Gln Ile Ser Ser Gln Ser Gly Ala Ser Asn Asp Asn His Tyr
            260                 265                 270

ttt ggc tac agc acc cct tgg ggg tat ttt gac ttc aac aga ttc cac      864
Phe Gly Tyr Ser Thr Pro Trp Gly Tyr Phe Asp Phe Asn Arg Phe His
        275                 280                 285

tgc cac ttt tca cca cgt gac tgg caa aga ctc atc aac aac aac tgg      912
Cys His Phe Ser Pro Arg Asp Trp Gln Arg Leu Ile Asn Asn Asn Trp
    290                 295                 300

gga ttc cga ccc aag aga ctc aac ttc aag ctc ttt aac att caa gtc      960
Gly Phe Arg Pro Lys Arg Leu Asn Phe Lys Leu Phe Asn Ile Gln Val
305                 310                 315                 320

aaa gag gtc acg cag aat gac ggt acg acg acg att gcc aat aac ctt     1008
Lys Glu Val Thr Gln Asn Asp Gly Thr Thr Thr Ile Ala Asn Asn Leu
                325                 330                 335

acc agc acg gtt cag gtg ttt act gac tcg gag tac cag ctc ccg tac     1056
Thr Ser Thr Val Gln Val Phe Thr Asp Ser Glu Tyr Gln Leu Pro Tyr
            340                 345                 350

gtc ctc ggc tcg gcg cat caa gga tgc ctc ccg ccg ttc cca gca gac     1104
Val Leu Gly Ser Ala His Gln Gly Cys Leu Pro Pro Phe Pro Ala Asp
        355                 360                 365

gtc ttc atg gtg cca cag tat gga tac ctc acc ctg aac aac ggg agt     1152
Val Phe Met Val Pro Gln Tyr Gly Tyr Leu Thr Leu Asn Asn Gly Ser
    370                 375                 380

cag gca gta gga cgc tct tca ttt tac tgc ctg gag tac ttt cct tct     1200
Gln Ala Val Gly Arg Ser Ser Phe Tyr Cys Leu Glu Tyr Phe Pro Ser
385                 390                 395                 400

cag atg ctg cgt acc gga aac aac ttt acc ttc agc tac act ttt gag     1248
Gln Met Leu Arg Thr Gly Asn Asn Phe Thr Phe Ser Tyr Thr Phe Glu
                405                 410                 415

gac gtt cct ttc cac agc agc tac gct cac agc cag agt ctg gac cgt     1296
Asp Val Pro Phe His Ser Ser Tyr Ala His Ser Gln Ser Leu Asp Arg
            420                 425                 430

ctc atg aat cct ctc atc gac cag tac ctg tat tac ttg agc aga aca     1344
Leu Met Asn Pro Leu Ile Asp Gln Tyr Leu Tyr Tyr Leu Ser Arg Thr
        435                 440                 445

aac act cca agt gga acc acc acg cag tca agg ctt cag ttt tct cag     1392
Asn Thr Pro Ser Gly Thr Thr Thr Gln Ser Arg Leu Gln Phe Ser Gln
    450                 455                 460

gcc gga gcg agt gac att cgg gac cag tct agg aac tgg ctt cct gga     1440
Ala Gly Ala Ser Asp Ile Arg Asp Gln Ser Arg Asn Trp Leu Pro Gly
465                 470                 475                 480

ccc tgt tac cgc cag cag cga gta tca aag aca tct gcg gat aac aac     1488
Pro Cys Tyr Arg Gln Gln Arg Val Ser Lys Thr Ser Ala Asp Asn Asn
                485                 490                 495
```

-continued

```
aac agt gaa tac tcg tgg act gga gct acc aag tac cac ctc aat ggc      1536
Asn Ser Glu Tyr Ser Trp Thr Gly Ala Thr Lys Tyr His Leu Asn Gly
            500                 505                 510

aga gac tct ctg gtg aat ccg ggc ccg gcc atg gca agc cac aag gac      1584
Arg Asp Ser Leu Val Asn Pro Gly Pro Ala Met Ala Ser His Lys Asp
        515                 520                 525

gat gaa gaa aag ttt ttt cct cag agc ggg gtt ctc atc ttt ggg aag      1632
Asp Glu Glu Lys Phe Phe Pro Gln Ser Gly Val Leu Ile Phe Gly Lys
    530                 535                 540

caa ggc tca gag aaa aca aat gtg gac att gaa aag gtc atg att aca      1680
Gln Gly Ser Glu Lys Thr Asn Val Asp Ile Glu Lys Val Met Ile Thr
545                 550                 555                 560

gac gaa gag gaa atc agg aca acc aat ccc gtg gct acg gag cag tat      1728
Asp Glu Glu Glu Ile Arg Thr Thr Asn Pro Val Ala Thr Glu Gln Tyr
                565                 570                 575

ggt tct gta tct acc aac ctc cag aga ggc aac aga caa gca gct acc      1776
Gly Ser Val Ser Thr Asn Leu Gln Arg Gly Asn Arg Gln Ala Ala Thr
            580                 585                 590

gca gat gtc aac aca caa ggc gtt ctt cca ggc atg gtc tgg cag gac      1824
Ala Asp Val Asn Thr Gln Gly Val Leu Pro Gly Met Val Trp Gln Asp
        595                 600                 605

aga gat gtg tac ctt cag ggg ccc atc tgg gca aag att cca cac acg      1872
Arg Asp Val Tyr Leu Gln Gly Pro Ile Trp Ala Lys Ile Pro His Thr
    610                 615                 620

gac gga cat ttt cac ccc tct ccc ctc atg ggt gga ttc gga ctt aaa      1920
Asp Gly His Phe His Pro Ser Pro Leu Met Gly Gly Phe Gly Leu Lys
625                 630                 635                 640

cac cct cct cca cag att ctc atc aag aac acc ccg gta cct gcg aat      1968
His Pro Pro Pro Gln Ile Leu Ile Lys Asn Thr Pro Val Pro Ala Asn
                645                 650                 655

cct tcg acc acc ttc agt gcg gca aag ttt gct tcc ttc atc aca cag      2016
Pro Ser Thr Thr Phe Ser Ala Ala Lys Phe Ala Ser Phe Ile Thr Gln
            660                 665                 670

tac tcc acg gga cag gtc agc gtg gag atc gag tgg gag ctg cag aag      2064
Tyr Ser Thr Gly Gln Val Ser Val Glu Ile Glu Trp Glu Leu Gln Lys
        675                 680                 685

gaa aac agc aaa cgc tgg aat ccc gaa att cag tac act tcc aac tac      2112
Glu Asn Ser Lys Arg Trp Asn Pro Glu Ile Gln Tyr Thr Ser Asn Tyr
    690                 695                 700

aac aag tct gtt aat gtg gac ttt act gtg gac act aat ggc gtg tat      2160
Asn Lys Ser Val Asn Val Asp Phe Thr Val Asp Thr Asn Gly Val Tyr
705                 710                 715                 720

tca gag cct cgc ccc att ggc acc aga tac ctg act cgt aat ctg          2205
Ser Glu Pro Arg Pro Ile Gly Thr Arg Tyr Leu Thr Arg Asn Leu
                725                 730                 735


<210> SEQ ID NO 4
<211> LENGTH: 735
<212> TYPE: PRT
<213> ORGANISM: adeno-associated virus 2

<400> SEQUENCE: 4

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480
```

-continued

```
Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 5
<211> LENGTH: 2208
<212> TYPE: DNA
<213> ORGANISM: adeno-associated virus 9
<220> FEATURE:
<221> NAME/KEY: CDS
<222> LOCATION: (1)..(2208)
<223> OTHER INFORMATION: AAV9-VP1 Capsid

<400> SEQUENCE: 5

atg gct gcc gat ggt tat ctt cca gat tgg ctc gag gac aac ctt agt       48
Met Ala Ala Asp Gly Tyr Leu Pro Asp Trp Leu Glu Asp Asn Leu Ser
1               5                   10                  15

gaa gga att cgc gag tgg tgg gct ttg aaa cct gga gcc cct caa ccc       96
Glu Gly Ile Arg Glu Trp Trp Ala Leu Lys Pro Gly Ala Pro Gln Pro
            20                  25                  30

aag gca aat caa caa cat caa gac aac gct cga ggt ctt gtg ctt ccg      144
Lys Ala Asn Gln Gln His Gln Asp Asn Ala Arg Gly Leu Val Leu Pro
        35                  40                  45

ggt tac aaa tac ctt gga ccc ggc aac gga ctc gac aag ggg gag ccg      192
Gly Tyr Lys Tyr Leu Gly Pro Gly Asn Gly Leu Asp Lys Gly Glu Pro
    50                  55                  60

gtc aac gca gca gac gcg gcg gcc ctc gag cac gac aag gcc tac gac      240
Val Asn Ala Ala Asp Ala Ala Ala Leu Glu His Asp Lys Ala Tyr Asp
65                  70                  75                  80
```

-continued

```
cag cag ctc aag gcc gga gac aac ccg tac ctc aag tac aac cac gcc      288
Gln Gln Leu Lys Ala Gly Asp Asn Pro Tyr Leu Lys Tyr Asn His Ala
            85                  90                  95

gac gcc gag ttc cag gag cgg ctc aaa gaa gat acg tct ttt ggg ggc      336
Asp Ala Glu Phe Gln Glu Arg Leu Lys Glu Asp Thr Ser Phe Gly Gly
        100                 105                 110

aac ctc ggg cga gca gtc ttc cag gcc aaa aag agg ctt ctt gaa cct      384
Asn Leu Gly Arg Ala Val Phe Gln Ala Lys Lys Arg Leu Leu Glu Pro
        115                 120                 125

ctt ggt ctg gtt gag gaa gcg gct aag acg gct cct gga aag aag agg      432
Leu Gly Leu Val Glu Glu Ala Ala Lys Thr Ala Pro Gly Lys Lys Arg
    130                 135                 140

cct gta gag cag tct cct cag gaa ccg gac tcc tcc gcg ggt att ggc      480
Pro Val Glu Gln Ser Pro Gln Glu Pro Asp Ser Ser Ala Gly Ile Gly
145                 150                 155                 160

aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                165                 170                 175

ggc gac aca gag tca gtc cca gac cct caa cca atc gga gaa cct ccc      576
Gly Asp Thr Glu Ser Val Pro Asp Pro Gln Pro Ile Gly Glu Pro Pro
            180                 185                 190

gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
        195                 200                 205

gca cca gtg gca gac aat aac gaa ggt gcc gat gga gtg ggt agt tcc      672
Ala Pro Val Ala Asp Asn Asn Glu Gly Ala Asp Gly Val Gly Ser Ser
    210                 215                 220

tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225                 230                 235                 240

acc acc agc acc cga acc tgg gcc ctg ccc acc tac aac aat cac ctc      768
Thr Thr Ser Thr Arg Thr Trp Ala Leu Pro Thr Tyr Asn Asn His Leu
                245                 250                 255

tac aag caa atc tcc aac agc aca tct gga gga tct tca aat gac aac      816
Tyr Lys Gln Ile Ser Asn Ser Thr Ser Gly Gly Ser Ser Asn Asp Asn
            260                 265                 270

gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
        275                 280                 285

ttc cac tgc cac ttc tca cca cgt gac tgg cag cga ctc atc aac aac      912
Phe His Cys His Phe Ser Pro Arg Asp Trp Gln Arg Leu Ile Asn Asn
    290                 295                 300

aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305                 310                 315                 320

cag gtc aaa gag gtt acg gac aac aat gga gtc aag acc atc gcc aat     1008
Gln Val Lys Glu Val Thr Asp Asn Asn Gly Val Lys Thr Ile Ala Asn
                325                 330                 335

aac ctt acc agc acg gtc cag gtc ttc acg gac tca gac tat cag ctc     1056
Asn Leu Thr Ser Thr Val Gln Val Phe Thr Asp Ser Asp Tyr Gln Leu
            340                 345                 350

ccg tac gtg ctc ggg tcg gct cac gag ggc tgc ctc ccg ccg ttc cca     1104
Pro Tyr Val Leu Gly Ser Ala His Glu Gly Cys Leu Pro Pro Phe Pro
        355                 360                 365

gcg gac gtt ttc atg att cct cag tac ggg tat ctg acg ctt aat gat     1152
Ala Asp Val Phe Met Ile Pro Gln Tyr Gly Tyr Leu Thr Leu Asn Asp
    370                 375                 380

gga agc cag gcc gtg ggt cgt tcg tcc ttt tac tgc ctg gaa tat ttc     1200
Gly Ser Gln Ala Val Gly Arg Ser Ser Phe Tyr Cys Leu Glu Tyr Phe
```

-continued

```
385                 390                 395                 400

ccg tcg caa atg cta aga acg ggt aac aac ttc cag ttc agc tac gag      1248
Pro Ser Gln Met Leu Arg Thr Gly Asn Asn Phe Gln Phe Ser Tyr Glu
                405                 410                 415

ttt gag aac gta cct ttc cat agc agc tac gct cac agc caa agc ctg      1296
Phe Glu Asn Val Pro Phe His Ser Ser Tyr Ala His Ser Gln Ser Leu
            420                 425                 430

gac cga cta atg aat cca ctc atc gac caa tac ttg tac tat ctc tca      1344
Asp Arg Leu Met Asn Pro Leu Ile Asp Gln Tyr Leu Tyr Tyr Leu Ser
        435                 440                 445

aag act att aac ggt tct gga cag aat caa caa acg cta aaa ttc agt      1392
Lys Thr Ile Asn Gly Ser Gly Gln Asn Gln Gln Thr Leu Lys Phe Ser
    450                 455                 460

gtg gcc gga ccc agc aac atg gct gtc cag gga aga aac tac ata cct      1440
Val Ala Gly Pro Ser Asn Met Ala Val Gln Gly Arg Asn Tyr Ile Pro
465                 470                 475                 480

gga ccc agc tac cga caa caa cgt gtc tca acc act gtg act caa aac      1488
Gly Pro Ser Tyr Arg Gln Gln Arg Val Ser Thr Thr Val Thr Gln Asn
                485                 490                 495

aac aac agc gaa ttt gct tgg cct gga gct tct tct tgg gct ctc aat      1536
Asn Asn Ser Glu Phe Ala Trp Pro Gly Ala Ser Ser Trp Ala Leu Asn
            500                 505                 510

gga cgt aat agc ttg atg aat cct gga cct gct atg gcc agc cac aaa      1584
Gly Arg Asn Ser Leu Met Asn Pro Gly Pro Ala Met Ala Ser His Lys
        515                 520                 525

gaa gga gag gac cgt ttc ttt cct ttg tct gga tct tta att ttt ggc      1632
Glu Gly Glu Asp Arg Phe Phe Pro Leu Ser Gly Ser Leu Ile Phe Gly
    530                 535                 540

aaa caa gga act gga aga gac aac gtg gat gcg gac aaa gtc atg ata      1680
Lys Gln Gly Thr Gly Arg Asp Asn Val Asp Ala Asp Lys Val Met Ile
545                 550                 555                 560

acc aac gaa gaa gaa att aaa act act aac ccg gta gca acg gag tcc      1728
Thr Asn Glu Glu Glu Ile Lys Thr Thr Asn Pro Val Ala Thr Glu Ser
                565                 570                 575

tat gga caa gtg gcc aca aac cac cag agt gcc caa gca cag gcg cag      1776
Tyr Gly Gln Val Ala Thr Asn His Gln Ser Ala Gln Ala Gln Ala Gln
            580                 585                 590

acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
        595                 600                 605

gac aga gat gtg tac ctg caa gga ccc att tgg gcc aaa att cct cac      1872
Asp Arg Asp Val Tyr Leu Gln Gly Pro Ile Trp Ala Lys Ile Pro His
    610                 615                 620

acg gac ggc aac ttt cac cct tct ccg ctg atg gga ggg ttt gga atg      1920
Thr Asp Gly Asn Phe His Pro Ser Pro Leu Met Gly Gly Phe Gly Met
625                 630                 635                 640

aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655

gat cct cca acg gcc ttc aac aag gac aag ctg aac tct ttc atc acc      2016
Asp Pro Pro Thr Ala Phe Asn Lys Asp Lys Leu Asn Ser Phe Ile Thr
            660                 665                 670

cag tat tct act ggc caa gtc agc gtg gag atc gag tgg gag ctg cag      2064
Gln Tyr Ser Thr Gly Gln Val Ser Val Glu Ile Glu Trp Glu Leu Gln
        675                 680                 685

aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
    690                 695                 700

tat tac aag tct aat aat gtt gaa ttt gct gtt aat act gaa ggt gta      2160
```

-continued

```
Tyr Tyr Lys Ser Asn Asn Val Glu Phe Ala Val Asn Thr Glu Gly Val
705                 710                 715                 720

tat agt gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725                 730                 735


<210> SEQ ID NO 6
<211> LENGTH: 736
<212> TYPE: PRT
<213> ORGANISM: adeno-associated virus 9

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
```

```
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 7
<211> LENGTH: 2208
<212> TYPE: DNA
<213> ORGANISM: Artificial Sequence

```
<220> FEATURE:
<223> OTHER INFORMATION: AAV1-yfVP1
<220> FEATURE:
<221> NAME/KEY: CDS
<222> LOCATION: (1)..(2208)
<223> OTHER INFORMATION: AAV1-yfVP1

<400> SEQUENCE: 7

atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15

gag ggc att cgc gag tgg tgg gac ttg aaa cct gga gcc ccg aag ccc      96
Glu Gly Ile Arg Glu Trp Trp Asp Leu Lys Pro Gly Ala Pro Lys Pro
            20                  25                  30

aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45

ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60

gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80

cag cag ctc aaa gcg ggt gac aat ccg tac ctg cgg tat aac cac gcc     288
Gln Gln Leu Lys Ala Gly Asp Asn Pro Tyr Leu Arg Tyr Asn His Ala
                85                  90                  95

gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
            100                 105                 110

aac ctc ggg cga gca gtc ttc cag gcc aag aag cgg gtt ctc gaa cct     384
Asn Leu Gly Arg Ala Val Phe Gln Ala Lys Lys Arg Val Leu Glu Pro
        115                 120                 125

ctc ggt ctg gtt gag gaa ggc gct aag acg gct cct gga aag aaa cgt     432
Leu Gly Leu Val Glu Glu Gly Ala Lys Thr Ala Pro Gly Lys Lys Arg
    130                 135                 140

ccg gta gag cag tcg cca caa gag cca gac tcc tcc tcg ggc atc ggc     480
Pro Val Glu Gln Ser Pro Gln Glu Pro Asp Ser Ser Ser Gly Ile Gly
145                 150                 155                 160

aag aca ggc cag cag ccc gct aaa aag aga ctc aat ttt ggt cag act     528
Lys Thr Gly Gln Gln Pro Ala Lys Lys Arg Leu Asn Phe Gly Gln Thr
                165                 170                 175

ggc gac tca gag tca gtc ccc gat cca caa cct ctc gga gaa cct cca     576
Gly Asp Ser Glu Ser Val Pro Asp Pro Gln Pro Leu Gly Glu Pro Pro
            180                 185                 190

gca acc ccc gct gct gtg gga cct act aca atg gct tca ggc ggt ggc     624
Ala Thr Pro Ala Ala Val Gly Pro Thr Thr Met Ala Ser Gly Gly Gly
        195                 200                 205

gca cca atg gca gac aat aac gaa ggc gcc gac gga gtg ggt aat gcc     672
Ala Pro Met Ala Asp Asn Asn Glu Gly Ala Asp Gly Val Gly Asn Ala
    210                 215                 220

tca gga aat tgg cat tgc gat tcc aca tgg ctg ggc gac aga gtc atc     720
Ser Gly Asn Trp His Cys Asp Ser Thr Trp Leu Gly Asp Arg Val Ile
225                 230                 235                 240

acc acc agc acc cgc acc tgg gcc ttg ccc acc tac aat aac cac ctc     768
Thr Thr Ser Thr Arg Thr Trp Ala Leu Pro Thr Tyr Asn Asn His Leu
                245                 250                 255

tac aag caa atc tcc agt gct tca acg ggg gcc agc aac gac aac cac     816
Tyr Lys Gln Ile Ser Ser Ala Ser Thr Gly Ala Ser Asn Asp Asn His
            260                 265                 270

tac ttc ggc tac agc acc ccc tgg ggg tat ttt gat ttc aac aga ttc     864
Tyr Phe Gly Tyr Ser Thr Pro Trp Gly Tyr Phe Asp Phe Asn Arg Phe
```

-continued

```
        275                 280                 285

cac tgc cac ttt tca cca cgt gac tgg cag cga ctc atc aac aac aat      912
His Cys His Phe Ser Pro Arg Asp Trp Gln Arg Leu Ile Asn Asn Asn
    290                 295                 300

tgg gga ttc cgg ccc aag aga ctc aac ttc aaa ctc ttc aac atc caa      960
Trp Gly Phe Arg Pro Lys Arg Leu Asn Phe Lys Leu Phe Asn Ile Gln
305                 310                 315                 320

gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335

ctt acc agc acg gtt caa gtc ttc tcg gac tcg gag tac cag ctt ccg     1056
Leu Thr Ser Thr Val Gln Val Phe Ser Asp Ser Glu Tyr Gln Leu Pro
            340                 345                 350

tac gtc ctc ggc tct gcg cac cag ggc tgc ctc cct ccg ttc ccg gcg     1104
Tyr Val Leu Gly Ser Ala His Gln Gly Cys Leu Pro Pro Phe Pro Ala
        355                 360                 365

gac gtg ttc atg att ccg caa tac ggc tac ctg acg ctc aac aat ggc     1152
Asp Val Phe Met Ile Pro Gln Tyr Gly Tyr Leu Thr Leu Asn Asn Gly
    370                 375                 380

agc caa gcc gtg gga cgt tca tcc ttt tac tgc ctg gaa tat ttc cct     1200
Ser Gln Ala Val Gly Arg Ser Ser Phe Tyr Cys Leu Glu Tyr Phe Pro
385                 390                 395                 400

tct cag atg ctg aga acg ggc aac aac ttt acc ttc agc tac acc ttt     1248
Ser Gln Met Leu Arg Thr Gly Asn Asn Phe Thr Phe Ser Tyr Thr Phe
                405                 410                 415

gag gaa gtg cct ttc cac agc agc tac gcg cac agc cag agc ctg gac     1296
Glu Glu Val Pro Phe His Ser Ser Tyr Ala His Ser Gln Ser Leu Asp
            420                 425                 430

cgg ctg atg aat cct ctc atc gac caa tac ctg tat ttc ctg aac aga     1344
Arg Leu Met Asn Pro Leu Ile Asp Gln Tyr Leu Tyr Phe Leu Asn Arg
        435                 440                 445

act caa aat cag tcc gga agt gcc caa aac aag gac ttg ctg ttt agc     1392
Thr Gln Asn Gln Ser Gly Ser Ala Gln Asn Lys Asp Leu Leu Phe Ser
    450                 455                 460

cgt ggg tct cca gct ggc atg tct gtt cag ccc aaa aac tgg cta cct     1440
Arg Gly Ser Pro Ala Gly Met Ser Val Gln Pro Lys Asn Trp Leu Pro
465                 470                 475                 480

gga ccc tgt tat cgg cag cag cgc gtt tct aaa aca aaa aca gac aac     1488
Gly Pro Cys Tyr Arg Gln Gln Arg Val Ser Lys Thr Lys Thr Asp Asn
                485                 490                 495

aac aac agc aat ttt acc tgg act ggt gct tca aaa tat aac ctc aat     1536
Asn Asn Ser Asn Phe Thr Trp Thr Gly Ala Ser Lys Tyr Asn Leu Asn
            500                 505                 510

ggg cgt gaa tcc atc atc aac cct ggc act gct atg gcc tca cac aaa     1584
Gly Arg Glu Ser Ile Ile Asn Pro Gly Thr Ala Met Ala Ser His Lys
        515                 520                 525

gac gac gaa gac aag ttc ttt ccc atg agc ggt gtc atg att ttt gga     1632
Asp Asp Glu Asp Lys Phe Phe Pro Met Ser Gly Val Met Ile Phe Gly
    530                 535                 540

aaa gag agc gcc gga gct tca aac act gca ttg gac aat gtc atg att     1680
Lys Glu Ser Ala Gly Ala Ser Asn Thr Ala Leu Asp Asn Val Met Ile
545                 550                 555                 560

aca gac gaa gag gaa att aaa gcc act aac cct gtg gcc acc gaa aga     1728
Thr Asp Glu Glu Glu Ile Lys Ala Thr Asn Pro Val Ala Thr Glu Arg
                565                 570                 575

ttt ggg acc gtg gca gtc aat ttc cag agc agc agc aca gac cct gcg     1776
Phe Gly Thr Val Ala Val Asn Phe Gln Ser Ser Ser Thr Asp Pro Ala
            580                 585                 590

acc gga gat gtg cat gct atg gga gca tta cct ggc atg gtg tgg caa     1824
```

-continued

```
Thr Gly Asp Val His Ala Met Gly Ala Leu Pro Gly Met Val Trp Gln
        595                 600                 605

gat aga gac gtg tac ctg cag ggt ccc att tgg gcc aaa att cct cac      1872
Asp Arg Asp Val Tyr Leu Gln Gly Pro Ile Trp Ala Lys Ile Pro His
    610                 615                 620

aca gat gga cac ttt cac ccg tct cct ctt atg ggc ggc ttt gga ctc      1920
Thr Asp Gly His Phe His Pro Ser Pro Leu Met Gly Gly Phe Gly Leu
625                 630                 635                 640

aag aac ccg cct cct cag atc ctc atc aaa aac acg cct gtt cct gcg      1968
Lys Asn Pro Pro Pro Gln Ile Leu Ile Lys Asn Thr Pro Val Pro Ala
                645                 650                 655

aat cct ccg gcg gag ttt tca gct aca aag ttt gct tca ttc atc acc      2016
Asn Pro Pro Ala Glu Phe Ser Ala Thr Lys Phe Ala Ser Phe Ile Thr
            660                 665                 670

caa tac tcc aca gga caa gtg agt gtg gaa att gaa tgg gag ctg cag      2064
Gln Tyr Ser Thr Gly Gln Val Ser Val Glu Ile Glu Trp Glu Leu Gln
        675                 680                 685

aaa gaa aac agc aag cgc tgg aat ccc gaa gtg cag tac aca tcc aat      2112
Lys Glu Asn Ser Lys Arg Trp Asn Pro Glu Val Gln Tyr Thr Ser Asn
    690                 695                 700

tat gca aaa tct gcc aac gtt gat ttt act gtg gac aac aat gga ctt      2160
Tyr Ala Lys Ser Ala Asn Val Asp Phe Thr Val Asp Asn Asn Gly Leu
705                 710                 715                 720

tat act gag cct cgc ccc att ggc acc cgt tac ctt acc cgt ccc ctg      2208
Tyr Thr Glu Pro Arg Pro Ile Gly Thr Arg Tyr Leu Thr Arg Pro Leu
                725                 730                 735


<210> SEQ ID NO 8
<211> LENGTH: 736
<212> TYPE: PRT
<213> ORGANISM: Artificial Sequence
<220> FEATURE:
<223> OTHER INFORMATION: Synthetic Construct

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
```

-continued

```
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Phe Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605
```

-continued

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 9
<211> LENGTH: 2205
<212> TYPE: DNA
<213> ORGANISM: Artificial Sequence
<220> FEATURE:
<223> OTHER INFORMATION: AAV2-yfVP1
<220> FEATURE:
<221> NAME/KEY: CDS
<222> LOCATION: (1)..(2205)
<223> OTHER INFORMATION: AAV2-yfVP1

<400> SEQUENCE: 9

atg gct gcc gat ggt tat ctt cca gat tgg ctc gag gac act ctc tct       48
Met Ala Ala Asp Gly Tyr Leu Pro Asp Trp Leu Glu Asp Thr Leu Ser
1               5                   10                  15

gaa gga ata aga cag tgg tgg aag ctc aaa cct ggc cca cca cca cca       96
Glu Gly Ile Arg Gln Trp Trp Lys Leu Lys Pro Gly Pro Pro Pro Pro
            20                  25                  30

aag ccc gca gag cgg cat aag gac gac agc agg ggt ctt gtg ctt cct      144
Lys Pro Ala Glu Arg His Lys Asp Asp Ser Arg Gly Leu Val Leu Pro
        35                  40                  45

ggg tac aag tac ctc gga ccc ttc aac gga ctc gac aag gga gag ccg      192
Gly Tyr Lys Tyr Leu Gly Pro Phe Asn Gly Leu Asp Lys Gly Glu Pro
    50                  55                  60

gtc aac gag gca gac gcc gcg gcc ctc gag cac gac aaa gcc tac gac      240
Val Asn Glu Ala Asp Ala Ala Ala Leu Glu His Asp Lys Ala Tyr Asp
65                  70                  75                  80

cgg cag ctc gac agc gga gac aac ccg tac ctc aag tac aac cac gcc      288
Arg Gln Leu Asp Ser Gly Asp Asn Pro Tyr Leu Lys Tyr Asn His Ala
                85                  90                  95

gac gcg gag ttt cag gag cgc ctt aaa gaa gat acg tct ttt ggg ggc      336
Asp Ala Glu Phe Gln Glu Arg Leu Lys Glu Asp Thr Ser Phe Gly Gly
            100                 105                 110

aac ctc gga cga gca gtc ttc cag gcg aaa aag agg gtt ctt gaa cct      384
Asn Leu Gly Arg Ala Val Phe Gln Ala Lys Lys Arg Val Leu Glu Pro
        115                 120                 125

ctg ggc ctg gtt gag gaa cct gtt aag acg gct ccg gga aaa aag agg      432
Leu Gly Leu Val Glu Glu Pro Val Lys Thr Ala Pro Gly Lys Lys Arg
    130                 135                 140

ccg gta gag cac tct cct gtg gag cca gac tcc tcc tcg gga acc gga      480
Pro Val Glu His Ser Pro Val Glu Pro Asp Ser Ser Ser Gly Thr Gly
145                 150                 155                 160
```

-continued

```
aag gcg ggc cag cag cct gca aga aaa aga ttg aat ttt ggt cag act      528
Lys Ala Gly Gln Gln Pro Ala Arg Lys Arg Leu Asn Phe Gly Gln Thr
                165                 170                 175

gga gac gca gac tca gta cct gac ccc cag cct ctc gga cag cca cca      576
Gly Asp Ala Asp Ser Val Pro Asp Pro Gln Pro Leu Gly Gln Pro Pro
            180                 185                 190

gca gcc ccc tct ggt ctg gga act aat acg atg gct aca ggc agt ggc      624
Ala Ala Pro Ser Gly Leu Gly Thr Asn Thr Met Ala Thr Gly Ser Gly
        195                 200                 205

gca cca atg gca gac aat aac gag ggc gcc gac gga gtg ggt aat tcc      672
Ala Pro Met Ala Asp Asn Asn Glu Gly Ala Asp Gly Val Gly Asn Ser
    210                 215                 220

tcg gga aat tgg cat tgc gat tcc aca tgg atg ggc gac aga gtc atc      720
Ser Gly Asn Trp His Cys Asp Ser Thr Trp Met Gly Asp Arg Val Ile
225                 230                 235                 240

acc acc agc acc cga acc tgg gcc ctg ccc acc tac aac aac cac ctc      768
Thr Thr Ser Thr Arg Thr Trp Ala Leu Pro Thr Tyr Asn Asn His Leu
                245                 250                 255

tac aaa caa att tcc agc caa tca gga gcc tcg aac gac aat cac tac      816
Tyr Lys Gln Ile Ser Ser Gln Ser Gly Ala Ser Asn Asp Asn His Tyr
            260                 265                 270

ttt ggc tac agc acc cct tgg ggg tat ttt gac ttc aac aga ttc cac      864
Phe Gly Tyr Ser Thr Pro Trp Gly Tyr Phe Asp Phe Asn Arg Phe His
        275                 280                 285

tgc cac ttt tca cca cgt gac tgg caa aga ctc atc aac aac aac tgg      912
Cys His Phe Ser Pro Arg Asp Trp Gln Arg Leu Ile Asn Asn Asn Trp
    290                 295                 300

gga ttc cga ccc aag aga ctc aac ttc aag ctc ttt aac att caa gtc      960
Gly Phe Arg Pro Lys Arg Leu Asn Phe Lys Leu Phe Asn Ile Gln Val
305                 310                 315                 320

aaa gag gtc acg cag aat gac ggt acg acg acg att gcc aat aac ctt     1008
Lys Glu Val Thr Gln Asn Asp Gly Thr Thr Thr Ile Ala Asn Asn Leu
                325                 330                 335

acc agc acg gtt cag gtg ttt act gac tcg gag tac cag ctc ccg tac     1056
Thr Ser Thr Val Gln Val Phe Thr Asp Ser Glu Tyr Gln Leu Pro Tyr
            340                 345                 350

gtc ctc ggc tcg gcg cat caa gga tgc ctc ccg ccg ttc cca gca gac     1104
Val Leu Gly Ser Ala His Gln Gly Cys Leu Pro Pro Phe Pro Ala Asp
        355                 360                 365

gtc ttc atg gtg cca cag tat gga tac ctc acc ctg aac aac ggg agt     1152
Val Phe Met Val Pro Gln Tyr Gly Tyr Leu Thr Leu Asn Asn Gly Ser
    370                 375                 380

cag gca gta gga cgc tct tca ttt tac tgc ctg gag tac ttt cct tct     1200
Gln Ala Val Gly Arg Ser Ser Phe Tyr Cys Leu Glu Tyr Phe Pro Ser
385                 390                 395                 400

cag atg ctg cgt acc gga aac aac ttt acc ttc agc tac act ttt gag     1248
Gln Met Leu Arg Thr Gly Asn Asn Phe Thr Phe Ser Tyr Thr Phe Glu
                405                 410                 415

gac gtt cct ttc cac agc agc tac gct cac agc cag agt ctg gac cgt     1296
Asp Val Pro Phe His Ser Ser Tyr Ala His Ser Gln Ser Leu Asp Arg
            420                 425                 430

ctc atg aat cct ctc atc gac cag tac ctg tat ttc ttg agc aga aca     1344
Leu Met Asn Pro Leu Ile Asp Gln Tyr Leu Tyr Phe Leu Ser Arg Thr
        435                 440                 445

aac act cca agt gga acc acc acg cag tca agg ctt cag ttt tct cag     1392
Asn Thr Pro Ser Gly Thr Thr Thr Gln Ser Arg Leu Gln Phe Ser Gln
    450                 455                 460

gcc gga gcg agt gac att cgg gac cag tct agg aac tgg ctt cct gga     1440
Ala Gly Ala Ser Asp Ile Arg Asp Gln Ser Arg Asn Trp Leu Pro Gly
465                 470                 475                 480
```

```
ccc tgt tac cgc cag cag cga gta tca aag aca tct gcg gat aac aac     1488
Pro Cys Tyr Arg Gln Gln Arg Val Ser Lys Thr Ser Ala Asp Asn Asn
                485                 490                 495

aac agt gaa tac tcg tgg act gga gct acc aag tac cac ctc aat ggc     1536
Asn Ser Glu Tyr Ser Trp Thr Gly Ala Thr Lys Tyr His Leu Asn Gly
            500                 505                 510

aga gac tct ctg gtg aat ccg ggc ccg gcc atg gca agc cac aag gac     1584
Arg Asp Ser Leu Val Asn Pro Gly Pro Ala Met Ala Ser His Lys Asp
        515                 520                 525

gat gaa gaa aag ttt ttt cct cag agc ggg gtt ctc atc ttt ggg aag     1632
Asp Glu Glu Lys Phe Phe Pro Gln Ser Gly Val Leu Ile Phe Gly Lys
    530                 535                 540

caa ggc tca gag aaa aca aat gtg gac att gaa aag gtc atg att aca     1680
Gln Gly Ser Glu Lys Thr Asn Val Asp Ile Glu Lys Val Met Ile Thr
545                 550                 555                 560

gac gaa gag gaa atc agg aca acc aat ccc gtg gct acg gag cag tat     1728
Asp Glu Glu Glu Ile Arg Thr Thr Asn Pro Val Ala Thr Glu Gln Tyr
                565                 570                 575

ggt tct gta tct acc aac ctc cag aga ggc aac aga caa gca gct acc     1776
Gly Ser Val Ser Thr Asn Leu Gln Arg Gly Asn Arg Gln Ala Ala Thr
            580                 585                 590

gca gat gtc aac aca caa ggc gtt ctt cca ggc atg gtc tgg cag gac     1824
Ala Asp Val Asn Thr Gln Gly Val Leu Pro Gly Met Val Trp Gln Asp
        595                 600                 605

aga gat gtg tac ctt cag ggg ccc atc tgg gca aag att cca cac acg     1872
Arg Asp Val Tyr Leu Gln Gly Pro Ile Trp Ala Lys Ile Pro His Thr
    610                 615                 620

gac gga cat ttt cac ccc tct ccc ctc atg ggt gga ttc gga ctt aaa     1920
Asp Gly His Phe His Pro Ser Pro Leu Met Gly Gly Phe Gly Leu Lys
625                 630                 635                 640

cac cct cct cca cag att ctc atc aag aac acc ccg gta cct gcg aat     1968
His Pro Pro Pro Gln Ile Leu Ile Lys Asn Thr Pro Val Pro Ala Asn
                645                 650                 655

cct tcg acc acc ttc agt gcg gca aag ttt gct tcc ttc atc aca cag     2016
Pro Ser Thr Thr Phe Ser Ala Ala Lys Phe Ala Ser Phe Ile Thr Gln
            660                 665                 670

tac tcc acg gga cag gtc agc gtg gag atc gag tgg gag ctg cag aag     2064
Tyr Ser Thr Gly Gln Val Ser Val Glu Ile Glu Trp Glu Leu Gln Lys
        675                 680                 685

gaa aac agc aaa cgc tgg aat ccc gaa att cag tac act tcc aac tac     2112
Glu Asn Ser Lys Arg Trp Asn Pro Glu Ile Gln Tyr Thr Ser Asn Tyr
    690                 695                 700

aac aag tct gtt aat gtg gac ttt act gtg gac act aat ggc gtg tat     2160
Asn Lys Ser Val Asn Val Asp Phe Thr Val Asp Thr Asn Gly Val Tyr
705                 710                 715                 720

tca gag cct cgc ccc att ggc acc aga tac ctg act cgt aat ctg         2205
Ser Glu Pro Arg Pro Ile Gly Thr Arg Tyr Leu Thr Arg Asn Leu
                725                 730                 735


<210> SEQ ID NO 10
<211> LENGTH: 735
<212> TYPE: PRT
<213> ORGANISM: Artificial Sequence
<220> FEATURE:
<223> OTHER INFORMATION: Synthetic Construct

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
```

-continued

```
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Phe Leu Ser Arg Thr
        435                 440                 445
```

```
Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 11
<211> LENGTH: 2208
<212> TYPE: DNA
<213> ORGANISM: Artificial Sequence
<220> FEATURE:
<223> OTHER INFORMATION: AAV9-yfVP1
<220> FEATURE:
<221> NAME/KEY: CDS
<222> LOCATION: (1)..(2208)
<223> OTHER INFORMATION: AAV9-yfVP1

<400> SEQUENCE: 11

atg gct gcc gat ggt tat ctt cca gat tgg ctc gag gac aac ctt agt       48
Met Ala Ala Asp Gly Tyr Leu Pro Asp Trp Leu Glu Asp Asn Leu Ser
1               5                   10                  15

gaa gga att cgc gag tgg tgg gct ttg aaa cct gga gcc cct caa ccc       96
Glu Gly Ile Arg Glu Trp Trp Ala Leu Lys Pro Gly Ala Pro Gln Pro
            20                  25                  30

aag gca aat caa caa cat caa gac aac gct cga ggt ctt gtg ctt ccg      144
Lys Ala Asn Gln Gln His Gln Asp Asn Ala Arg Gly Leu Val Leu Pro
```

-continued

```
        35                  40                  45

ggt tac aaa tac ctt gga ccc ggc aac gga ctc gac aag ggg gag ccg      192
Gly Tyr Lys Tyr Leu Gly Pro Gly Asn Gly Leu Asp Lys Gly Glu Pro
    50                  55                  60

gtc aac gca gca gac gcg gcg gcc ctc gag cac gac aag gcc tac gac      240
Val Asn Ala Ala Asp Ala Ala Ala Leu Glu His Asp Lys Ala Tyr Asp
65                  70                  75                  80

cag cag ctc aag gcc gga gac aac ccg tac ctc aag tac aac cac gcc      288
Gln Gln Leu Lys Ala Gly Asp Asn Pro Tyr Leu Lys Tyr Asn His Ala
                85                  90                  95

gac gcc gag ttc cag gag cgg ctc aaa gaa gat acg tct ttt ggg ggc      336
Asp Ala Glu Phe Gln Glu Arg Leu Lys Glu Asp Thr Ser Phe Gly Gly
            100                 105                 110

aac ctc ggg cga gca gtc ttc cag gcc aaa aag agg ctt ctt gaa cct      384
Asn Leu Gly Arg Ala Val Phe Gln Ala Lys Lys Arg Leu Leu Glu Pro
        115                 120                 125

ctt ggt ctg gtt gag gaa gcg gct aag acg gct cct gga aag aag agg      432
Leu Gly Leu Val Glu Glu Ala Ala Lys Thr Ala Pro Gly Lys Lys Arg
    130                 135                 140

cct gta gag cag tct cct cag gaa ccg gac tcc tcc gcg ggt att ggc      480
Pro Val Glu Gln Ser Pro Gln Glu Pro Asp Ser Ser Ala Gly Ile Gly
145                 150                 155                 160

aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                165                 170                 175

ggc gac aca gag tca gtc cca gac cct caa cca atc gga gaa cct ccc      576
Gly Asp Thr Glu Ser Val Pro Asp Pro Gln Pro Ile Gly Glu Pro Pro
            180                 185                 190

gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
        195                 200                 205

gca cca gtg gca gac aat aac gaa ggt gcc gat gga gtg ggt agt tcc      672
Ala Pro Val Ala Asp Asn Asn Glu Gly Ala Asp Gly Val Gly Ser Ser
    210                 215                 220

tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225                 230                 235                 240

acc acc agc acc cga acc tgg gcc ctg ccc acc tac aac aat cac ctc      768
Thr Thr Ser Thr Arg Thr Trp Ala Leu Pro Thr Tyr Asn Asn His Leu
                245                 250                 255

tac aag caa atc tcc aac agc aca tct gga gga tct tca aat gac aac      816
Tyr Lys Gln Ile Ser Asn Ser Thr Ser Gly Gly Ser Ser Asn Asp Asn
            260                 265                 270

gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
        275                 280                 285

ttc cac tgc cac ttc tca cca cgt gac tgg cag cga ctc atc aac aac      912
Phe His Cys His Phe Ser Pro Arg Asp Trp Gln Arg Leu Ile Asn Asn
    290                 295                 300

aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305                 310                 315                 320

cag gtc aaa gag gtt acg gac aac aat gga gtc aag acc atc gcc aat     1008
Gln Val Lys Glu Val Thr Asp Asn Asn Gly Val Lys Thr Ile Ala Asn
                325                 330                 335

aac ctt acc agc acg gtc cag gtc ttc acg gac tca gac tat cag ctc     1056
Asn Leu Thr Ser Thr Val Gln Val Phe Thr Asp Ser Asp Tyr Gln Leu
            340                 345                 350

ccg tac gtg ctc ggg tcg gct cac gag ggc tgc ctc ccg ccg ttc cca     1104
```

-continued

```
Pro Tyr Val Leu Gly Ser Ala His Glu Gly Cys Leu Pro Pro Phe Pro
        355                 360                 365

gcg gac gtt ttc atg att cct cag tac ggg tat ctg acg ctt aat gat      1152
Ala Asp Val Phe Met Ile Pro Gln Tyr Gly Tyr Leu Thr Leu Asn Asp
    370                 375                 380

gga agc cag gcc gtg ggt cgt tcg tcc ttt tac tgc ctg gaa tat ttc      1200
Gly Ser Gln Ala Val Gly Arg Ser Ser Phe Tyr Cys Leu Glu Tyr Phe
385                 390                 395                 400

ccg tcg caa atg cta aga acg ggt aac aac ttc cag ttc agc tac gag      1248
Pro Ser Gln Met Leu Arg Thr Gly Asn Asn Phe Gln Phe Ser Tyr Glu
                405                 410                 415

ttt gag aac gta cct ttc cat agc agc tac gct cac agc caa agc ctg      1296
Phe Glu Asn Val Pro Phe His Ser Ser Tyr Ala His Ser Gln Ser Leu
            420                 425                 430

gac cga cta atg aat cca ctc atc gac caa tac ttg tac ttt ctc tca      1344
Asp Arg Leu Met Asn Pro Leu Ile Asp Gln Tyr Leu Tyr Phe Leu Ser
        435                 440                 445

aag act att aac ggt tct gga cag aat caa caa acg cta aaa ttc agt      1392
Lys Thr Ile Asn Gly Ser Gly Gln Asn Gln Gln Thr Leu Lys Phe Ser
    450                 455                 460

gtg gcc gga ccc agc aac atg gct gtc cag gga aga aac tac ata cct      1440
Val Ala Gly Pro Ser Asn Met Ala Val Gln Gly Arg Asn Tyr Ile Pro
465                 470                 475                 480

gga ccc agc tac cga caa caa cgt gtc tca acc act gtg act caa aac      1488
Gly Pro Ser Tyr Arg Gln Gln Arg Val Ser Thr Thr Val Thr Gln Asn
                485                 490                 495

aac aac agc gaa ttt gct tgg cct gga gct tct tct tgg gct ctc aat      1536
Asn Asn Ser Glu Phe Ala Trp Pro Gly Ala Ser Ser Trp Ala Leu Asn
            500                 505                 510

gga cgt aat agc ttg atg aat cct gga cct gct atg gcc agc cac aaa      1584
Gly Arg Asn Ser Leu Met Asn Pro Gly Pro Ala Met Ala Ser His Lys
        515                 520                 525

gaa gga gag gac cgt ttc ttt cct ttg tct gga tct tta att ttt ggc      1632
Glu Gly Glu Asp Arg Phe Phe Pro Leu Ser Gly Ser Leu Ile Phe Gly
    530                 535                 540

aaa caa gga act gga aga gac aac gtg gat gcg gac aaa gtc atg ata      1680
Lys Gln Gly Thr Gly Arg Asp Asn Val Asp Ala Asp Lys Val Met Ile
545                 550                 555                 560

acc aac gaa gaa gaa att aaa act act aac ccg gta gca acg gag tcc      1728
Thr Asn Glu Glu Glu Ile Lys Thr Thr Asn Pro Val Ala Thr Glu Ser
                565                 570                 575

tat gga caa gtg gcc aca aac cac cag agt gcc caa gca cag gcg cag      1776
Tyr Gly Gln Val Ala Thr Asn His Gln Ser Ala Gln Ala Gln Ala Gln
            580                 585                 590

acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
        595                 600                 605

gac aga gat gtg tac ctg caa gga ccc att tgg gcc aaa att cct cac      1872
Asp Arg Asp Val Tyr Leu Gln Gly Pro Ile Trp Ala Lys Ile Pro His
    610                 615                 620

acg gac ggc aac ttt cac cct tct ccg ctg atg gga ggg ttt gga atg      1920
Thr Asp Gly Asn Phe His Pro Ser Pro Leu Met Gly Gly Phe Gly Met
625                 630                 635                 640

aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655

gat cct cca acg gcc ttc aac aag gac aag ctg aac tct ttc atc acc      2016
Asp Pro Pro Thr Ala Phe Asn Lys Asp Lys Leu Asn Ser Phe Ile Thr
            660                 665                 670
```

```
cag tat tct act ggc caa gtc agc gtg gag atc gag tgg gag ctg cag     2064
Gln Tyr Ser Thr Gly Gln Val Ser Val Glu Ile Glu Trp Glu Leu Gln
        675                 680                 685

aag gaa aac agc aag cgc tgg aac ccg gag atc cag tac act tcc aac     2112
Lys Glu Asn Ser Lys Arg Trp Asn Pro Glu Ile Gln Tyr Thr Ser Asn
    690                 695                 700

tat tac aag tct aat aat gtt gaa ttt gct gtt aat act gaa ggt gta     2160
Tyr Tyr Lys Ser Asn Asn Val Glu Phe Ala Val Asn Thr Glu Gly Val
705                 710                 715                 720

tat agt gaa ccc cgc ccc att ggc acc aga tac ctg act cgt aat ctg     2208
Tyr Ser Glu Pro Arg Pro Ile Gly Thr Arg Tyr Leu Thr Arg Asn Leu
                725                 730                 735


<210> SEQ ID NO 12
<211> LENGTH: 736
<212> TYPE: PRT
<213> ORGANISM: Artificial Sequence
<220> FEATURE:
<223> OTHER INFORMATION: Synthetic Construct

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Phe Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 13
<211> LENGTH: 125
<212> TYPE: DNA
<213> ORGANISM: adeno-associated virus 3
<220> FEATURE:
<221> NAME/KEY: misc_feature
<222> LOCATION: (1)..(125)
<223> OTHER INFORMATION: Inverted Terminal Repeat

<400> SEQUENCE: 13

ttggccactc cctctatgcg cactcgctcg ctcggtgggg cctggcgacc aaaggtcgcc      60

agacggacgt gctttgcacg tccggcccca ccgagcgagc gagtgcgcat agagggagtg     120

gccaa                                                                 125


<210> SEQ ID NO 14
<211> LENGTH: 125
<212> TYPE: DNA
<213> ORGANISM: adeno-associated virus 3
<220> FEATURE:
<221> NAME/KEY: misc_feature
<222> LOCATION: (1)..(125)
<223> OTHER INFORMATION: Inverted Terminal Repeat

<400> SEQUENCE: 14

ttggccactc cctctatgcg cactcgctcg ctcggtgggg cctggcgacc aaaggtcgcc      60

agacggacgt gctttgcacg tccggcccca ccgagcgagc gagtgcgcat agagggagtg     120

gccaa                                                                 125


<210> SEQ ID NO 15
<211> LENGTH: 1611
<212> TYPE: DNA
<213> ORGANISM: adeno-associated virus 2
<220> FEATURE:
<221> NAME/KEY: CDS
<222> LOCATION: (1)..(1611)
<223> OTHER INFORMATION: AAV2 Rep protein

<400> SEQUENCE: 15

atg ccg ggg ttt tac gag att gtg att aag gtc ccc agc gac ctt gac       48
Met Pro Gly Phe Tyr Glu Ile Val Ile Lys Val Pro Ser Asp Leu Asp
1               5                   10                  15

gag cat ctg ccc ggc att tct gac agc ttt gtg aac tgg gtg gcc gag       96
Glu His Leu Pro Gly Ile Ser Asp Ser Phe Val Asn Trp Val Ala Glu
            20                  25                  30

aag gaa tgg gag ttg ccg cca gat tct gac atg gat ctg aat ctg att      144
Lys Glu Trp Glu Leu Pro Pro Asp Ser Asp Met Asp Leu Asn Leu Ile
        35                  40                  45

gag cag gca ccc ctg acc gtg gcc gag aag ctg cag cgc gac ttt ctg      192
Glu Gln Ala Pro Leu Thr Val Ala Glu Lys Leu Gln Arg Asp Phe Leu
    50                  55                  60

acg gaa tgg cgc cgt gtg agt aag gcc ccg gag gcc ctt ttc ttt gtg      240
Thr Glu Trp Arg Arg Val Ser Lys Ala Pro Glu Ala Leu Phe Phe Val
65                  70                  75                  80

caa ttt gag aag gga gag agc tac ttc cac atg cac gtg ctc gtg gaa      288
Gln Phe Glu Lys Gly Glu Ser Tyr Phe His Met His Val Leu Val Glu
                85                  90                  95

acc acc ggg gtg aaa tcc atg gtt ttg gga cgt ttc ctg agt cag att      336
```

```
Thr Thr Gly Val Lys Ser Met Val Leu Gly Arg Phe Leu Ser Gln Ile
            100                 105                 110

cgc gaa aaa ctg att cag aga att tac cgc ggg atc gag ccg act ttg      384
Arg Glu Lys Leu Ile Gln Arg Ile Tyr Arg Gly Ile Glu Pro Thr Leu
        115                 120                 125

cca aac tgg ttc gcg gtc aca aag acc aga aat ggc gcc gga ggc ggg      432
Pro Asn Trp Phe Ala Val Thr Lys Thr Arg Asn Gly Ala Gly Gly Gly
    130                 135                 140

aac aag gtg gtg gat gag tgc tac atc ccc aat tac ttg ctc ccc aaa      480
Asn Lys Val Val Asp Glu Cys Tyr Ile Pro Asn Tyr Leu Leu Pro Lys
145                 150                 155                 160

acc cag cct gag ctc cag tgg gcg tgg act aat atg gaa cag tat tta      528
Thr Gln Pro Glu Leu Gln Trp Ala Trp Thr Asn Met Glu Gln Tyr Leu
                165                 170                 175

agc gcc tgt ttg aat ctc acg gag cgt aaa cgg ttg gtg gcg cag cat      576
Ser Ala Cys Leu Asn Leu Thr Glu Arg Lys Arg Leu Val Ala Gln His
            180                 185                 190

ctg acg cac gtg tcg cag acg cag gag cag aac aaa gag aat cag aat      624
Leu Thr His Val Ser Gln Thr Gln Glu Gln Asn Lys Glu Asn Gln Asn
        195                 200                 205

ccc aat tct gat gcg ccg gtg atc aga tca aaa act tca gcc agg tac      672
Pro Asn Ser Asp Ala Pro Val Ile Arg Ser Lys Thr Ser Ala Arg Tyr
    210                 215                 220

atg gag ctg gtc ggg tgg ctc gtg gac aag ggg att acc tcg gag aag      720
Met Glu Leu Val Gly Trp Leu Val Asp Lys Gly Ile Thr Ser Glu Lys
225                 230                 235                 240

cag tgg atc cag gag gac cag gcc tca tac atc tcc ttc aat gcg gcc      768
Gln Trp Ile Gln Glu Asp Gln Ala Ser Tyr Ile Ser Phe Asn Ala Ala
                245                 250                 255

tcc aac tcg cgg tcc caa atc aag gct gcc ttg gac aat gcg gga aag      816
Ser Asn Ser Arg Ser Gln Ile Lys Ala Ala Leu Asp Asn Ala Gly Lys
            260                 265                 270

att atg agc ctg act aaa acc gcc ccc gac tac ctg gtg ggc cag cag      864
Ile Met Ser Leu Thr Lys Thr Ala Pro Asp Tyr Leu Val Gly Gln Gln
        275                 280                 285

ccc gtg gag gac att tcc agc aat cgg att tat aaa att ttg gaa cta      912
Pro Val Glu Asp Ile Ser Ser Asn Arg Ile Tyr Lys Ile Leu Glu Leu
    290                 295                 300

aac ggg tac gat ccc caa tat gcg gct tcc gtc ttt ctg gga tgg gcc      960
Asn Gly Tyr Asp Pro Gln Tyr Ala Ala Ser Val Phe Leu Gly Trp Ala
305                 310                 315                 320

acg aaa aag ttc ggc aag agg aac acc atc tgg ctg ttt ggg cct gca     1008
Thr Lys Lys Phe Gly Lys Arg Asn Thr Ile Trp Leu Phe Gly Pro Ala
                325                 330                 335

act acc ggg aag acc aac atc gcg gag gcc ata gcc cac act gtg ccc     1056
Thr Thr Gly Lys Thr Asn Ile Ala Glu Ala Ile Ala His Thr Val Pro
            340                 345                 350

ttc tac ggg tgc gta aac tgg acc aat gag aac ttt ccc ttc aac gac     1104
Phe Tyr Gly Cys Val Asn Trp Thr Asn Glu Asn Phe Pro Phe Asn Asp
        355                 360                 365

tgt gtc gac aag atg gtg atc tgg tgg gag gag ggg aag atg acc gcc     1152
Cys Val Asp Lys Met Val Ile Trp Trp Glu Glu Gly Lys Met Thr Ala
    370                 375                 380

aag gtc gtg gag tcg gcc aaa gcc att ctc gga gga agc aag gtg cgc     1200
Lys Val Val Glu Ser Ala Lys Ala Ile Leu Gly Gly Ser Lys Val Arg
385                 390                 395                 400

gtg gac cag aaa tgc aag tcc tcg gcc cag ata gac ccg act ccc gtg     1248
Val Asp Gln Lys Cys Lys Ser Ser Ala Gln Ile Asp Pro Thr Pro Val
                405                 410                 415
```

```
atc gtc acc tcc aac acc aac atg tgc gcc gtg att gac ggg aac tca      1296
Ile Val Thr Ser Asn Thr Asn Met Cys Ala Val Ile Asp Gly Asn Ser
            420                 425                 430

acg acc ttc gaa cac cag cag ccg ttg caa gac cgg atg ttc aaa ttt      1344
Thr Thr Phe Glu His Gln Gln Pro Leu Gln Asp Arg Met Phe Lys Phe
        435                 440                 445

gaa ctc acc cgc cgt ctg gat cat gac ttt ggg aag gtc acc aag cag      1392
Glu Leu Thr Arg Arg Leu Asp His Asp Phe Gly Lys Val Thr Lys Gln
    450                 455                 460

gaa gtc aaa gac ttt ttc cgg tgg gca aag gat cac gtg gtt gag gtg      1440
Glu Val Lys Asp Phe Phe Arg Trp Ala Lys Asp His Val Val Glu Val
465                 470                 475                 480

gag cat gaa ttc tac gtc aaa aag ggt gga gcc aag aaa aga ccc gcc      1488
Glu His Glu Phe Tyr Val Lys Lys Gly Gly Ala Lys Lys Arg Pro Ala
                485                 490                 495

ccc agt gac gca gat ata agt gag ccc aaa cgg gtg cgc gag tca gtt      1536
Pro Ser Asp Ala Asp Ile Ser Glu Pro Lys Arg Val Arg Glu Ser Val
            500                 505                 510

gcg cag cca tcg acg tca gac gcg gaa gct tcg atc aac tac gca gac      1584
Ala Gln Pro Ser Thr Ser Asp Ala Glu Ala Ser Ile Asn Tyr Ala Asp
        515                 520                 525

aga ttg gct cga gga cac tct ctc tga                                  1611
Arg Leu Ala Arg Gly His Ser Leu
    530                 535


<210> SEQ ID NO 16
<211> LENGTH: 536
<212> TYPE: PRT
<213> ORGANISM: adeno-associated virus 2

<400> SEQUENCE: 16

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205
```

```
Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Leu Ala Arg Gly His Ser Leu
    530                 535
```

<210> SEQ ID NO 17
<211> LENGTH: 32
<212> TYPE: DNA
<213> ORGANISM: Artificial Sequence
<220> FEATURE:
<223> OTHER INFORMATION: Primer AAV1-F

<400> SEQUENCE: 17
cgaccaatac ctgtatttcc tgaacagaac tc 32

<210> SEQ ID NO 18
<211> LENGTH: 32
<212> TYPE: DNA

<213> ORGANISM: Artificial Sequence
<220> FEATURE:
<223> OTHER INFORMATION: Primer yfAAV1-R

<400> SEQUENCE: 18
gagttctgtt caggaaatac aggtattggt cg 32

<210> SEQ ID NO 19
<211> LENGTH: 34
<212> TYPE: DNA
<213> ORGANISM: Artificial Sequence
<220> FEATURE:
<223> OTHER INFORMATION: Primer yfAAV2-F

<400> SEQUENCE: 19
cgaccagtac ctgtatttct tgagcagaac aaac 34

<210> SEQ ID NO 20
<211> LENGTH: 34
<212> TYPE: DNA
<213> ORGANISM: Artificial Sequence
<220> FEATURE:
<223> OTHER INFORMATION: Primer yfAAV2-R

<400> SEQUENCE: 20
gtttgttctg ctcaagaaat acaggtactg gtcg 34

<210> SEQ ID NO 21
<211> LENGTH: 30
<212> TYPE: DNA
<213> ORGANISM: Artificial Sequence
<220> FEATURE:
<223> OTHER INFORMATION: Primer yfAAV9-F

<400> SEQUENCE: 21
cgaccaatac ttgtactttc tctcaaagac 30

<210> SEQ ID NO 22
<211> LENGTH: 30
<212> TYPE: DNA
<213> ORGANISM: Artificial Sequence
<220> FEATURE:
<223> OTHER INFORMATION: Primer yfAAV9-R

<400> SEQUENCE: 22
gtctttgaga gaaagtacaa gtattggtcg 30

<210> SEQ ID NO 23
<211> LENGTH: 1114
<212> TYPE: DNA
<213> ORGANISM: Homo sapiens
<220> FEATURE:
<221> NAME/KEY: misc_feature
<222> LOCATION: (1)..(1114)
<223> OTHER INFORMATION: SynI promoter

<400> SEQUENCE: 23
aagggttttg gctacgtcca gagcagagga atgagggcat gtagactaaa tatgttcgtg 60
tggaagaggc tgaatacaca tcagagttag tgctgcagga aatgcttctg cattgcatac 120
ccagagtttc cttgctcatc tgagagcatg tgttttttcc agatgtgtgt acttgtgtga 180
gattctctgg gtgtgtgtca atgtgttgcc tgaacgtgca ttgctcaata tgctcatgtg 240
tgttaccctg ggcttgtaca tctacatata tacctggatg cccgtgtgtt ctgtgatgta 300
catataccct gtgtcattcc ttgtttttct atttgtgtta ttccatgtgt tccttcaggc 360
tctcactacc caagtgtcca cctccgcctg tctggtgatg tttacgctac cccgtgctct 420
tttctttgcc tgacagtgtt gtcgtggaag acatctcgcc aggaacactg cagtaaggag 480
aatttctagt tttatgttcc cctccgagta tgcttctatc ccgaccctca accccaaaat 540
gccttcagag gtgaaaatca acactggaaa cacaagtatc tgggaagggt aacaatgcaa 600
gttagcctga ggatttagga ggaggctgaa aaacagagta ggagccttac tacgggtcca 660
gaccctacgg acaagaaccc ccactcccac tccccaaatt gcgcattccc tcccccatca 720
gagggggagg ggaagaggat gcagcgcggc gcggcgcgtg cgcactgtcg gatttagtac 780
cgcggacaga gccttcgccc ccgctgccgg cgcgcgccac cacctcccca gcaccaaagg 840
cgggctgacg tcactctcca gccctcccca aactccccta cctcaccgcc ttggtcgcgt 900
ccgtgcagcg gtgagtccag tcgggccgca ccacaagagg tgcaagatag gggggtgcag 960
gcgcgaccat acgctctgcg gcggcagagc ctcagcgctg cctcagtctg cagcgggcag 1020
cagaggagtc gcgtcgtgcc agagagcgcc gccgtgctcc tgagcccctt gcgctccgcc 1080
cccgcggccc accgacccac tgccccttgg atcc 1114

<210> SEQ ID NO 24
<211> LENGTH: 1311
<212> TYPE: DNA
<213> ORGANISM: Homo sapiens
<220> FEATURE:
<221> NAME/KEY: misc_feature
<222> LOCATION: (1)..(1311)
<223> OTHER INFORMATION: MBP promoter

<400> SEQUENCE: 24
agatctgcat gtttcactaa ttgtgtaata atgctctgct ctataaatat ccaaatgtaa 60
aagtctgcat tgggatttcg tttgactgaa ggcaatatta acgactaaac tgcactcgcc 120
cctaccaaaa acgctgcaca tccatagatt tagacttctt cgcatacttc ttatgtgttg 180
ggagaagcta ctttggggac aaaaatgccc ttctctgtgc ctcacaaata actgcattca 240
gggacacaaa gcccaactgt tgcaaaaata ttagtattca gatgttcttg tgttttgtta 300
atgcatttaa ttatgtacaa tatagctatt gttttccttt cacatttgca ttaatttata 360
ttagctagag aacataaagc acagctataa aatcagacta atcatttctg ttgttcttgc 420
aacctataaa taagcattgc atccctgcaa aaactgcagc tttgtactga ccacagtatt 480
cttcacgttg ctttttcaaa cactacagtg caatgatgta cttaataata tgttataaag 540
ctaattctaa atgccccact tctttcatgc atgaattgca aaaagatgtg gcaagttttg 600
tttctaccaa gaaaactaaa aacacctttt gtcaaataaa tgctccttgc atatttaact 660
tatgcaccag tggcctttta aacagtcaat gtcccatcaa ggtgcctgca catctgggct 720
ctccgggagc agccatggca gcacccggga agaaacgctg atgtggctgc tctgcatgct 780
cagatgactt catcgggaag cctgggtgca ttttacgctg ggtgccaaat ctcgagtaac 840
tgaggaattc ccagagcctt ctgaaacaca gagctgcaat aaggctgctc catccaggtt 900
agctccatcc taggccaagg gctttatgag gactgcacat attctgtggg ttttatagga 960
gacagctagg tcaagacccc tcagagaaag ctgctttgtc cggtgctcag ctttgcacag 1020
gcccgtattc atatctcatt gttgtttgca ggagaggcag atgcgaacca gaacaatggg 1080
acctcctctc aggacacagc ggtgactgac tccaagcgca cagcggaccc gaagaatgcc 1140
tggcaggatg cccacccagc tgacccaggg agccgccccc acttgatccg cctcttttcc 1200
cgagatgccc cggggaggga ggacaacacc ttcaaagaca ggccctctga gtccgacgag 1260
ctccagacca tccaagaaga cagtgcagcc acctccgaga gcctggatgt g 1311

<210> SEQ ID NO 25
<211> LENGTH: 532
<212> TYPE: PRT
<213> ORGANISM: Artificial
<220> FEATURE:
<223> OTHER INFORMATION: modHEXB

<400> SEQUENCE: 25

Met Leu Leu Ala Leu Leu Thr Gln Val Ala Leu Val Val Gln Val Ala
1 5 10 15

Glu Ala Ala Arg Ala Pro Ser Val Ser Ala Lys Pro Gly Pro Ala Leu
20 25 30

Trp Pro Leu Pro Leu Ser Val Lys Met Thr Pro Asn Leu Leu His Leu
35 40 45

Ala Pro Glu Asn Phe Tyr Ile Ser His Ser Pro Asn Ser Thr Ala Gly
50 55 60

Pro Ser Cys Thr Leu Leu Glu Glu Ala Phe Arg Arg Tyr His Gly Tyr
65 70 75 80

Ile Phe Gly Phe Tyr Lys Trp His His Glu Pro Ala Glu Phe Gln Ala
85 90 95

Lys Thr Gln Val Gln Gln Leu Leu Val Ser Ile Thr Leu Gln Ser Glu
100 105 110

Cys Asp Ala Phe Pro Asn Ile Ser Ser Asp Glu Ser Tyr Thr Leu Leu
115 120 125

Val Lys Glu Pro Val Ala Val Leu Lys Ala Asn Arg Val Trp Gly Ala
130 135 140

Leu Arg Gly Leu Glu Thr Phe Ser Gln Leu Val Tyr Gln Asp Ser Tyr
145 150 155 160

Gly Thr Phe Thr Ile Asn Glu Ser Thr Ile Ile Asp Ser Pro Arg Phe
165 170 175

Ser His Arg Gly Ile Leu Ile Asp Thr Ser Arg His Tyr Leu Pro Val
180 185 190

Lys Ile Ile Leu Lys Thr Leu Asp Ala Met Ala Phe Asn Lys Phe Asn
195 200 205

Val Leu His Trp His Ile Val Asp Asp Gln Ser Phe Pro Tyr Gln Ser
210 215 220

Ile Thr Phe Pro Glu Leu Ser Asn Lys Gly Ser Tyr Ser Leu Ser His
225 230 235 240

Val Tyr Thr Pro Asn Asp Val Arg Met Val Ile Glu Tyr Ala Arg Leu
245 250 255

Arg Gly Ile Arg Val Leu Pro Glu Phe Asp Thr Pro Gly His Thr Leu
260 265 270

Ser Trp Gly Lys Gly Gln Lys Asp Leu Leu Thr Pro Cys Tyr Ser Gly
275 280 285

Ser Glu Pro Ser Gly Thr Phe Gly Pro Ile Asn Pro Thr Leu Asn Thr
290 295 300

Thr Tyr Ser Phe Leu Thr Thr Phe Phe Lys Glu Ile Ser Glu Val Phe
305 310 315 320

Pro Asp Gln Phe Ile His Leu Gly Gly Asp Glu Val Glu Phe Lys Cys
325 330 335

Trp Glu Ser Asn Pro Lys Ile Gln Asp Phe Met Arg Gln Lys Gly Phe
340 345 350

-continued

```
Gly Thr Asp Phe Lys Lys Leu Glu Ser Phe Tyr Ile Gln Lys Val Leu
        355                 360                 365

Asp Ile Ile Ala Thr Ile Asn Lys Gly Ser Ile Val Trp Gln Glu Val
    370                 375                 380

Phe Asp Asp Lys Ala Lys Leu Ala Pro Gly Thr Ile Val Glu Val Trp
385                 390                 395                 400

Lys Asp Ser Ala Tyr Pro Glu Glu Leu Ser Arg Val Thr Ala Ser Gly
                405                 410                 415

Phe Pro Val Ile Leu Ser Ala Pro Trp Tyr Leu Asn Arg Ile Ser Tyr
            420                 425                 430

Gly Gln Asp Trp Arg Lys Tyr Tyr Lys Val Glu Pro Leu Asp Phe Gly
        435                 440                 445

Gly Thr Gln Lys Gln Lys Gln Leu Phe Ile Gly Gly Glu Ala Cys Leu
    450                 455                 460

Trp Gly Glu Tyr Val Asp Ala Thr Asn Leu Thr Pro Arg Leu Trp Pro
465                 470                 475                 480

Arg Ala Ser Ala Val Gly Glu Arg Leu Trp Ser Ser Lys Asp Val Arg
                485                 490                 495

Asp Met Asp Asp Ala Tyr Asp Arg Leu Thr Arg His Arg Cys Arg Met
            500                 505                 510

Val Glu Arg Gly Ile Ala Ala Gln Pro Leu Tyr Ala Gly Tyr Cys Asn
        515                 520                 525

His Glu Asn Met
    530
```

<210> SEQ ID NO 26
<211> LENGTH: 4083
<212> TYPE: DNA
<213> ORGANISM: Artificial
<220> FEATURE:
<223> OTHER INFORMATION: CMV-modHEXB expression cassette

<400> SEQUENCE: 26

```
ttggccactc cctctatgcg cactcgctcg ctcggtgggg cctggcgacc aaaggtcgcc     60

agacggacgt gctttgcacg tccggcccca ccgagcgagc gagtgcgcat agagggagtg    120

gccaactcca tcactagagg tatggcagtg acgtaacgcg aagcgcgcga agcgagacca    180

tgaattatcc tgctgatgaa gcagaacaac tttaacgccg tgcgctgttc gcattatccg    240

aaccatccgc tgtggtacac gctgtgcgac cgctacggcc tgtatgtggt ggatgaagcc    300

aatattgaaa cccacggcat ggtgccaatg aatcgtctga ccgatgatcc gcgctggcta    360

ccggcgatga gcgaacgcgt actagttatt aatagtaatc aattacgggg tcattagttc    420

atagcccata tatggagttc cgcgttacat aacttacggt aaatggcccg cctggctgac    480

cgcccaacga cccccgccca ttgacgtcaa taatgacgta tgttcccata gtaacgccaa    540

tagggacttt ccattgacgt caatgggtgg agtatttacg gtaaactgcc cacttggcag    600

tacatcaagt gtatcatatg ccaagtacgc cccctattga cgtcaatgac ggtaaatggc    660

ccgcctggca ttatgcccag tacatgacct tatgggactt tcctacttgg cagtacatct    720

acgtattagt catcgctatt accatggtga tgcggttttg gcagtacatc aatgggcgtg    780

gatagcggtt tgactcacgg ggatttccaa gtctccaccc cattgacgtc aatgggagtt    840

tgttttggca ccaaaatcaa cgggactttc caaaatgtcg taacaactcc gccccattga    900

cgcaaatggg cggtaggcgt gtacggtggg aggtctatat aagcagagct cgtttagtga    960
```

```
accgtcagat cgcctggaga cgccatccac gctgttttga cctccataga agacaccggg   1020
accgatccag cctccgtacc ggttcgaaca ggtaagcgcc cctaaaatcc ctttgggcac   1080
aatgtgtcct gaggggagag gcagcgacct gtagatggga cgggggcact aaccctcagg   1140
tttggggctt ctgaatgtga gtatcgccat gtaagcccag tatttggcca atctcagaaa   1200
gctcctggtc cctggaggga tggagagaga aaaacaaaca gctcctggag cagggagagt   1260
gctggcctct tgctctccgg ctccctctgt tgccctctgg tttctcccca ggttcgaagc   1320
gcgcaattaa ccctcactaa agggaacaaa agctggagct caatcgattg aattccccgg   1380
ggatcctcta gagtcgacct gcagccactg tgttggattc gagcaccatg ctgctggcgc   1440
tgctgactca ggtggcgctg gtggtgcagg tggcggaggc ggctcgggcc ccgagcgtct   1500
cggccaagcc ggggccggcg ctgtggcccc tgccgctctc ggtgaagatg accccgaacc   1560
tgctgcatct cgccccggag aacttctaca tcagccacag ccccaattcc acggcgggcc   1620
cctcctgcac cctgctggag gaagcgtttc gacgatatca tggctatatt tttggtttct   1680
acaagtggca tcatgaacct gctgaattcc aggctaaaac ccaggttcag caacttcttg   1740
tctcaatcac ccttcagtca gagtgtgatg ctttccccaa catatcttca gatgagtctt   1800
atactttact tgtgaaagaa ccagtggctg tccttaaggc caacagagtt tggggagcat   1860
tacgaggttt agagaccttt agccagttag tttatcaaga ttcttatgga actttcacca   1920
tcaatgaatc caccattatt gattctccaa ggttttctca cagaggaatt ttgattgata   1980
catccagaca ttatctgcca gttaagatta ttcttaaaac tctggatgcc atggctttta   2040
ataagtttaa tgttcttcac tggcacatag ttgatgacca gtctttccca tatcagagca   2100
tcacttttcc tgagttaagc aataaaggaa gctattcttt gtctcatgtt tatacaccaa   2160
atgatgtccg tatggtgatt gaatatgcca gattacgagg aattcgagtc ctgccagaat   2220
ttgatacccc tgggcataca ctatcttggg gaaaaggtca gaaagacctc ctgactccat   2280
gttacagtgg gtctgagccc tctggcacct ttggacctat aaaccctact ctgaatacaa   2340
catacagctt ccttactaca tttttcaaag aaattagtga ggtgtttcca gatcaattca   2400
ttcatttggg aggagatgaa gtggaattta aatgttggga atcaaatcca aaaattcaag   2460
atttcatgag gcaaaaaggc tttggcacag attttaagaa actagaatct ttctacattc   2520
aaaaggtttt ggatattatt gcaaccataa acaagggatc cattgtctgg caggaggttt   2580
ttgatgataa agcaaagctt gcgccgggca caatagttga agtatggaaa gacagcgcat   2640
atcctgagga actcagtaga gtcacagcat ctggcttccc tgtaatcctt tctgctcctt   2700
ggtacttaaa taggattagc tatggacaag attggaggaa atactataaa gtggaacctc   2760
ttgattttgg cggtactcag aaacaaaaac aacttttcat tggtggagaa gcttgtctat   2820
ggggagaata tgtggatgca actaacctca ctccaagatt atggcctcgg gcaagtgctg   2880
ttggtgagag actctggagt tccaaagatg tcagagatat ggatgacgcc tatgacagac   2940
tgacaaggca ccgctgcagg atggtcgaac gtggaatagc tgcacaacct ctttatgctg   3000
gatattgtaa ccatgagaac atgtaagatc atcaagctta tcgataatca acctctggat   3060
tacaaaattt gtgaaagatt gactggtatt cttaactatg ttgctccttt tacgctatgt   3120
ggatacgctg ctttaatgcc tttgtatcat gctattgctt cccgtatggc tttcattttc   3180
tcctccttgt ataaatcctg gttgctgtct ctttatgagg agttgtggcc cgttgtcagg   3240
caacgtggcg tggtgtgcac tgtgtttgct gacgcaaccc ccactggttg gggcattgcc   3300
accacctgtc agctcctttc cgggactttc gctttccccc tccctattgc cacggcggaa   3360
```

```
ctcatcgccg cctgccttgc ccgctgctgg acaggggctc ggctgttggg cactgacaat   3420

tccgtggtgt tgtcggggaa atcatcgtcc tttccttggc tgctcgcctg tgttgccacc   3480

tggattctgc gcgggacgtc cttctgctac gtcccttcgg ccctcaatcc agcggacctt   3540

ccttcccgcg gcctgctgcc ggctctgcgg cctcttccgc gtcttcgcct tcgccctcag   3600

acgagtcgga tctccctttg ggccgcctcc ccgcatcgat accgtcgacc tcgaggcaag   3660

cttgggcccg gtacccaatt cgccctatag tgagtcgtat tacgcgcgca gcggccgacc   3720

atggcccaac ttgtttattg cagcttataa tggttacaaa taaagcaata gcatcacaaa   3780

tttcacaaat aaagcatttt tttcactgca ttctagttgt ggtttgtcca aactcatcaa   3840

tgtatcttat catgtctgga tctccggaca ctagataagc agcggcctgc ggcgcttgcg   3900

cttcgcggtt tacaactgct ggttaatatt taactctcgc catacctcta gtgatggagt   3960

tggccactcc ctctatgcgc actcgctcgc tcggtggggc ctggcgacca aaggtcgcca   4020

gacggacgtg ctttgcacgt ccggccccac cgagcgagcg agtgcgcata gagggagtgg   4080

cca                                                                 4083


<210> SEQ ID NO 27
<211> LENGTH: 1671
<212> TYPE: DNA
<213> ORGANISM: Homo sapiens
<220> FEATURE:
<221> NAME/KEY: CDS
<222> LOCATION: (1)..(1671)

<400> SEQUENCE: 27

atg gag ctg tgc ggg ctg ggg ctg ccc cgg ccg ccc atg ctg ctg gcg       48
Met Glu Leu Cys Gly Leu Gly Leu Pro Arg Pro Pro Met Leu Leu Ala
1               5                   10                  15

ctg ctg ttg gcg aca ctg ctg gcg gcg atg ttg gcg ctg ctg act cag       96
Leu Leu Leu Ala Thr Leu Leu Ala Ala Met Leu Ala Leu Leu Thr Gln
            20                  25                  30

gtg gcg ctg gtg gtg cag gtg gcg gag gcg gct cgg gcc ccg agc gtc      144
Val Ala Leu Val Val Gln Val Ala Glu Ala Ala Arg Ala Pro Ser Val
        35                  40                  45

tcg gcc aag ccg ggg ccg gcg ctg tgg ccc ctg ccg ctc tcg gtg aag      192
Ser Ala Lys Pro Gly Pro Ala Leu Trp Pro Leu Pro Leu Ser Val Lys
    50                  55                  60

atg acc ccg aac ctg ctg cat ctc gcc ccg gag aac ttc tac atc agc      240
Met Thr Pro Asn Leu Leu His Leu Ala Pro Glu Asn Phe Tyr Ile Ser
65                  70                  75                  80

cac agc ccc aat tcc acg gcg ggc ccc tcc tgc acc ctg ctg gag gaa      288
His Ser Pro Asn Ser Thr Ala Gly Pro Ser Cys Thr Leu Leu Glu Glu
                85                  90                  95

gcg ttt cga cga tat cat ggc tat att ttt ggt ttc tac aag tgg cat      336
Ala Phe Arg Arg Tyr His Gly Tyr Ile Phe Gly Phe Tyr Lys Trp His
            100                 105                 110

cat gaa cct gct gaa ttc cag gct aaa acc cag gtt cag caa ctt ctt      384
His Glu Pro Ala Glu Phe Gln Ala Lys Thr Gln Val Gln Gln Leu Leu
        115                 120                 125

gtc tca atc acc ctt cag tca gag tgt gat gct ttc ccc aac ata tct      432
Val Ser Ile Thr Leu Gln Ser Glu Cys Asp Ala Phe Pro Asn Ile Ser
    130                 135                 140

tca gat gag tct tat act tta ctt gtg aaa gaa cca gtg gct gtc ctt      480
Ser Asp Glu Ser Tyr Thr Leu Leu Val Lys Glu Pro Val Ala Val Leu
145                 150                 155                 160

aag gcc aac aga gtt tgg gga gca tta cga ggt tta gag acc ttt agc      528
```

-continued

```
Lys Ala Asn Arg Val Trp Gly Ala Leu Arg Gly Leu Glu Thr Phe Ser
                165                 170                 175

cag tta gtt tat caa gat tct tat gga act ttc acc atc aat gaa tcc      576
Gln Leu Val Tyr Gln Asp Ser Tyr Gly Thr Phe Thr Ile Asn Glu Ser
            180                 185                 190

acc att att gat tct cca agg ttt tct cac aga gga att ttg att gat      624
Thr Ile Ile Asp Ser Pro Arg Phe Ser His Arg Gly Ile Leu Ile Asp
        195                 200                 205

aca tcc aga cat tat ctg cca gtt aag att att ctt aaa act ctg gat      672
Thr Ser Arg His Tyr Leu Pro Val Lys Ile Ile Leu Lys Thr Leu Asp
    210                 215                 220

gcc atg gct ttt aat aag ttt aat gtt ctt cac tgg cac ata gtt gat      720
Ala Met Ala Phe Asn Lys Phe Asn Val Leu His Trp His Ile Val Asp
225                 230                 235                 240

gac cag tct ttc cca tat cag agc atc act ttt cct gag tta agc aat      768
Asp Gln Ser Phe Pro Tyr Gln Ser Ile Thr Phe Pro Glu Leu Ser Asn
                245                 250                 255

aaa gga agc tat tct ttg tct cat gtt tat aca cca aat gat gtc cgt      816
Lys Gly Ser Tyr Ser Leu Ser His Val Tyr Thr Pro Asn Asp Val Arg
            260                 265                 270

atg gtg att gaa tat gcc aga tta cga gga att cga gtc ctg cca gaa      864
Met Val Ile Glu Tyr Ala Arg Leu Arg Gly Ile Arg Val Leu Pro Glu
        275                 280                 285

ttt gat acc cct ggg cat aca cta tct tgg gga aaa ggt cag aaa gac      912
Phe Asp Thr Pro Gly His Thr Leu Ser Trp Gly Lys Gly Gln Lys Asp
    290                 295                 300

ctc ctg act cca tgt tac agt aga caa aac aag ttg gac tct ttt gga      960
Leu Leu Thr Pro Cys Tyr Ser Arg Gln Asn Lys Leu Asp Ser Phe Gly
305                 310                 315                 320

cct ata aac cct act ctg aat aca aca tac agc ttc ctt act aca ttt     1008
Pro Ile Asn Pro Thr Leu Asn Thr Thr Tyr Ser Phe Leu Thr Thr Phe
                325                 330                 335

ttc aaa gaa att agt gag gtg ttt cca gat caa ttc att cat ttg gga     1056
Phe Lys Glu Ile Ser Glu Val Phe Pro Asp Gln Phe Ile His Leu Gly
            340                 345                 350

gga gat gaa gtg gaa ttt aaa tgt tgg gaa tca aat cca aaa att caa     1104
Gly Asp Glu Val Glu Phe Lys Cys Trp Glu Ser Asn Pro Lys Ile Gln
        355                 360                 365

gat ttc atg agg caa aaa ggc ttt ggc aca gat ttt aag aaa cta gaa     1152
Asp Phe Met Arg Gln Lys Gly Phe Gly Thr Asp Phe Lys Lys Leu Glu
    370                 375                 380

tct ttc tac att caa aag gtt ttg gat att att gca acc ata aac aag     1200
Ser Phe Tyr Ile Gln Lys Val Leu Asp Ile Ile Ala Thr Ile Asn Lys
385                 390                 395                 400

gga tcc att gtc tgg cag gag gtt ttt gat gat aaa gca aag ctt gcg     1248
Gly Ser Ile Val Trp Gln Glu Val Phe Asp Asp Lys Ala Lys Leu Ala
                405                 410                 415

ccg ggc aca ata gtt gaa gta tgg aaa gac agc gca tat cct gag gaa     1296
Pro Gly Thr Ile Val Glu Val Trp Lys Asp Ser Ala Tyr Pro Glu Glu
            420                 425                 430

ctc agt aga gtc aca gca tct ggc ttc cct gta atc ctt tct gct cct     1344
Leu Ser Arg Val Thr Ala Ser Gly Phe Pro Val Ile Leu Ser Ala Pro
        435                 440                 445

tgg tac tta gat ttg att agc tat gga caa gat tgg agg aaa tac tat     1392
Trp Tyr Leu Asp Leu Ile Ser Tyr Gly Gln Asp Trp Arg Lys Tyr Tyr
    450                 455                 460

aaa gtg gaa cct ctt gat ttt ggc ggt act cag aaa cag aaa caa ctt     1440
Lys Val Glu Pro Leu Asp Phe Gly Gly Thr Gln Lys Gln Lys Gln Leu
465                 470                 475                 480
```

-continued

```
ttc att ggt gga gaa gct tgt cta tgg gga gaa tat gtg gat gca act      1488
Phe Ile Gly Gly Glu Ala Cys Leu Trp Gly Glu Tyr Val Asp Ala Thr
                485                 490                 495

aac ctc act cca aga tta tgg cct cgg gca agt gct gtt ggt gag aga      1536
Asn Leu Thr Pro Arg Leu Trp Pro Arg Ala Ser Ala Val Gly Glu Arg
            500                 505                 510

ctc tgg agt tcc aaa gat gtc aga gat atg gat gac gcc tat gac aga      1584
Leu Trp Ser Ser Lys Asp Val Arg Asp Met Asp Asp Ala Tyr Asp Arg
        515                 520                 525

ctg aca agg cac cgc tgc agg atg gtc gaa cgt gga ata gct gca caa      1632
Leu Thr Arg His Arg Cys Arg Met Val Glu Arg Gly Ile Ala Ala Gln
    530                 535                 540

cct ctt tat gct gga tat tgt aac cat gag aac atg taa                  1671
Pro Leu Tyr Ala Gly Tyr Cys Asn His Glu Asn Met
545                 550                 555


<210> SEQ ID NO 28
<211> LENGTH: 556
<212> TYPE: PRT
<213> ORGANISM: Homo sapiens

<400> SEQUENCE: 28

Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
            20                  25                  30

Val Ala Leu Val Val Gln Val Ala Glu Ala Ala Arg Ala Pro Ser Val
        35                  40                  45

Ser Ala Lys Pro Gly Pro Ala Leu Trp Pro Leu Pro Leu Ser Val Lys
    50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
            100                 105                 110

His Glu Pro Ala Glu Phe Gln Ala Lys Thr Gln Val Gln Gln Leu Leu
        115                 120                 125

Val Ser Ile Thr Leu Gln Ser Glu Cys Asp Ala Phe Pro Asn Ile Ser
    130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
            180                 185                 190

Thr Ile Ile Asp Ser Pro Arg Phe Ser His Arg Gly Ile Leu Ile Asp
        195                 200                 205

Thr Ser Arg His Tyr Leu Pro Val Lys Ile Ile Leu Lys Thr Leu Asp
    210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
            260                 265                 270
```

-continued

```
Met Val Ile Glu Tyr Ala Arg Leu Arg Gly Ile Arg Val Leu Pro Glu
        275                 280                 285

Phe Asp Thr Pro Gly His Thr Leu Ser Trp Gly Lys Gly Gln Lys Asp
    290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
            340                 345                 350

Gly Asp Glu Val Glu Phe Lys Cys Trp Glu Ser Asn Pro Lys Ile Gln
        355                 360                 365

Asp Phe Met Arg Gln Lys Gly Phe Gly Thr Asp Phe Lys Lys Leu Glu
    370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Asp Lys Ala Lys Leu Ala
                405                 410                 415

Pro Gly Thr Ile Val Glu Val Trp Lys Asp Ser Ala Tyr Pro Glu Glu
            420                 425                 430

Leu Ser Arg Val Thr Ala Ser Gly Phe Pro Val Ile Leu Ser Ala Pro
        435                 440                 445

Trp Tyr Leu Asp Leu Ile Ser Tyr Gly Gln Asp Trp Arg Lys Tyr Tyr
    450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
            500                 505                 510

Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
    530                 535                 540

Pro Leu Tyr Ala Gly Tyr Cys Asn His Glu Asn Met
545                 550                 555


<210> SEQ ID NO 29
<211> LENGTH: 7
<212> TYPE: PRT
<213> ORGANISM: Artificial
<220> FEATURE:
<223> OTHER INFORMATION: synthetic peptide

<400> SEQUENCE: 29

Gly Ser Glu Pro Ser Gly Thr
1               5
```

ADENO-ASSOCIATED VIRUS VIRION FOR TREATMENT OF TAY-SACHS DISEASE AND SANDHOFF DISEASE

RELATED APPLICATIONS

This application is a 371 application of PCT/JP2019/002428 having an international filing date of 25 Jan. 2019, which claims priority to JP2018-011705 filed 26 Jan. 2018, the entire content of each of which is incorporated herein by reference.

REFERENCE TO APPENDIX [CD ROM/SEQUENCE LISTING]

This application is being filed electronically via EFS-Web and includes an electronically submitted Sequence Listing in .txt format. The .txt file contains a sequence listing entitled "515488_5000004_Seq_Listing_ST25.txt" created on Nov. 26, 2023 and is 144.004 bytes in size. The sequence listing contained in this .txt file is part of the specification and hereby incorporated by reference in its entirety.

TECHNICAL FIELD

The present invention relates to a novel adeno-associated virus virion for treatment of Tay-Sachs disease and Sandhoff disease.

BACKGROUND ART

Tay-Sachs disease and Sandhoff disease both cause cranial nerve symptoms resulting from GM2 ganglioside accumulated in the central nervous system cells due to lowered activity of β-hexosaminidase A (Hex A). Hex A is a heterodimer composed of the α-subunit and the β-subunit, and it has enzymatic activity of degrading GM2 ganglioside. Tay-Sachs disease is a deficiency of Hex A caused by α-subunit deficiency, and Sandhoff disease is a deficiency of Hex A caused by β-subunit deficiency.

In the past, the present inventors prepared an expression vector comprising genes encoding the α-subunit and the β-subunit (HEXA cDNA and HEXB cDNA) inserted thereinto, introduced the resulting expression vector into CHO cell lines or particular yeast strains, and established cell lines that would constitutively express wild-type recombinant Hex A. They administered the wild-type recombinant Hex A produced in the manner described above to Sandhoff disease mouse models, observed a reduction in the amount of GM2 ganglioside accumulated in the cranial nervous system and an improvement in nerve symptoms, and confirmed efficacy of enzyme replacement therapy on Sandhoff disease and Tay-Sachs disease (Patent Literature 1 and Non-Patent Literature 1).

In order to resolve side effects caused upon administration of wild-type recombinant Hex A to patients with Tay-Sachs disease or Sandhoff disease, in addition, the present inventors prepared a modified β-subunit in which the β-subunit active site had been substituted with the α-subunit active site based on conformational information of the α-subunit and the β-subunit of β-hexosaminidase. They prepared a homodimeric modified β-hexosaminidase B comprising the modified β-subunit as a constituent (hereafter, referred to as "ModB") and confirmed that the recombinase had activity of degrading GM2 ganglioside (Patent Literature 2 and Non-Patent Literature 2).

In addition, the present inventors found a problem such that ModB would be easily degraded by a protease in the patient's body. In order to overcome this problem, the present inventors altered the structure of the protease recognition site of ModB so as to make ModB to be uninfluenced or less likely to be influenced by protease-induced hydrolysis. Thus, modified ModB having protease resistance was developed (hereafter, referred to as "Mod2B") (Patent Literature 3). Meanwhile, Patent Literature 4 discloses an adeno-associated virus virion for gene transfer into the nervous system cell.

PRIOR ART LITERATURES

Patent Literatures

[Patent Literature 1] JP 2002-369692 A
[Patent Literature 2] WO 2010/082622
[Patent Literature 3] WO 2014/061735
[Patent Literature 4] WO 2012/057363

Non-Patent Literatures

[Non-Patent Literature 1] Tsuji D et al., Ann. Neurol., April 2011, 69 (4): 691-701

[Non-Patent Literature 2] Matsuoka K et al., Mol. Ther., June 2011, 19 (6): 1017-1024

SUMMARY OF THE INVENTION

[Objects to be Attained by the Invention]

A modified β-subunit of human β-hexosaminidase, such as Mod2B described in Patent Literature 3, is administered to a patient in the form of a protein. Thus, Sandhoff disease and Tay-Sachs disease can be effectively treated.

For treatment of Sandhoff disease and Tay-Sachs disease, however, it is necessary that a modified β-subunit be constantly present in the patient's body. When administering a modified β-subunit to a patient in the form of a protein, accordingly, administration needs to be performed frequently, and stress imposed on the patient becomes increased.

[Means for Attaining the Objects]

The present inventors have conducted concentrated studies in order to provide a means for allowing a modified β-subunit to be constantly present in the body of the patient of Sandhoff disease and Tay-Sachs disease. This has led to the completion of the present invention described below. The present invention includes the following.

(1) A recombinant adeno-associated virus virion comprising: a capsomere comprising a protein capable of forming a virus virion; and a polynucleotide packaged in the capsomere comprising a promoter sequence and nucleotide sequences operably linked to the promoter sequence encoding a first amino acid sequence derived from the amino acid sequence of the β-subunit of wild-type human β-hexosaminidase composed of amino acids 55 to 556 in the sequence as shown in SEQ ID NO: 28 by substitution of amino acids 312 to 318 with glycine, serine, glutamic acid, proline, serine, glycine, and threonine in that order (SEQ ID NO: 29) and a second amino acid sequence, which is an amino acid sequence of a signal peptide linked to the N terminus of the first amino acid.

(2) The virus virion according to (1), wherein the first amino acid sequence further involves substitution of amino acid 452 with asparagine and/or amino acid 453 with arginine in the amino acid sequence composed of amino acids 55 to 556 in the sequence as shown in SEQ ID NO: 28.

(3) The virus virion according to (2), wherein the first amino acid sequence comprises any of the amino acid sequences selected from (A) to (C):

(A) the amino acid sequence composed of amino acids 31 to 532 in the sequence as shown in SEQ ID NO: 25;

(B) an amino acid sequence derived from the amino acid sequence composed of amino acids 31 to 532 in the sequence as shown in SEQ ID NO: 25 by deletion, substitution, or addition of 1 to several amino acids other than the amino acids at the sites of substitution, wherein a protein comprising the amino acid sequence has an activity derived from the wild-type human β-hexosaminidase α-subunit and protease resistance; and (C) an amino acid sequence having at least 90% identity to the amino acid sequence composed of amino acids 31 to 532 in the sequence as shown in SEQ ID NO: 25, wherein a protein comprising the amino acid sequence has an activity derived from the wild-type human β-hexosaminidase α-subunit and protease resistance, provided that the amino acids at the site of substitution are identical to those in the amino acid sequence as shown in SEQ ID NO: 25.

(4) The virus virion according to any of (1) to (3), wherein the second amino acid sequence is the amino acid sequence composed of amino acids 1 to 30 in the sequence as shown in SEQ ID NO: 25 or the amino acid sequence composed of amino acids 1 to 54 in the sequence as shown in SEQ ID NO: 28.

(5) The virus virion according to any of (1) to (4), wherein the 5' terminus and the 3' terminus of the polynucleotide comprise the 5' terminal inverted terminal repeat (ITR) sequence and the 3' terminal inverted terminal repeat (ITR) sequence derived from AAV1, AAV2, AAV3, or AAV4.

(6) The virus virion according to any of (1) to (5), wherein the 5' terminus and the 3' terminus of the polynucleotide comprise the nucleotide sequence as shown in SEQ ID NO: 13 and the nucleotide sequence as shown in SEQ ID NO: 14, respectively.

(7) The virus virion according to any of (1) to (6), wherein the promoter sequence is a systemic promoter or neural cell-specific promoter sequence.

(8) The virus virion according to (7), wherein the promoter sequence is a sequence of a systemic promoter selected from the group consisting of cytomegalovirus (CMV) promoter, EF-1α promoter, SV40 promoter, and CAG promoter.

(9) The virus virion according to (7), wherein the promoter sequence is a sequence of a neural cell-specific promoter selected from the group consisting of Synapsin I promoter sequence, myelin basic protein promoter sequence, neuron-specific enolase promoter sequence, calcium/calmodulin-dependent protein kinase II (CMKII) promoter, tubulin αI promoter, platelet-derived growth factor β strand promoter, glial fibrillary acidic protein (GFAP) promoter sequence, L7 promoter sequence (cerebellar Purkinje cell-specific promoter), and glutamate receptor delta-2 promoter (cerebellar Purkinje cell-specific promoter).

(10) The virus virion according to any of (1) to (9), wherein the protein capable of forming a virus virion comprises an amino acid sequence having 90% or higher identity to the amino acid sequence of the VP1 capsid protein derived from the type 1, type 2, type 3, type 9, type rh10, type PHP.B, or type PHP.eB adeno-associated virus or an amino acid sequence derived from the amino acid sequence having 90% or higher identity to the amino acid sequence of the VP1 capsid protein by substitution of at least 1 surface-exposed tyrosine residue with another amino acid residue.

(11) The virus virion according to any of (1) to (10), wherein the protein capable of forming a virus virion comprises an amino acid sequence derived from the amino acid sequence having 90% or higher identity to the amino acid sequence as shown in SEQ ID NO: 2, 4, or 6 by substitution of at least 1 surface-exposed tyrosine residue with another amino acid residue.

(12) The virus virion according to (11), wherein the protein capable of forming a virus virion comprises an amino acid sequence derived from the amino acid sequence as shown in SEQ ID NO: 2, 4, or 6 by substitution of at least tyrosine 445, tyrosine 444, or tyrosine 446, respectively.

(13) The virus virion according to any of (10) to (12), wherein the tyrosine residue is substituted with a phenylalanine residue.

(14) The virus virion according to any of (1) to (13), wherein the protein capable of forming a virus virion comprises the amino acid sequence as shown in SEQ ID NO: 8, 10, or 12 or an amino acid sequence derived from the amino acid sequence as shown in SEQ ID NO: 8, 10, or 12 by deletion, substitution, insertion, and/or addition of 1 to several amino acids other than the amino acids 444 to 446 and is capable of forming a virus virion.

(15) A pharmaceutical composition comprising the virus virion according to any of (1) to (14).

(16) The pharmaceutical composition according to (15), which is used for treatment of Tay-Sachs disease and/or Sandhoff disease.

(17) A method for treatment of Tay-Sachs disease and/or Sandhoff disease comprising administering the virus virion according to any of (1) to (14) to a patient who is in need of treatment of Tay-Sachs disease and/or Sandhoff disease.

(18) The method according to (17), which comprises administering the virus virion to the patient peripherally, intracerebrally, or intraspinally.

(19) The method according to (17), wherein the patient is a fetus in the maternal body and the virus virion is administered peripherally to the maternal body.

(20) The virus virion according to any of (1) to (14) used for treatment of Tay-Sachs disease and/or Sandhoff disease.

(21) The virus virion according to (20), which is administered peripherally, intracerebrally, or intraspinally to a patient who is in need of treatment of Tay-Sachs disease and/or Sandhoff disease.

(22) The virus virion according to (20), wherein the patient who is in need of treatment of Tay-Sachs disease and/or Sandhoff disease is a fetus in the maternal body and the virus virion is administered peripherally to the maternal body.

(23) Use of the virus virion according to any of (1) to (14) for production of a medicine used for treatment of Tay-Sachs disease and/or Sandhoff disease.

(24) The use according to (23), wherein the medicine is administered peripherally, intracerebrally, or intraspinally to a patient who is in need of treatment of Tay-Sachs disease and/or Sandhoff disease.

(25) The use according to (24), wherein the patient who is in need of treatment of Tay-Sachs disease and/or Sandhoff disease is a fetus in the maternal body and the medicine is administered peripherally to the maternal body.

This description includes part or all of the content as disclosed in the description and/or drawings of Japanese Patent Application No. 2018-011705, which is a priority document of the present application.

[Effects of the Invention]

The recombinant adeno-associated virus virion of the present invention is effective as a vector for introduction of a gene encoding the modified β-subunit of wild-type human β-hexosaminidase into the patient's body.

A pharmaceutical composition comprising the recombinant adeno-associated virus virion of the present invention can be used for treatment of Sandhoff disease and Tay-Sachs disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13B shows specific activity of Hex activity (MUG-degrading activity) in each organ 10 weeks after single administration of AAV-CMV-modHEXB at $1.15\times10^{10}$ vg/mouse to the brain ventricle or the temporal vein of Sandhoff disease heterozygous (Hexb+/−) newborn (P0 to P2) mice.

EMBODIMENTS OF THE INVENTION

1. Human β-Hexosaminidase Modified β-Subunit

Figure 1:
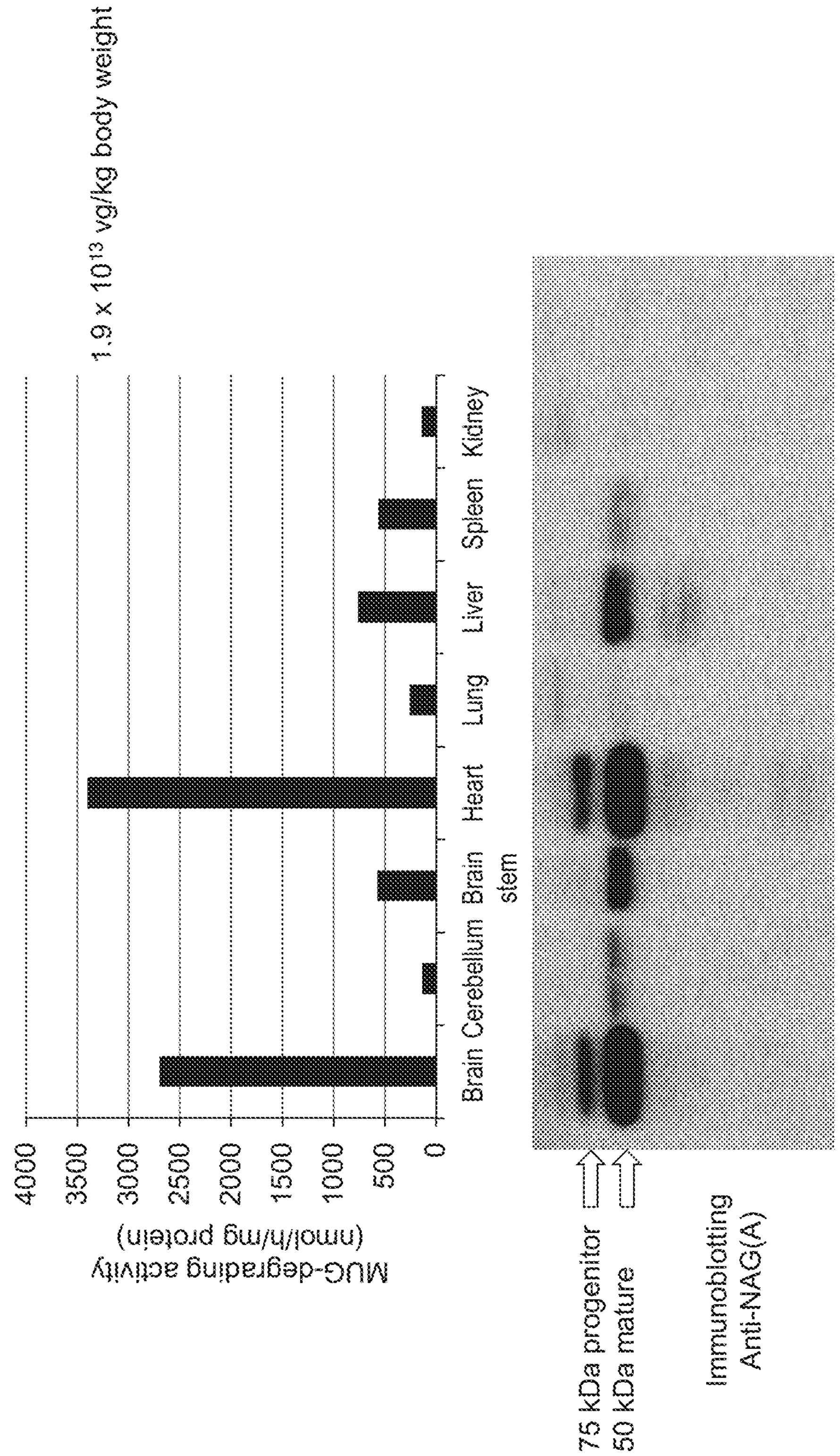
FIG. 1 shows the results of measurements of MUG-degrading specific activity in organ extracts performed in Example 1, Experiment 1.1 in the upper chart and the results of Western blot analysis of the proteins in organ extracts performed in Example 1, Experiment 1.2 in the lower image.

The wild-type human β-hexosaminidase β-subunit is expressed in the form of an immature protein comprising the amino acid sequence composed of amino acids 55 to 556 in the sequence as shown in SEQ ID NO: 28 and an amino acid sequence of a signal peptide linked to the N terminus thereof, and it functions as a mature protein upon removal of the signal peptide. An example of the amino acid sequence of the signal peptide of the wild-type human β-hexosaminidase β-subunit is the amino acid sequence composed of amino acids 1 to 54 in the sequence as shown in SEQ ID NO: 28. Specifically, the wild-type human β-hexosaminidase β-subunit comprises the amino acid sequence as shown in SEQ ID NO: 28 during the immature stage.

In the present invention, the protein comprising "the first amino acid sequence derived from the amino acid sequence composed of amino acids 55 to 556 in the sequence as shown in SEQ ID NO: 28 of the wild-type human β-hexosaminidase β-subunit by substitution of amino acids 312 to 318 with glycine, serine, glutamic acid, proline, serine, glycine, and threonine in that order" (hereafter, referred to as "the protein of the present invention" or "the modified β-subunit") is a recombinant protein that had acquired an activity derived from the wild-type human β-hexosaminidase α-subunit by altering the structure of the wild-type human β-hexosaminidase β-subunit active site and protease resistance by altering the structure of the protease recognition site of the wild-type human β-hexosaminidase β-subunit. The protein or the modified β-subunit of the present invention may be a mature protein consisting of the first amino acid sequence, or it may be an immature protein comprising the first amino acid sequence and the second amino acid sequence, which is an amino acid sequence of a signal peptide linked to the N terminus of the first amino acid sequence.

Examples of the second amino acid sequence, which is an amino acid sequence of a signal peptide linked to the N terminus of the first amino acid sequence, include the amino acid sequence composed of amino acids 1 to 30 in the sequence as shown in SEQ ID NO: 25 and the amino acid sequence composed of amino acids 1 to 54 in the sequence as shown in SEQ ID NO: 28.

When "activity derived from the α-subunit is acquired" in the present invention, at the β-subunit substrate binding site, the binding reactivity with the α-subunit substrate becomes relatively increased from the binding reactivity with the β-subunit substrate. Accordingly, a structural change concerning such properties is not limited to a structural change that makes the binding to the β-subunit substrate completely impossible. A structural change that would cause the protein that had the binding reactivity with the β-subunit substrate significantly higher than the binding reactivity with the α-subunit substrate to have a significantly increased binding reactivity with the α-subunit substrate is within the scope of the present invention. When "activity derived from the α-subunit is acquired," in particular, the protein preferably has the α-subunit substrate specificity. When the protein "has α-subunit substrate specificity," the active site structure (in particular, the position and the type of the amino acid residue that plays a key role in substrate binding reactivity) and the presence of the loop structure necessary for aggregation with (binding to) the GM2 activation factor are identical to those of the α-subunit.

When "protease resistance is acquired," the protein becomes uninfluenced or less likely to be influenced by protease-induced hydrolysis as a result of a structural change at the protease recognition site (i.e., the protein is not hydrolyzed or less likely to be hydrolyzed by a protease).

Protein structures concerning the properties described above can be changed in the manner described below.

The structure of the β-subunit active site can be changed to acquire the α-subunit-derived activity in accordance with the method described in detail in WO 2010/082622.

On the basis of the x-ray crystal structure information on human Hex A (the heterodimer of the α-subunit and the β-subunit) and Hex B (the homodimer of the β-subunit), specifically, an amino acid residue within an active pocket to recognize the GM2 ganglioside as a substrate and an amino acid residue associated with binding to the GM2 activator (that plays a role in association between the enzyme and its substrate; i.e., GM2 ganglioside) of the α-subunit are identified, and regions of the β-subunit molecules corresponding to the identified amino acid residues are substituted with the particular amino acid residues identified in the α-subunit. The term "corresponding regions" used herein refers to sites arranged in parallel when the amino acid sequences are aligned by inserting a gap into one of the sequences, according to need, so as to maximize the amino acid sequence identity between the α-subunit and the β-subunit. Amino acid sequence alignment can be performed with the use of a well-known method in the art, such as sequence analysis software (e.g., BLAST (Basic Local Alignment Search Tool at the National Center for Biological Information, U.S.A.) with default (initial) parameters.

Examples of sites in the β-subunit corresponding to amino acid residues in an active pocket of the α-subunit to recognize the GM2 ganglioside as a substrate include amino acid 452 and amino acid 453. Examples of amino acid residues associated with binding to the GM2 activator of the α-subunit in the β-subunit include amino acids 312 to 315.

In the protein of the present invention, amino acids 312 to 315 of the β-subunit may be substituted in order to acquire the α-subunit-derived activity. In the protein of the present invention, preferably, amino acids 312 to 315 and amino acid 452 and/or amino acid 453 of the β-subunit may be substituted in order to acquire the α-subunit-derived activity. In the protein of the present invention, more preferably, amino acids 312 to 315, amino acid 452, and amino acid 453 of the β-subunit may be substituted in order to acquire the α-subunit-derived activity.

The amino acids in the β-subunit can be substituted in accordance with corresponding amino acids in the α-subunit. Specifically, amino acids 312 to 315 are substituted with glycine, serine, glutamic acid, and proline in that order, amino acid 452 is substituted with asparagine, and amino acid 453 is substituted with arginine.

A structural change in the β-subunit active site aimed at acquisition of protease resistance can be performed by substitution of a protease recognition site in the β-subunit with a protease non-recognition site. The term "protease recognition site" used herein refers to an amino acid sequence that is hydrolyzed by a particular protease. In the present invention, the protease recognition site in the 1-subunit can be substituted with the protease non-recognition site by, for example, substituting a region of the α-subunit that is known to have protease resistance with a corresponding region of the β-subunit.

An example of amino acid residues in the β-subunit corresponding to the protease non-recognition site in the α-subunit is amino acids 312 to 318 in the β-subunit. In the protein of the present invention, at least amino acids 312 to 318 in the β-subunit may be substituted in order to acquire protease resistance.

The amino acids in the β-subunit can be substituted in accordance with corresponding amino acids in the α-subunit. Specifically, amino acids 312 to 315 are substituted with glycine, serine, glutamic acid, and proline in that order, and amino acids 316 to 318 are substituted with serine, glycine, and threonine in that order, as described above.

As a result of substitution of at least amino acids 312 to 318 in the β-subunit in the manner as described above, the resulting protein would become unrecognizable by a protease, and the protein becomes uninfluenced or less likely to be influenced by protease-induced hydrolysis.

Accordingly, the first amino acid sequence in the protein of the present invention is, for example, an amino acid sequence derived from the amino acid sequence composed of amino acids 55 to 556 in the sequence as shown in SEQ ID NO: 28 by substitution of amino acids 312 to 318 with glycine, serine, glutamic acid, proline, serine, glycine, and threonine in that order. In the first amino acid sequence in the protein of the present invention, in addition, amino acid 452 and/or amino acid 453 in the amino acid sequence composed of amino acids 55 to 556 in the sequence as shown in SEQ ID NO: 28 may be substituted with asparagine and arginine, respectively. Preferably, the first amino acid sequence in the protein of the present invention is an amino acid sequence derived from the amino acid sequence composed of amino acids 55 to 556 in the sequence as shown in SEQ ID NO: 28 by substitution of amino acids 312 to 318, amino acid 452, and amino acid 453 in the manner described above.

Information concerning the amino acid sequence of the β-subunit comprising the signal peptide of the wild-type human β-hexosaminidase (SEQ ID NO: 28) and that concerning the nucleotide sequence encoding such amino acid sequence (SEQ ID NO: 27) are available, for example, under "Accession number: NM 000512" and "Accession number: NM 000521" at the GenBank. Such information is registered under "Entry name: HEXB-HUMAN; Accession number: P07686" at Swiss-Prot (available on http://tw.expasy.org/uniprot/). The nucleotide sequence (cDNA) encoding the amino acid sequence of the β-subunit as shown in SEQ ID NO: 27 is a nucleotide sequence composed of nucleotides 118 to 1788 of a 1,919-bp nucleotide sequence available from the GenBank (Accession number: NM 000521). In the present invention, information concerning such amino acid sequences and nucleotide sequences can be used.

Specifically, the first amino acid sequence in the protein of the present invention is preferably any of (a) to (c) below:

(a) any of the amino acid sequences (i) to (iv) below:

(i) an amino acid sequence derived from the amino acid sequence composed of amino acids 55 to 556 in the sequence as shown in SEQ ID NO: 28 by substitution of amino acids 312 to 318 with glycine, serine, glutamic acid, proline, serine, glycine, and threonine in that order (SEQ ID NO: 29);

(ii) an amino acid sequence derived from the amino acid sequence composed of amino acids 55 to 556 in the sequence as shown in SEQ ID NO: 28 by substitution of amino acids 312 to 318 with glycine, serine, glutamic acid, proline, serine, glycine, and threonine in that order and substitution of amino acid 452 with asparagine;

(iii) an amino acid sequence derived from the amino acid sequence composed of amino acids 55 to 556 in the sequence as shown in SEQ ID NO: 28 by substitution of amino acids 312 to 318 with glycine, serine, glutamic acid, proline, serine, glycine, and threonine in that order and substitution of amino acid 453 with arginine; or (iv) an amino acid sequence derived from the amino acid sequence composed of amino acids 55 to 556 in the sequence as shown in SEQ ID NO: 28 by substitution of amino acids 312 to 318 with glycine, serine, glutamic acid, proline, serine, glycine, and threonine in that order, substitution of amino acid 452 with asparagine, and substitution of amino acid 453 with arginine;

(b) an amino acid sequence derived from any of the amino acid sequences (i) to (iv) above by deletion, substitution, or addition of 1 or several amino acids other than the amino acids at the sites of substitution above, wherein a protein comprising the amino acid sequence has an activity derived from the wild-type human β-hexosaminidase α-subunit and protease resistance; or (c) an amino acid sequence having at least 90% identity to any of the amino acid sequences (i) to (iv) above (it should be noted that the amino acids at the site of substitution are identical to those in the amino acid sequence as shown in SEQ ID NO: 25), wherein a protein comprising the amino acid sequence has an activity derived from the wild-type human β-hexosaminidase α-subunit and protease resistance.

As the amino acid sequence (a) above, the amino acid sequence (iv) is preferable among the amino acid sequences (i) to (iv) above. An example of such amino acid sequence is the amino acid sequence composed of amino acids 31 to 532 in the sequence as shown in SEQ ID NO: 25.

The amino acid sequence (b) above is not particularly limited, provided that it is derived from any of the amino acid sequences (i) to (iv) as defined in (a) above by deletion, substitution, or addition of 1 or several amino acids (for example, about 1 to 10, preferably about 1 to 5, more preferably 1 to 5, and most preferably 1 or 2 amino acids) other than the amino acids at the sites of substitution, and a protein comprising the amino acid sequence (b) has an activity derived from the α-subunit and protease resistance.

The activity derived from the α-subunit can be examined by, for example, allowing a target protein to be expressed in a mammalian-derived cell such as a CHO cell or human fibroblast, collecting the protein, and assaying 4-MUGS-degrading activity. Specifically, the protein (enzyme solution) is mixed with 4-methylumbelliferyl-6-sulfo-N-acetyl-β-D-glucosaminide (artificial substrate), these substances are subjected to the reaction at pH 4.5, and the amount of 4-methylumbelliferone that the unit amount of the enzyme solution can liberate per unit time is determined. Thus, activity of interest can be assayed. While 4-methylumbelliferone can be detected by any of various known methods, a method of detection involving the use of, for example, a fluorometer is preferable. A target protein may be incorporated into a known expression vector, the resulting vector may be introduced into a cell, and the target protein may be expressed therein.

Whether or not the target protein has protease resistance can be determined by, for example, allowing the target protein to be expressed in a mammalian-derived cell such as a CHO cell or human fibroblast, collecting the target protein, treating the collected target protein with a protease, subjecting the treated protein to a known protein detection method such as Western blotting, and detecting the presence or absence of a hydrolyzed form of the protein.

The amino acid sequence (c) above is not particularly limited, provided that it has at least 90% identity to any of the amino acid sequences (i) to (iv) as defined in (a) above, and a protein comprising the amino acid sequence (c) has an activity derived from the wild-type human β-hexosaminidase α-subunit and protease resistance (it should be noted that the amino acids at the site of substitution are identical to those in the amino acid sequence as shown in SEQ ID NO: 25). The term "identity" used herein refers to the percentage of identical and similar amino acid residues relative to all the overlapping amino acid residues in the 2 amino acid sequences optimally aligned with or without the introduction of gaps thereinto. Sequence identity can be determined by a method or with the use of sequence analysis software known to a person skilled in the art (e.g., BLAST (Basic Local Alignment Search Tool at the National Center for Biological Information, U.S.A.) at default parameters; i.e., initial parameters. When 2 sequences have "at least 90% identity," identity is 90% or higher, preferably 95% or higher, and more preferably 99% or higher. Whether or not the protein of interest has "activity derived from the α-subunit" and "protease resistance" can be determined in the manner described above.

When the first amino acid sequence is any of the amino acid sequences (a) to (c) above, the second amino acid sequence of the signal peptide is preferably the amino acid sequence composed of amino acids 1 to 30 in the sequence as shown in SEQ ID NO: 25 or the amino acid sequence composed of amino acids 1 to 54 in the sequence as shown in SEQ ID NO: 28, with the amino acid sequence composed of amino acids 1 to 30 in the sequence as shown in SEQ ID NO: 25 being particularly preferable.

When the protein of the present invention is expressed in the patient's body, it may exist in the form of a monomer (i.e., a modified (mutant) β-subunit) or in the form of a dimer of the mutant protein (i.e., a modified (mutant) human β-hexosaminidase B).

2. Nucleotide Sequence Encoding Amino Acid Sequence of Human β-Hexosaminidase Modified β-Subunit A polynucleotide in the recombinant adeno-associated virus virion of the present invention comprises nucleotide sequences encoding the first amino acid sequence and the second amino acid sequence. An example of the nucleotide sequence encoding the first amino acid sequence is the nucleotide sequence (a) or (b) below.

(a) Any of the nucleotide sequences (i) to (iv) below:

(i) a nucleotide sequence derived from the nucleotide sequence composed of nucleotides 163 to 1671 in the sequence as shown in SEQ ID NO: 27 by substitution of nucleotides 934 to 936, nucleotides 937 to 939, nucleotides 940 to 942, nucleotides 943 to 945, nucleotides 946 to 948, nucleotides 949 to 951, and nucleotides 952 to 954 with nucleotides indicating codons of glycine, serine, glutamic acid, proline, serine, glycine, and threonine in that order, respectively;

(ii) a nucleotide sequence derived from the nucleotide sequence composed of nucleotides 163 to 1671 in the sequence as shown in SEQ ID NO: 27 by substitution of nucleotides 934 to 936, nucleotides 937 to 939, nucleotides 940 to 942, nucleotides 943 to 945, nucleotides 946 to 948, nucleotides 949 to 951, and nucleotides 952 to 954 with nucleotides indicating codons of glycine, serine, glutamic acid, proline, serine, glycine, and threonine in that order and substitution of nucleotides 1354 to 1356 with nucleotides indicating a codon of asparagine, respectively;

(iii) a nucleotide sequence derived from the nucleotide sequence composed of nucleotides 163 to 1671 in the sequence as shown in SEQ ID NO: 27 by substitution of nucleotides 934 to 936, nucleotides 937 to 939, nucleotides 940 to 942, nucleotides 943 to 945, nucleotides 946 to 948, nucleotides 949 to 951, and nucleotides 952 to 954 with nucleotides indicating codons of glycine, serine, glutamic acid, proline, serine, glycine, and threonine in that order and substitution of nucleotides 1357 to 1359 with nucleotides indicating a codon of arginine, respectively; or (iv) a nucleotide sequence derived from the nucleotide sequence composed of nucleotides 163 to 1671 in the sequence as shown in SEQ ID NO: 27 by substitution of nucleotides 934 to 936, nucleotides 937 to 939, nucleotides 940 to 942, nucleotides 943 to 945, nucleotides 946 to 948, nucleotides 949 to 951, and nucleotides 952 to 954 with nucleotides indicating codons of glycine, serine, glutamic acid, proline, serine, glycine, and threonine in that order, substitution of nucleotides 1354 to 1356 with nucleotides indicating a codon of asparagine, and substitution of nucleotides 1357 to 1359 with nucleotides indicating a codon of arginine, respectively.

(b) A nucleotide sequence comprised in a DNA which hybridizes under stringent conditions to a DNA comprising a nucleotide sequence complementary to any of the nucleotide sequences (i) to (iv) above, which comprises nucleotides corresponding to the nucleotides at the sites of substitution that are identical to those at the sites of substitution, and encodes a protein having an activity derived from the wild-type human β-hexosaminidase α-subunit and having protease resistance.

In the present invention, a "codon" is not limited to a sequence of 3 nucleotides (a triplet) in the post-transcriptional RNA sequence, and a "codon" is also a sequence of 3 nucleotides in a DNA sequence. Accordingly, a codon in a DNA sequence is indicated with the use of thymine (T) instead of uracil (U).

The nucleotide sequence as shown in SEQ ID NO: 27 composed of 1,671 nucleotides encodes the β-subunit comprising a signal peptide of the wild-type human β-hexosaminidase (54 amino acids) (the β-subunit comprises the amino acid sequence of 556 amino acids in the sequence as shown in SEQ ID NO: 28). The nucleotide sequence composed of nucleotides 163 to 1671 in the sequence as shown in SEQ ID NO: 27 encodes a mature protein of the wild-type human β-hexosaminidase β-subunit (the mature protein comprises the amino acid sequence of 502 amino acids; i.e., amino acids 55 to 556, as shown in SEQ ID NO: 28).

As the nucleotide sequence (a) above, the nucleotide sequence (iv) is preferable among the nucleotide sequences (i) to (iv) above. An example of such nucleotide sequence is the nucleotide sequence composed of nucleotides 1518 to 3026 in the sequence as shown in SEQ ID NO: 26. The nucleotide sequence composed of nucleotides 1518 to 3026 in the sequence as shown in SEQ ID NO: 26 encodes the amino acid sequence composed of amino acids 31 to 532 in the sequence as shown in SEQ ID NO: 25.

A polynucleotide comprising a mutant nucleotide sequence as described above can be prepared by a known site-directed mutagenesis technique described in, for example, Molecular Cloning, A Laboratory Manual 2nd ed., Cold Spring Harbor Laboratory Press, 1989 and Current Protocols in Molecular Biology, John Wiley & Sons, 1987-1997, such as the Kunkel method, the Gapped duplex method, or PCR.

Concerning the nucleotide sequence (b) above, the "stringent conditions" are conditions of washing following hybridization. Under the "stringent conditions," salt concentration of the buffer is 15 to 330 mM and temperature is 25° C. to 65° C. Preferably, salt concentration is 15 to 150 mM and temperature is 45° C. to 55° C. Specifically, salt concentration is 80 mM and temperature is 50° C.

A nucleotide sequence of the DNA which hybridizes to the nucleotide sequence (a) above preferably has at least 40%, more preferably 60% or higher, further preferably 90% or higher, particularly preferably 95% or higher, and most preferably 99% or higher homology.

In the nucleotide sequence (b) above, nucleotides corresponding to the nucleotides at the sites of substitution are identical to the nucleotides at the sites of substitution. The "nucleotides corresponding to" the nucleotides at the sites of substitution are nucleotides (a triplet) positionally opposed to the nucleotides (a triplet) complementary to the nucleotides at the sites of substitution in a hybrid resulting from hybridization of DNA comprising the nucleotide sequence (b) to a complementary strand of DNA comprising the nucleotide sequence (a).

As the nucleotide sequence (b), a nucleotide that is not completely identical to the nucleotide sequence (a) but is completely identical to the post-translational amino acid sequence is particularly preferable (i.e., a nucleotide sequence derived from the nucleotide sequence (a) by silent mutation).

The polynucleotide in the recombinant adeno-associated virus virion of the present invention comprises a nucleotide sequence that is located adjacent to an upstream region of the nucleotide sequence encoding the first amino acid sequence, such as the nucleotide sequence (a) or (b), and encodes the second amino acid sequence of the signal peptide. Examples of the nucleotide sequences encoding the second amino acid sequence include the nucleotide sequence composed of nucleotides 1428 to 1517 in the sequence as shown in SEQ ID NO: 26 and the nucleotide sequence composed of nucleotides 1 to 162 in the sequence as shown in SEQ ID NO: 27. When the nucleotide sequence encoding the first amino acid sequence is the nucleotide sequence (a) or (b) above, the nucleotide sequence encoding the second amino acid sequence is preferably the nucleotide sequence composed of nucleotides 1428 to 1517 in the sequence as shown in SEQ ID NO: 26.

3. Recombinant Adeno-Associated Virus Virion

The recombinant adeno-associated virus virion of the present invention comprises: a capsomere comprising a protein capable of forming a virus virion; and a polynucleotide packaged in the capsomere comprising a promoter sequence and nucleotide sequences operably linked to the promoter sequence encoding the first amino acid sequence and the second amino acid sequence.

In the following description, the "nucleotide sequences encoding the first amino acid sequence and the second amino acid sequence" are occasionally referred to as "the target nucleotide sequences."

The polynucleotide comprising the promoter sequence and the target nucleotide sequence operably linked to the promoter sequence may be of the sense strand or antisense strand. Specifically, the polynucleotide comprising the promoter sequence and the target nucleotide sequence operably linked to the promoter sequence encompasses a polynucleotide complementary thereto.

The recombinant adeno-associated virus virion of the present invention (the rAAV virion) can penetrate the blood-brain barrier of an organism (e.g., the blood-brain barrier of an immature fetus and a newborn baby and the blood-brain barrier of a mature adult). The rAAV virion of the present invention can target neural cells in the brain, the spinal cord, and other organs of an adult via peripheral administration. The term "peripheral administration" used herein refers to the route of administration that a person skilled in the art generally recognizes as peripheral administration, such as intravenous, intraarterial, intraperitoneal, intracardiac, intramuscular, or intraumbilical vein administration (the intraumbilical vein administration may be applied when a fetus is the target). The rAAV virion of the present invention can also target neural cells via intracerebral or intraspinal administration. In the cells into which the rAAV virion of the present invention had been incorporated, the modified β-subunit of wild-type human β-hexosaminidase (modHexB) is expressed from the polynucleotide, modHexB is secreted from the cells, modHexB is transported to other cells through the bloodstream, and "cross-correction effects" exerted in such other cells are observed.

Hereafter, features of the recombinant adeno-associated virus virion of the present invention are described.

3.1 Adeno-Associated Virus (AAV)

The natural adeno-associated virus (AAV) is a nonpathogenic virus. Various recombinant virus vectors have been prepared with the utilization of such features and used to deliver genes of interest for gene therapy (see, for example, WO 2003/018821, WO 2003/053476, WO 2007/001010, and Journal of the Pharmaceutical Society of Japan, 126 (11), 1021-1028). The wild-type AAV genome is a single-stranded DNA molecule of an approximately 5-kb nucleotide length, and it is of a sense or antisense strand. In general, the AAV genome comprises inverted terminal repeat (ITR) sequences of approximately 145 nucleotide length at both the 5' and 3' terminuses of the genome. ITR is known to have a wide variety of functions, such as a function as a replication origin of the AAV genome and a packaging signal of the genome into the virion (see, for example, Journal of the Pharmaceutical Society of Japan, 126 (11), 1021-1028 as mentioned above). The internal region of the wild-type AAV genome flanked by ITRs (hereafter, referred to as the "internal region") comprises the AAV replication (rep) gene and the capsid (cap) gene. The rep gene and the cap gene each encode a protein Rep associated with virus replication and a capsid protein that forms a capsomere, which is an outer envelope of a regular icosahedron (e.g., at least one of VP1, VP2, and VP3). Detailed description is provided in, for example, Human Gene Therapy 13, pp. 345-354, 2002, Neuronal Development 45, pp. 92-103, 2001, Experimental Medicine 20, pp. 1296-1300, 2002, Journal of the Pharmaceutical Society of Japan 126 (11), 1021-1028, and Hum. Gene Ther., 16, 541-550, 2005.

Various types of natural adeno-associated viruses have been known, and each virus tends to infect different target cell (described in, for example, Gao, G, et al., Curr. Gene Ther., 5: 285-297, 2005, Xin, K-Q et al., J. Virol., 80: 11899-910, 2006, and Hellstroem, M, et al., Gene Ther., 16: 521-32, 2009). The rAAV vector of the present invention can be preferably prepared from, for example, natural adeno-associated virus type 1 (AAV1), type 2 (AAV2), type 3 (AAV3), type 4 (AAV4), type 5 (AAV5), type 6 (AAV6), type 7 (AAV7), type 8 (AAV8), or type 9 (AAV9), although the virus is not limited thereto. The nucleotide sequences of these adeno-associated virus genomes are known, and a reference can be made to the nucleotide sequences registered under GenBank Accession Numbers: AF063497.1 (AAV1), AF043303 (AAV2), NC_001729 (AAV3), NC_001829.1 (AAV4), NC_006152.1 (AAV5), AF028704.1 (AAV6), NC_006260.1 (AAV7), NC_006261.1 (AAV8), and AY530579 (AAV9). Among them, type 2, type 3, type 5, and type 9 are derived from humans. In the present invention, use of nucleotide sequences encoding capsid proteins derived from AAV1, AAV2, AAV9, AAV-rh10, AAV-PHP.B, and AAV-PHP.eB is particularly preferable. Among human-derived AAVs, AAV1 and AAV9 are reported to have relatively high efficiency for infection of neural cells (e.g., Taymans et al., Hum. Gene Ther., 18: 195-206, 2007). Also, AAV2 has already been used in clinical practice such as gene therapy of Parkinson's disease (e.g., Kaplitt et al., Lancet 369: 2097-2105, 2007, Marks et al., Lancet Neurol. 7: 400-408, 2008, Christine et al., Neurology 73: 1662-1669, 2009, Muramatsu et al., Mol. Ther., 18: 1731-1735, 2010).

3.2. Capsid Protein in the rAAV Virion of the Present Invention

The capsid protein in the rAAV virion of the present invention is preferably a VP1 capsid protein derived from AAV1, AAV2, AAV9, AAV-rh10, AAV-PHP.B, or AAV-PHP.eB, and more preferably a capsid protein comprising an amino acid sequence having 90% or higher identity to the amino acid sequence of the VP1 capsid protein derived from AAV1, AAV2, AAV9, AAV-rh10, AAV-PHP.B, or AAV-PHP.eB or an amino acid sequence derived from the amino acid sequence having 90% or higher identity to the amino acid sequence of the VP1 capsid protein derived from AAV1, AAV2, AAV9, AAV-rh10, AAV-PHP.B, or AAV-PHP.eB by substitution of at least one surface-exposed tyrosine residue (e.g., a tyrosine residue with the amino acid side chain being exposed to the virus virion surface) with another amino acid. The rAAV virion of the present invention comprising such capsid protein easily penetrates the blood-brain barrier of a fetus, a newborn baby, and an adult. According to a more preferable embodiment, the capsid protein in the rAAV virion of the present invention comprises an amino acid sequence derived from the VP1 amino acid sequence (e.g., SEQ ID NO: 2, 4, or 6) by substitution of at least one surface-exposed tyrosine residue (e.g., a tyrosine residue with the amino acid side chain being exposed to the virus virion surface) with another amino acid. An example of such protein comprises an amino acid sequence having sequence identity of approximately 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher to the amino acid sequence as shown in SEQ ID NO: 2, 4, or 6, with at least 1 surface-exposed tyrosine residue being substituted with another amino acid, and such protein is capable of forming a virus virion. In general, a higher sequence identity is more preferable. The capsid protein in the rAAV virion of the present invention forms a capsomere alone or in combination with another capsid protein member (e.g., VP2 and/or VP3), and the rAAV virion of the present invention comprising the AAV genome (or the AAV vector genome) packaged in the capsomere can be formed. Examples of amino acid residues that can be substituted with each other include other amino acid residues in the group of similar amino acid residues (described below). A modified capsid protein resulting from substitution with other amino acid residues can be prepared in accordance with a method known in the art, such as a common genetic engineering technique. Such genetic engineering technique is described in, for example, Molecular Cloning 3rd Edition, J. Sambrook et al., Cold Spring Harbor Lab. Press, 2001 and Current Protocols in Molecular Biology, John Wiley & Sons, 1987-1997.

The capsid protein in the rAAV virion of the present invention preferably comprises an amino acid sequence derived from the amino acid sequence as shown in SEQ ID NO: 2 by substitution of at least one surface-exposed tyrosine residue at position 252, 273, 445, 701, 705, or 731 with another amino acid, and such tyrosine residue is more preferably substituted with a phenylalanine residue. In the amino acid sequence as shown in SEQ ID NO: 2, tyrosine 445 is preferably substituted with phenylalanine. The capsid protein in the rAAV virion of the present invention preferably comprises an amino acid sequence derived from the amino acid sequence as shown in SEQ ID NO: 4 by substitution of at least one surface-exposed tyrosine residue at position 252, 272, 444, 500, 700, 704, or 730 with another amino acid, and such tyrosine residue is more preferably substituted with a phenylalanine residue. In the amino acid sequence as shown in SEQ ID NO: 4, tyrosine 444 is preferably substituted with phenylalanine. The capsid protein in the rAAV virion of the present invention preferably comprises an amino acid sequence derived from the amino acid sequence as shown in SEQ ID NO: 6 by substitution of at least one surface-exposed tyrosine residue at position 252, 274, 446, 701, 705, 706, or 731 with another amino acid, and such tyrosine residue is more preferably substituted with a phenylalanine residue. In the amino acid sequence as shown in SEQ ID NO: 6, tyrosine 446 is preferably substituted with phenylalanine. The capsomere of the rAAV virion of the present invention may comprise the protein by itself or such protein in combination with other members (VP2 and/or VP3). In the present invention, the amino acids to be substituted include amino acids at the corresponding positions in VP2 and VP3 of the relevant virus types. Preferably, a corresponding tyrosine residue is substituted with a phenylalanine residue. Such modified capsid protein can be prepared in accordance with a method known in the art, such as a common genetic engineering technique. Such genetic engineering technique is described in, for example, Molecular Cloning 3rd Edition. The virus virion of the present invention comprising such capsid protein can penetrate the blood-brain barrier of an adult and a fetus, as described above. Preferably, the virus virion comprising a functionally equivalent capsid protein can infect neural cells in the brain, the spinal cord, and other organs of an adult via peripheral administration. The term "the neural system" used in the present invention refers to an organ composed of neural tissue. In the present invention, neural cells into which the gene of interest is to be introduced include at least neurons contained in the central nervous system such as the brain or spinal cord, and such neural cells may further include neuroglia cells, microglia cells, astroglia cells, oligodendroglia cells, ependymal cells, and cerebrovascular endothelial cells. Among neural cells into which the gene of interest is to be introduced, the percentage of neurons is preferably 70% or more, 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more, or 100%.

According to another embodiment, the capsomere of the rAAV virion of the present invention comprises a protein comprising the amino acid sequence as shown in SEQ ID NO: 8, 10, or 12 or an amino acid sequence derived from the amino acid sequence as shown in SEQ ID NO: 8, 10, or 12 by deletion, substitution, insertion, and/or addition of 1 or more amino acids at positions other than amino acids 444 to 446 and capable of forming a virus virion. More specifically, the capsid protein in the rAAV virion of the present invention is enclosed in the capsomere of the rAAV virion of the present invention alone or in combination with another capsid protein member (e.g., VP2 and/or VP3), and the AAV genome (or the recombinant AAV vector genome) is packaged in the capsomere. Two or more of the deletion, substitution, insertion, and addition of amino acids may occur simultaneously. For example, such protein comprises the amino acid sequence as shown in SEQ ID NO: 8, 10, or 12 or an amino acid sequence derived from the amino acid sequence as shown in SEQ ID NO: 8, 10, or 12 by deletion, substitution, insertion, and/or addition of 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid at position(s) other than amino acids 444 to 446 and is capable of forming a virus virion. In general, a smaller number of amino acids subjected to deletion, substitution, insertion, and/or addition is preferable. The resulting rAAV virion of the present invention can penetrate the blood-brain barrier of an adult and a fetus as described above. Preferably, the virus virion can be introduced into neural cells in the brain, the spinal cord, and other organs via peripheral administration. Also, the rAAV virion of the present invention can be administered peripherally to the mother, so that it can be introduced into neural cells in the brain, the spinal cord, and other organs of a fetus in the maternal body. Such modified capsid protein can be prepared in accordance with a method known in the art, such as a common genetic engineering technique.

Examples of amino acids that can be substituted with each other in the protein (polypeptide) of the present invention are demonstrated below. Amino acids within the same group can be substituted with each other. Group A: leucine, isoleucine, norleucine, valine, norvaline, alanine, 2-aminobutyric acid, methionine, o-methylserine, t-butylglycine, t-butylalanine, and cyclohexylalanine; Group B: aspartic acid, glutamic acid, isoaspartic acid, isoglutamic acid, 2-aminoadipic acid, and 2-aminosuberic acid; Group C: asparagine and glutamine; Group D: lysine, arginine, ornithine, 2,4-diaminobutyric acid, and 2,3-diaminopropionic acid; Group E: proline, 3-hydroxyproline, and 4-hydroxyproline; Group F: serine, threonine, and homoserine; and Group G: phenylalanine and tyrosine.

The capsid proteins VP1, VP2, and/or VP3 contained in the rAAV virion of the present invention can be encoded by 1 or more types of polynucleotides. Preferably, all the capsid proteins in the present invention are encoded by a single polynucleotide. More preferably, the capsid protein is encoded by the polynucleotide as shown in SEQ ID NO: 7, 9, or 11.

The polynucleotide encoding the capsid protein contained in the rAAV virion of the present invention encodes a protein that is functionally equivalent to the capsid protein capable of forming the recombinant virus virion of the present invention. For example, such polynucleotide comprises the polynucleotide sequence as shown in SEQ ID NO: 7, 9, or 11 or a polynucleotide sequence derived from the polynucleotide sequence as shown in SEQ ID NO: 7, 9, or 11 by deletion, substitution, insertion, and/or addition of 1 or more nucleotides (e.g., 1 to 50, 1 to 40, 1 to 30, 1 to 25, 1 to 20, 1 to 15, 1 to 10, 1 to 9 (1 to several), 1 to 8, 1 to 7, 1 to 6, 1 to 5, 1 to 4, 1 to 3, 1 to 2, or 1) and encodes a protein comprising the amino acid sequence as shown in SEQ ID NO: 8, 10, or 12 or an amino acid sequence derived from the amino acid sequence as shown in SEQ ID NO: 8, 10, or 12 by deletion, substitution, insertion, and/or addition of 1 or more amino acids at positions other than amino acids 444 to 446 and capable of forming a virus virion. Two or more of the deletion, substitution, insertion, and addition of amino acids may occur simultaneously. The rAAV virion of the present invention comprising the capsid protein encoded by the polynucleotide can penetrate the blood-brain barrier of an adult and a fetus as described above. Preferably, the rAAV virion of the present invention can be introduced into neural cells in the brain, the spinal cord, and other organs of an adult via peripheral administration. Also, the rAAV virion of the present invention can be administered peripherally to the mother, so that it can be introduced into neural cells in the brain, the spinal cord, and other organs of a fetus in the maternal body. In general, a smaller number of such nucleotides subjected to deletion, substitution, insertion, and/or addition is preferable. For example, such polynucleotide can hybridize under stringent conditions to the polynucleotide as shown in SEQ ID NO: 7, 9, or 11 or a sequence complementary thereto and encodes a protein capable of forming the recombinant virus virion of the present invention (e.g., a protein comprising the amino acid sequence as shown in SEQ ID NO: 8, 10, or 12 or an amino acid sequence derived from the amino acid sequence as shown in SEQ ID NO: 8, 10, or 12 by deletion, substitution, insertion, and/or addition of 1 or more amino acids at positions other than amino acids 444 to 446).

Hybridization can be performed by a known method or a method in accordance therewith, such as a method described in Molecular Cloning 3rd Edition, J. Sambrook et al., Cold Spring Harbor Lab. Press, 2001. When using a commercially available library, hybridization can be performed in accordance with a method described in the manufacturer's instructions. The "stringent conditions" may by low-stringent conditions, moderately-stringent conditions, or high-stringent conditions. Under "low-stringent conditions," for example, hybridization is performed in the presence of 5×SSC, 5×Denhardt's Solution, 0.5% SDS, and 50% formamide at 32° C. Under "moderately-stringent conditions," for example, hybridization is performed in the presence of 5×SSC, 5×Denhardt's Solution, 0.5% SDS, and 50% formamide at 42° C. Under "high-stringent conditions," for example, hybridization is performed in the presence of 5×SSC, 5×Denhardt's Solution, 0.5% SDS, and 50% formamide at 50° C. Under such conditions, DNA exhibiting a higher degree of homology can be efficiently obtained as temperature is raised. A plurality of elements are considered to affect hybridization stringency, and examples of such elements include temperature, probe concentration, probe length, ion intensity, duration, and salt concentration. A person skilled in the art can select adequate elements to realize equivalent stringency.

Polynucleotides capable of hybridization has identity of, for example, 70% or higher, 80% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher to the nucleotide sequence as shown in SEQ ID NO: 7, 9, or 11, which is determined using homology search software such as FASTA or BLAST with default parameters. In general, a larger degree of homology is preferable.

Amino acid sequence and polynucleotide sequence identity can be determined using the algorithm BLAST by Carlin and Altur (Proc. Natl. Acad. Sci., U.S.A., 87: 2264-2268, 1990, Proc. Natl. Acad. Sci., U.S.A., 90: 5873, 1993). A program referred to as BLASTN or BLASTX based on the BLAST algorithm has been developed (Altschul S F, et al.: J. Mol. Biol., 215: 403, 1990). When analyzing the nucleotide sequence using BLASTN, the parameters are set to, for example, the score of 100 and the word length of 12. When analyzing the amino acid sequence using BLASTX, the parameters are set to, for example, the score of 50 and the word length of 3. When using the BLAST and Gapped BLAST programs, default parameters of both the programs are used.

The Rep protein used in the present invention needs to have, for example, a function of recognizing the ITR sequence and replicating the genome based on the sequence, a function of recruiting the wild-type AAV genome (or the rAAV genome) and packaging the same within the virus virion, and a function of forming the rAAV virion of the present invention. As long as the Rep protein has such known functions at equivalent levels, it may have the same degree of amino acid sequence identity, and the same number of amino acids may be subjected to deletion, substitution, insertion, and/or addition as described above. Functional equivalency is, for example, the specific activity described above. In the present invention, a protein comprising the amino acid sequence as shown in SEQ ID NO: 16 is preferably used.

The polynucleotide encoding the Rep protein used in the present invention needs to encode a Rep protein having a function of recognizing the ITR sequence and replicating the genome based on the sequence, a function of recruiting the wild-type AAV genome (or the rAAV genome) and packaging the same within the virus virion, and a function of forming the rAAV virion of the present invention. As long as the polynucleotide encodes the Rep protein having such known functions at equivalent levels, it may have the same degree of nucleotide sequence identity, and the same number of nucleotides may be subjected to deletion, substitution, insertion, and/or addition as described above. Functional equivalency is, for example, the specific activity described above. In the present invention, a polynucleotide comprising the nucleotide sequence as shown in SEQ ID NO: 15 is preferably used.

An embodiment of the present invention provides polynucleotides encoding the capsid protein, such as VP1, VP2, and/or VP3, and the Rep protein encoded by the internal region of the wild-type AAV genome in the form that are incorporated into the AAV helper plasmid. Polynucleotides encoding the capsid protein, such as VP1, VP2, and/or VP3, and the Rep protein used in the present invention may be incorporated in 1, 2, 3, or more types of plasmids, according to need. Polynucleotides encoding at least 1 of the capsid protein and the Rep protein may be incorporated into the AAV genome, according to need. In the present invention, all the capsid proteins (VP1, VP2, and/or VP3) and the Rep protein are preferably encoded by a single polynucleotide and provided in the form of the AAV helper plasmids. A reference may be made to the examples of the present invention below.

3.3. The rAAV Genome of the Present Invention

The recombinant adeno-associated virus polynucleotide packaged within the rAAV virion of the present invention (hereafter, referred to as "the rAAV genome of the present invention") can be prepared by substitution of a polynucleotide of the internal region flanked by the 5' ITR and the 3' ITR of the wild-type AAV genome (i.e., either or both the rep gene and the cap gene) with a gene cassette comprising a polynucleotide comprising the target nucleotide sequence (the gene for therapy) and a promoter sequence for transcription of the polynucleotide. Preferably, the 5' ITR and the 3' ITR are located at the 5' terminus and the 3' terminus of the AAV genome, respectively. The rAAV genome of the present invention preferably comprises the 5' ITR and the 3' ITR of the AAV1, AAV2, AAV3, or AAV9 genome as ITRs of the 5' terminus and the 3' terminus, more preferably the 5' ITR and the 3' ITR of the AAV3 genome, and particularly preferably the polynucleotide as shown in SEQ ID NO: 13 as the 5' ITR and the polynucleotide as shown in SEQ ID NO: 14 as the 3' ITR. In general, ITR has a structure in which a part thereof has been easily replaced with a complementary sequence (i.e., the flip-flop structure). Thus, the 5' ITR and the 3' ITR in the rAAV genome of the present invention may be in the opposite direction. In the rAAV genome of the present invention, the length of the gene cassette to be substituted with the internal region is preferably equivalent to the length of the original polynucleotide from the viewpoint of practical use. Specifically, the full-length of the rAAV genome of the present invention may be equivalent to the full-length of the wild-type; i.e., 5 kb. For example, the full-length is approximately 2 to 6 kb, and preferably approximately 4 to 6 kb.

In general, the virus genome packaged within the recombinant adeno-associated virus virion is single-stranded. This prolongs the time (several days) to express the target gene in the genome, disadvantageously. In order to overcome such problem, a gene for therapy to be introduced is designed to be self-complementary (referred to as the self-complementary (sc) vector) so as to promote expression after virus vector infection. In this case, an inverted sequence is necessary to form a double strand. To this end, the length of the therapeutic gene should be designed to be an approximately half the length of the non-sc genome vector. When the recombinant virus genome is the sc type, more specifically, the length of the target gene that can be incorporated is approximately 2 kb including a region necessary for a promoter, polyadenylation, and the like. Such design is described in detail in, for example, Foust K D, et al., Nat. Biotechnol., Jan 2009; 27 (1): 59-65, and Non-Patent Literature 3 as mentioned above. The rAAV genome used in the present invention may or may not be of an sc type. In the case of an sc type, the entire or a part of the expression cassette comprising the target nucleotide sequence can form double-stranded DNA.

In order to express a target modHexB polypeptide in the rAAV genome of the present invention, the target nucleotide sequence is operably linked to various types of known promoter sequences. A promoter sequence may be a tissue-non-specific systemic promoter (i.e., the ubiquitous promoter) or it may be a tissue-specific promoter. Since target modHexB is to be expressed in neural cells, a neural cell-specific promoter can be used as a tissue-specific promoter. It should be noted that the present inventors had discovered that higher therapeutic effects can be attained with the use of the systemic promoter, compared with the use of the neural cell-specific promoter.

A preferable systemic promoter is selected from the group consisting of cytomegalovirus (CMV) promoter, EF-1α promoter, SV40 promoter, and CAG promoter.

Neural-cell-specific promoter sequences used in the present invention are derived from, for example, neurons, neuroglia cells, oligodendroglia cells, cerebrovascular endothelial cells, microglia cells, or ventricular epidermal cells, although cells are not limited thereto. A preferable neural cell-specific promoter is selected from the group consisting of Synapsin I promoter sequence, myelin basic protein promoter sequence, neuron-specific enolase promoter sequence, calcium/calmodulin-dependent protein kinase II (CMKII) promoter, tubulin αI promoter, platelet-derived growth factor β strand promoter, glial fibrillary acidic protein (GFAP) promoter sequence, L7 promoter sequence (cerebellar Purkinje cell-specific promoter), and glutamate receptor delta-2 promoter (cerebellar Purkinje cell-specific promoter).

Concerning the rAAV virion of the present invention, a promoter sequence, such as calcium/calmodulin-dependent protein kinase II (CMKII) promoter, tubulin αI promoter, or platelet-derived growth factor β strand promoter, can be used. One of such promoter sequences may be used alone or a plurality of such promoter sequences may be used in combination.

A systemic promoter is particularly preferable, and CMV promoter is the most preferable.

The rAAV genome of the present invention may further comprise a known sequence, such as an enhancer sequence that assists mRNA transcription and translation into a protein, the Kozak sequence, and an adequate polyadenylation signal sequence.

The terms "virus virion," "virus vector," and "virus particle" used herein are used interchangeably, unless otherwise specified.

The term "polynucleotide" used herein is used interchangeably with the term "nucleic acid," "gene," or "nucleic acid molecule," and the term refers to a nucleotide polymer. The term "nucleotide sequence" used herein is used interchangeably with the term "nucleic acid sequence" or "nucleotide sequence," and it is indicated as a deoxyribonucleotide (abbreviated to as A, G, C, and T) sequence. For example, the term "a polynucleotide comprising the nucleotide sequence as shown in SEQ ID NO: 1 or a fragment thereof" refers to a polynucleotide comprising a sequence indicated by deoxynucleotides A, G, C, and/or T as shown in SEQ ID NO: 1 or a fragment thereof.

The "virus genome" or the "polynucleotide" of the present invention can be present in the form of DNA (e.g., cDNA or genome DNA). It may be in the form of RNA (e.g., mRNA), according to need. The virus genome and the polynucleotide used herein can be double-stranded or single-stranded DNA. Single-stranded DNA or RNA may be a coding strand (known as a sense strand) or a non-coding strand (known as an antisense strand). When the positions of the promoter encoded by the rAAV genome, the target gene, and the polyadenylation signal in the gene sequence are described herein, the rAAV genome of the sense strand is described concerning the sense strand, and the rAAV genome of the antisense strand is described concerning the complementary strand of the antisense strand, unless otherwise specified.

The terms "protein" and "polypeptide" are used interchangeably herein, and the terms indicate an amino acid polymer. In the polypeptide used herein, the left end is the N terminus (the amino terminus) and the right end is the C terminus (the carboxyl terminus) in accordance with a common practice of peptide description. A partial peptide in the polypeptide of the present invention (it may be referred to as the partial peptide of the present invention herein) is a partial peptide in the polypeptide of the present invention described above, and it preferably has properties similar to those of the polypeptide of the present invention.

The term "plasmid" used herein refers to a variety of known gene elements, such as a plasmid, phage, transposon, cosmid, or chromosome. A plasmid can replicate in a particular host and it can transport a gene sequence between cells. A plasmid comprises a variety of know nucleotides (DNA, RNA, PNA, and a mixture thereof) herein, and it may be single-stranded or double-stranded, with a double-stranded plasmid being preferable. For example, the term "rAAV vector plasmid" used herein is intended to comprise a double strand formed of the rAAV vector genome and a complementary strand thereof, unless otherwise specified. A plasmid used in the present invention may be linear or cyclic.

The target nucleotide sequence incorporated into the rAAV genome of the present invention is delivered to a neural cell and incorporated into the genome of the cell with higher efficiency, compared with a conventional technique. Use of the rAAV vector of the present invention enables gene introduction into the number of neural cells that is approximately 10, 20, 30, 40, or 50 times or larger, compared with the use of the conventional rAAV vector. The number of neural cells into which the gene of interest had been introduced can be determined by, for example, preparing a rAAV virion packaging the rAAV vector genome comprising an arbitrary marker gene integrated therein, administering the rAAV virion to a test animal, and counting the number of neural cells expressing the marker gene (or the marker protein) integrated into the rAAV vector genome. A known marker gene can be used. Examples of marker genes include LacZ gene, green fluorescent protein (GFP) gene, and luminescent protein gene (e.g., firefly luciferase).

In the present invention, the rAAV virion comprising the rAAV vector genome packaged therein can penetrate the blood-brain barrier of an organism. Through peripheral administration to a subject, accordingly, the target therapeutic gene can be introduced into neural cells of the brain, the spinal cord, and other organs of the subject.

The term "packaging" used herein refers to events including preparation of the single-stranded virus genome, assembly of a coat protein (capsid), and inclusion of the virus genome in a capsid (encapsidation). When an adequate plasmid vector (a plurality of plasmids, in general) is introduced into a cell line capable of packaging under adequate conditions, recombinant virus particles (i.e., virus virions or virus vectors) are assembled, and the resultant is secreted in the culture.

4. Preparation of the rAAV Virion of the Present Invention

Another aspect of the present invention provides a method for preparing the rAAV virion of the present invention. This method can comprise a step of transfecting (a) and (b) below to a cultured cell: (a) a first polynucleotide encoding the capsid protein of the present invention (generally referred to as the "AAV helper plasmid"); and (b) a second polynucleotide to be packaged in the rAAV virion of the present invention (that comprises the target nucleotide sequence). The method of preparation according to the present invention can comprise: (c) a step of transfecting a plasmid that encodes an adenovirus-derived factor referred to as the "adenovirus (AdV) helper plasmid" to a cultured cell or a step of infecting the cultured cell with adenovirus. The method of preparation according to the present invention can further comprise a step of culturing the transfected cultured cells and a step of recovering the recombinant adeno-associated virus vector from the culture supernatant. Such methods are known and used in the examples herein.

The method for preparing the rAAV virion of the present invention preferably comprises transfecting the polynucleotides (a) and (b) to a cultured cell: (a) a first polynucleotide encoding a protein comprising the amino acid sequence selected from the group consisting of SEQ ID NO: 8, 10 and 12; and (b) a second polynucleotide comprising the promoter sequence and the target nucleotide sequence between the nucleotide sequence as shown in SEQ ID NO: 13 and the nucleotide sequence as shown in SEQ ID NO: 14. An example of such first polynucleotide and second polynucleotide is a combination of polynucleotides described in Example 3.

In the first polynucleotide, it is preferable that a nucleotide encoding the capsid protein of the present invention be operably linked to a known promoter sequence that can function in a cultured cell. As such promoter sequence, for example, cytomegalovirus (CMV) promoter, EF-1α promoter, or SV40 promoter can be adequately used. In addition, the first polynucleotide can adequately comprise, for example, a known enhancer sequence, a Kozak sequence, or a poly A addition signal sequence.

For example, the first polynucleotide encoding a protein comprising an amino acid sequence selected from the group consisting of SEQ ID NOs: 8, 10 and 12 can be prepared by the method described below. Concerning 3 types of AAVs; i.e., type 1 AAV (AAV1), type 2 AAV (AAV2), and type 9 AAV (AAV9), pAAV1-RC, pAAV2-RC, and pAAV9-RC plasmids each comprising a nucleotide sequence encoding the relevant coat protein VP1 are used as templates. These plasmids are derived from AAV3 Rep/VP described in the literature (Handa et. al., J. Gen. Virol., 81: 2077-2084, 2000) and comprise the Rep sequence of AAV3 (Muramatsu et al., Virology 221, 208-217, 1996). The nucleotide sequences of VP1 of such AAVs have already been registered under Accession Nos. AF063497, AF043303, and AY530579 at GenBank (as shown in SEQ ID NOs: 1, 3 and 5). A forward primer, which is DNA comprising SEQ ID NO: 17, and a reverse primer, which is DNA comprising SEQ ID NO: 18, are synthesized, and using pAAV1-RC as a template, tyrosine (Y) at position 445 of the amino acid sequence of VP1 of AAV1 (SEQ ID NO: 2) is substituted with phenylalanine (F) with the use of the Quick Change II XL site-directed mutagenesis kit (Stratagene). Also, a forward primer, which is DNA comprising SEQ ID NO: 19, and a reverse primer, which is DNA comprising SEQ ID NO: 20, are synthesized, and using pAAV2-RC as a template, tyrosine (Y) at position 444 of the amino acid sequence of VP1 of AAV2 (SEQ ID NO: 4) is substituted with phenylalanine (F). Also, a forward primer, which is DNA comprising SEQ ID NO: 21, and a reverse primer, which is DNA comprising SEQ ID NO: 22, are synthesized, and using pAAV9-RC as a template, tyrosine (Y) at position 446 of the amino acid sequence of VP1 of AAV9 (SEQ ID NO: 6) is substituted with phenylalanine (F). The pAAV1-yfRC, pAAV2-yfRC, and pAAV9-yfRC plasmids comprising polynucleotides encoding the substituted amino acid sequences AAV1-yfVP1 (SEQ ID NO: 8), AAV2-yfVP1 (SEQ ID NO: 10), and AAV9-yfVP1-3 (SEQ ID NO: 12), respectively, are prepared. All the pAAV1-yfRC, pAAV2-yfRC, and pAAV9-yfRC comprise the nucleotide sequence (SEQ ID NO: 15) encoding Rep of AAV2.

The second polynucleotide comprises the promoter sequence and the target nucleotide sequence. In addition, the second polynucleotide can adequately comprise, for example, a known enhancer sequence, a Kozak sequence, and a poly A addition signal sequence.

AAV is a helper-dependent virus. When AAV infects a cell for virion production (a cultured cell) in order to prepare the rAAV virion of the present invention, accordingly, co-infection with a helper virus (e.g., adenovirus, herpes virus, or vaccinia virus) is necessary. When a helper virus is not co-infected, AAV inserts the virus genome into the host chromosome, but no infectious AAV virion derived from the inserted virus genome is generated. When a host comprising the inserted virus genome is infected with a helper virus, the infectious AAV virion derived from the inserted genome can be generated. While AAV is capable of infecting a cell derived from a different species, a helper virus needs to be of the same species as the host cell. For example, human AAV can replicate in a canine cell co-infected with a canine adenovirus.

When preparing the rAAV virion of the present invention, a helper virus plasmid (e.g., adenovirus, herpes virus, or vaccinia virus) can be introduced into a cultured cell simultaneously with the first and the second polynucleotides. Preferably, the method for preparation of the present invention further comprises a step of introducing an adenovirus (AdV) helper plasmid. The AdV helper plasmid encodes a protein, such as E1a, E1b, E2a, or E4 orf4, necessary for AAV genome replication. Alternatively, a recombinant virus or non-virus vector (e.g., a plasmid or episome) that carries necessary helper functions may be used. Such recombinant virus is known in the art and can be produced in accordance with a known technique. A variety of adenovirus strains are available from ATCC (American Type Culture Collection) and commercially available. Also, many adenovirus sequences are available from public databases (e.g., PubMed or GenBank).

In the present invention, the AdV helper is preferably derived from the virus of the same species as the cultured cell. When the human cultured cell (293T) is used, for example, a human AdV-derived helper virus vector can be used. A commercially available AdV helper vector (e.g., AAV Helper-Free System: Catalog No. 240071, Agilent Technologies) can be used.

When preparing the rAAV virion of the present invention, the method for transfection of one or more types of plasmids into the cultured cell can employ any of various known methods, such as the calcium phosphate method, lipofection, or electroporation. Such methods are described in, for example, Molecular Cloning 3rd Ed., Current Protocols in Molecular Biology, John Wiley & Sons, 1987-1997.

5. Pharmaceutical Composition Comprising the rAAV Virion of the Present Invention A further aspect of the present invention provides a pharmaceutical composition comprising the rAAV virion of the present invention (the rAAV vector). With the use of the pharmaceutical composition comprising the rAAV virion of the present invention (hereafter, referred to as the pharmaceutical composition of the present invention), the target gene of the β-hexosaminidase modified β-subunit can be introduced into the subject's cell with high efficiency. The present invention provides a method for treatment of Tay-Sachs disease and/or Sandhoff disease using the target gene thus introduced. Since the rAAV virion of the present invention can penetrate the blood-brain barrier of an organism, peripheral administration thereof to the subject enables gene delivery of the rAAV virion of the present invention to neural cells of the brain, the spinal cord, and other organs. In addition, the rAAV virion of the present invention enables gene delivery to neural cells of the brain, the spinal cord, the retina, and other organs via intracerebral or intraspinal administration.

When the pharmaceutical composition of the present invention is used, for example, administration can be made through the oral, parenteral (intravenous), intramuscular, oral mucosal, transrectal, transvaginal, percutaneous, or nasal route or via inhalation, with parenteral administration being preferable, and intravenous, intracerebral, or intraspinal administration being more preferable. A single active ingredient or two or more active ingredients can be incorporated into the pharmaceutical composition of the present invention. Such an active ingredient (or active ingredients) can be supplemented with pharmacologically acceptable carriers or additives and provided in the form of a pharmaceutical preparation. In such a case, the active ingredient(s) of the present invention can be contained in the pharmaceutical preparation in an amount of, for example, 0.1% to 99.9% by weight therein.

Examples of pharmacologically acceptable carriers or additives that can be used include excipient, disintegrator, disintegration enhancer, binding agent, lubricant, coating agent, dye, diluent, solubilizer, solubilization enhancer, isotonizing agent, pH modifier, and stabilizer.

Examples of pharmaceutical preparations suitable for oral administration include powders, tablets, capsules, fine grains, granules, liquids, and syrups. In the case of oral administration, various excipient, such as microcrystalline cellulose, sodium citrate, calcium carbonate, dipotassium phosphate, or glycine, can be used in combination with various disintegrators, such as starch (preferably maize, potato, or tapioca starch), alginic acid, or a sort of double salt of silicic acid, and binding agents for granulation, such as polyvinylpyrrolidone, sucrose, gelatin, and gum Arabic. Also, lubricants, such as magnesium stearate, sodium lauryl sulfate, and talc, are often very effective for tablet formation. A composition of solids of the same species can be filled in a gelatin capsule. In this respect, examples of preferable substances include lactose, and high-molecular-weight polyethylene glycol. When an aqueous suspension and/or elixir are/is to be prepared for oral administration, active ingredients can be used in combination with various sweetening agents, flavoring agents, colorants, or dyes. Alternatively, an emulsifying agent and/or a suspending agent can also be used in combination, according to need. In addition, a diluent, such as water, ethanol, propylene glycol, glycerin, or a mixture of any thereof can be used in combination.

Examples of pharmaceutical preparations suitable for parenteral administration include injections and suppositories. In the case of parenteral administration, a solution of the active ingredients of the present invention in sesame oil or peanut oil or an aqueous solution thereof in propylene glycol can be used. An aqueous solution is adequately buffered (preferably a pH 8 or higher), according to need, and a liquid diluent needs to be made isotonic. An example of such liquid diluent is physiological saline. An aqueous solution thus prepared is suitable for intravenous injection, and an oleaginous solution is suitable for intraarticular injection, intramuscular injection, and subcutaneous injection. Such solutions can be easily prepared under aseptic condition in accordance with a standard pharmaceutical technique well known in the art. In addition, the active ingredients of the present invention can be topically administered, such as skin application. In such a case, topical administration is preferably made in the form of a cream, jelly, paste, or ointment in accordance with a standard medical practice.

A dose of the pharmaceutical composition of the present invention is not particularly limited, and an adequate dose can be determined in accordance with various conditions, such as disease type, the age and symptoms of a patient, the administration route, the purpose of treatment, or use of other medicines. A dose of the pharmaceutical composition of the present invention is, for example, 1 to 5,000 mg, and preferably 10 to 1,000 mg, per adult (e.g., body weight of 60 kg) per day, although the dose is not limited thereto. Such a daily dose may be administered in 2 to 4 separate instances. When the dose unit is expressed in vg(vector genome), a dose is for example $10^9$ to $10^{14}$ vg, preferably $10^{10}$ to $10^{13}$ vg, and more preferably $10^{10}$ to $10^{12}$ vg, per kg of the body weight, although the dose is not limited thereto.

EXAMPLES

Hereafter, embodiments of the present invention are described in detail with reference to the examples, although the present invention is not limited to the following examples. The percentage (%) is by weight, unless otherwise specified.

The method for preparing the AAV-CMV-modHEXB vector used in Examples 1 and 2 (which may also be referred to as AAV-CMV-mod2B) is described in Example 3, the method for preparing the AAV-SynI-modHEXB vector used in Examples 1 and 2 (which may also be referred to as AAV-SynI-mod2B) is described in Example 4, and the method for preparing the AAV-CMV-GFP vector used in Examples 1 and 2 is described in Example 5.

Example 1: Evaluation of Efficacy of Intraventricular Administration of AAV-CMV-modHEXB on Sandhoff Disease Mouse Model 1. Evaluation of Efficacy of AAV-CMV-modHEXB on Sandhoff Disease (Hexb−/−) Mouse Model (Deficiency of Both Hexa and Hexb) Via Intraventricular Administration 1.1. Expression of β-Hexosaminidase (Hex) Activity in the Brain and Other Organs after Intraventricular Administration of AAV-CMV-modHEXB to Sandhoff Disease (SD) Mouse Model AAV-CMV-modHEXB (other name: AAV-CMV-mod2B) was administered once intraventricularly at $5.75\times10^{11}$ vg/25 μl PBS (phosphate buffer) to 15-week-old Sandhoff disease mouse models (SD mice) (the late stage of disease development), the organs were extracted 1 week later, and tissues of the organs were disrupted via sonication (probe sonicator and warm-bath sonicator, 10 minutes) in distilled water containing a protease/phosphatase inhibitor cocktail (final concentration: 20 μM leupeptin, 2 mM EDTA, 1 mM PMSF, 1 mM pepstatin A) (milliQ level) (wet tissue weight: 100 mg/0.3 ml). Following centrifugation at 4° C. and 12,000×g for 15 minutes, the supernatants (tissue extracts) were prepared. The vector amount of $5.75\times10^{11}$ vg/SD mouse is equivalent to approximately $1.9\times10^{13}$ vg/kg of body weight.

A given amount of the extract was subjected to assays of activity of degrading artificial fluorescent substrates; i.e., 4-methylumbelliferyl β-D-glucosaminide (MUG) and 4-methylumbelliferyl 6-sulfo-β-D-glucosaminide (MUGS), in 0.1 M sodium citrate buffer (pH 4.2). Also, protein concentration in the extract was assayed, and substrate-degrading activity per unit protein amount; i.e., specific activity, was determined. In general, an SD mouse lacking HEXB and having HEXA does not have MUG-degrading activity but it has MUGS-degrading activity.

1.2. Expression of Human Modified β-Hexosaminidase B (modHexB) Enzyme Protein in the Brain and Organs after Intraventricular Administration of AAV-CMV-modHEXB to Sandhoff Disease (SD) Mouse Models In Western blot analysis of human modHexB, a given amount (10 μg each) of the tissue extracts obtained in Experiment 1.1 was used as a sample to perform SDS-electrophoresis (SDS-PAGE) (constant current: 15 mA) using 15% polyacrylamide gel. After electrophoresis, the gel was transcribed to a PVDF membrane at a constant voltage of 15 V, and the membrane was treated with a blocking agent for 1 hour. The resultant was treated with the anti-human HexA (αβ) rabbit polyclonal antibody NAG (A) as a primary antibody (a 1,000-fold dilution) at 4° C. overnight, washed with a Tris buffer, treated with the peroxidase-labeled anti-rabbit IgG antibody as a secondary antibody, washed, and subjected to detection of the human modHexB protein using a chemiluminescence kit and LAS4000mini (GEHealthcare).

The results of assays of MUG-degrading specific activity in organ extracts performed in Experiment 1.1 are shown in the upper chart of FIG. 1, and the results of Western blot analysis of proteins in the organ extracts performed in Experiment 1.2 are shown in the lower image of FIG. 1. The modified Hexβ strand progenitor protein was detected in the brain, the brain stem, the heart, and the liver. Gene introduction effects of intraventricular administration of AAV-CMV-modHEXB were observed.

1.3. Evaluation of Distribution of Human Modified β-Hexosaminidase B (modHexB) Enzyme Protein and Decrease of Accumulated GM2 Ganglioside in Brain Regions of Sandhoff Disease (SD) Mouse Models after Intraventricular Administration of AAV-CMV-modHEXB AAV-CMV-modHEXB was administered once intraventricularly at $5.75\times10^{11}$ vg/25 μl PBS (phosphate buffer) to 15-week-old SD mice, the brain was extracted 1 week later, frozen sections thereof were prepared, the frozen sections were allowed to adhere to glass preparations and dehydrated, and the dehydrated frozen sections were fixed in a 4% paraformaldehyde/PBS solution at room temperature for 1 hour. The fixed sections were washed in PBS and subjected to blocking with 5% goat serum/PBS at room temperature for 1 hour.

The human modHEXB enzyme protein was analyzed by subjecting the brain sections after blocking and washing to treatment with the anti-human HexA (αβ) rabbit polyclonal antibody NAG (A) as a primary antibody (1,000-fold diluted) at 4° C. overnight. After the treated brain sections were washed with PBS, the washed brain sections were treated with the Alexa555-labeled anti-rabbit IgG as a secondary antibody, washed, and enclosed in 50% glycerol/PBS.

In order to examine the distribution of GM2 ganglioside (GM2) as the accumulated substrate in the brain and GM2 decrease caused by administration of the AAV vector, the brain sections were treated with the anti-GM2 mouse monoclonal IgM antibody (a 100-fold dilution) at 4° C. overnight. The treated brain sections were washed with PBS, treated with the Alexa388-labeled anti-mouse Ig secondary antibody, washed, and enclosed in 50% glycerol/PBS. As neural cell markers, NEUN (neuron marker), GFAP (astrocyte marker), and Iba1 (microglia marker) were subjected to immunofluorescent and histochemical analysis with the use of the primary antibody and the fluorescence-labeled secondary antibody. The immunofluorescence-labeled brain sections were observed using the BIOREVO apparatus (Keyence).

Figure 2:
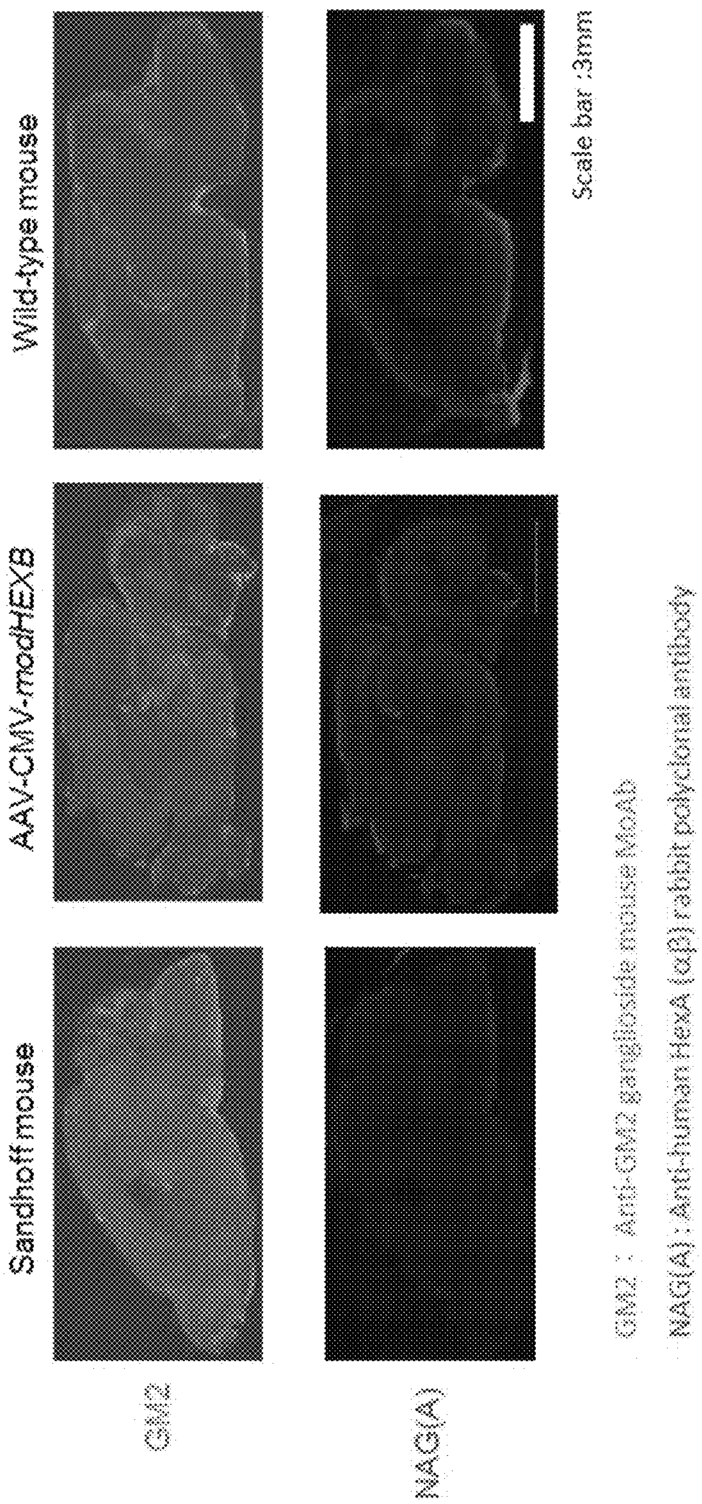
FIG. 2 shows the results of immunofluorescent and histochemical analysis of the brain section of the SD mouse model, the brain section of the SD mouse model after intraventricular administration of AAV-CMV-modHEXB thereto, and the brain section of the wild-type mouse (C57BL/6) using the human modHEXB enzyme protein (with the use of NAG(A) as a primary antibody) and GM2 ganglioside (with the use of anti-GM2 antibody as a primary antibody).

FIG. 2 shows the results of immunofluorescent and histochemical analysis of the brain section of the SD mouse model, the brain section of the SD mouse model after intraventricular administration of AAV-CMV-modHEXB thereto, and the brain section of the wild-type mouse (C57BL/6) using the human modHEXB enzyme protein (with the use of NAG(A) as a primary antibody) and GM2 ganglioside (with the use of anti-GM2 antibody as a primary antibody). The brain sections of the SD mouse model were positive for anti-GM2 antibody staining and negative for NAG (A) staining. The brain sections of the wild-type mouse (C57BL/6) were negative for anti-GM2 antibody staining and slightly positive for NAG (A) staining (mouse Hex may have been cross-stained). After intraventricular administration of AAV-CMV-modHEXB to the SD mouse model, the brain sections were partially positive for NAG (A) staining, and the region positive for NAG (A) staining was negative for anti-GM2 antibody staining. In the region where human modHexB enzyme protein distribution was observed, specifically, decrease of accumulated GM2 was observed.

Figure 3A:
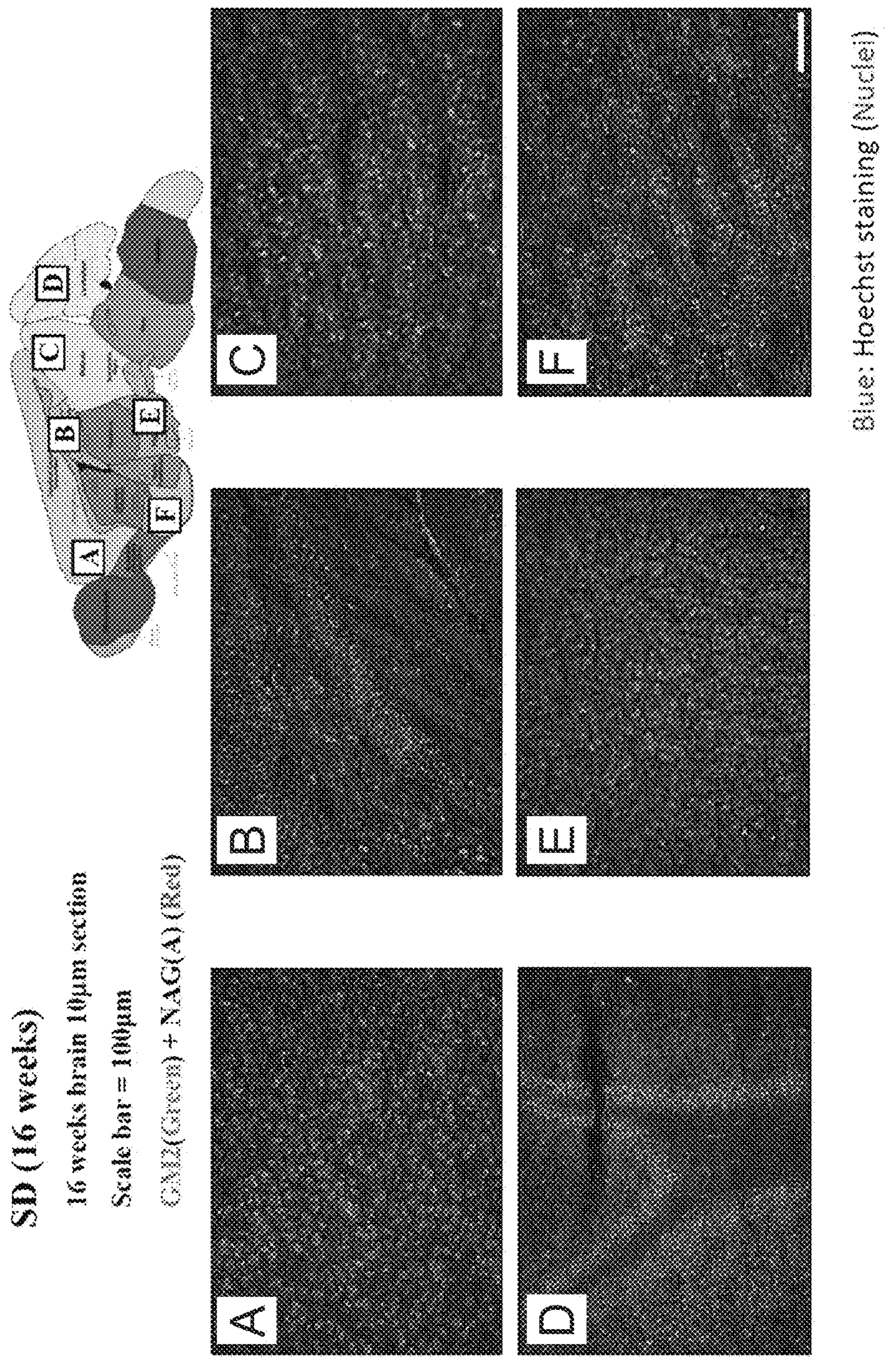
FIG. 3A shows the results of immunofluorescent and histochemical analysis of GM2 ganglioside (green) accumulated in each brain region of the SD mouse model (Hexb−/−).

FIG. 3A shows the results of immunofluorescent and histochemical analysis of GM2 ganglioside (green) accumulated in each brain region of the SD mouse model (Hexb−/−). The results demonstrate that the brain sections were positive for anti-GM2 antibody staining and negative for NAG (A) staining. Accumulation of GM2 ganglioside was observed. modHEXB (red) was not detected.

Figure 3B:
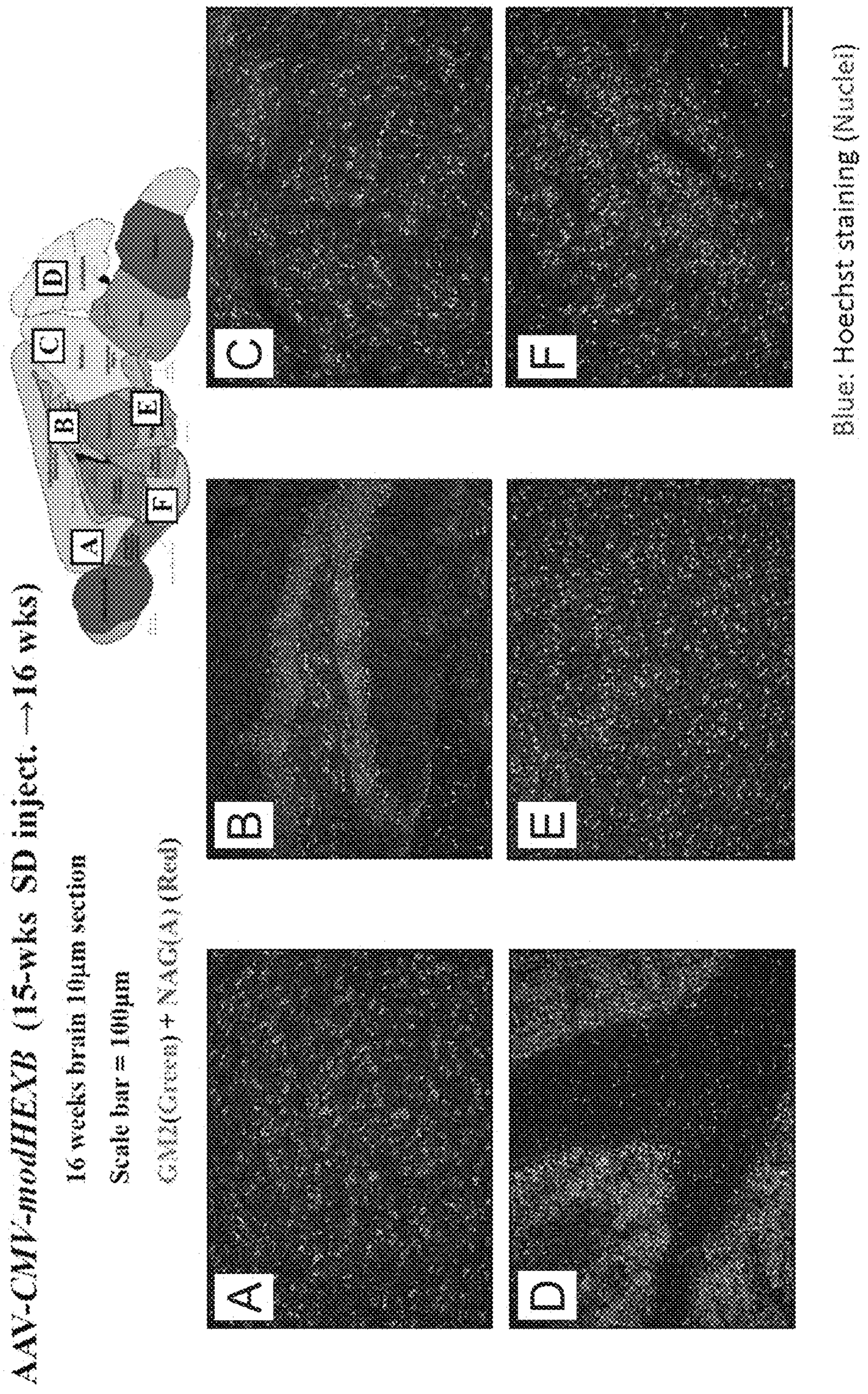
FIG. 3B shows the results of immunofluorescent and histochemical analysis of GM2 ganglioside (green) and modHEXB (red) in each brain region of the SD mouse model (Hexb−/−) to which AAV-CMV-modHEXB had been administered intraventricularly.

FIG. 3B shows the results of immunofluorescent and histochemical analysis of GM2 ganglioside (green) and modHEXB (red) in each brain region of the SD mouse model (Hexb−/−) to which AAV-CMV-modHEXB had been administered intraventricularly. The results demonstrate that the brain sections were slightly positive for anti-GM2 antibody staining and positive for NAG (A) staining. modHEXB (red) was expressed, and decrease of GM2 ganglioside (green) was observed.

Figure 3C:
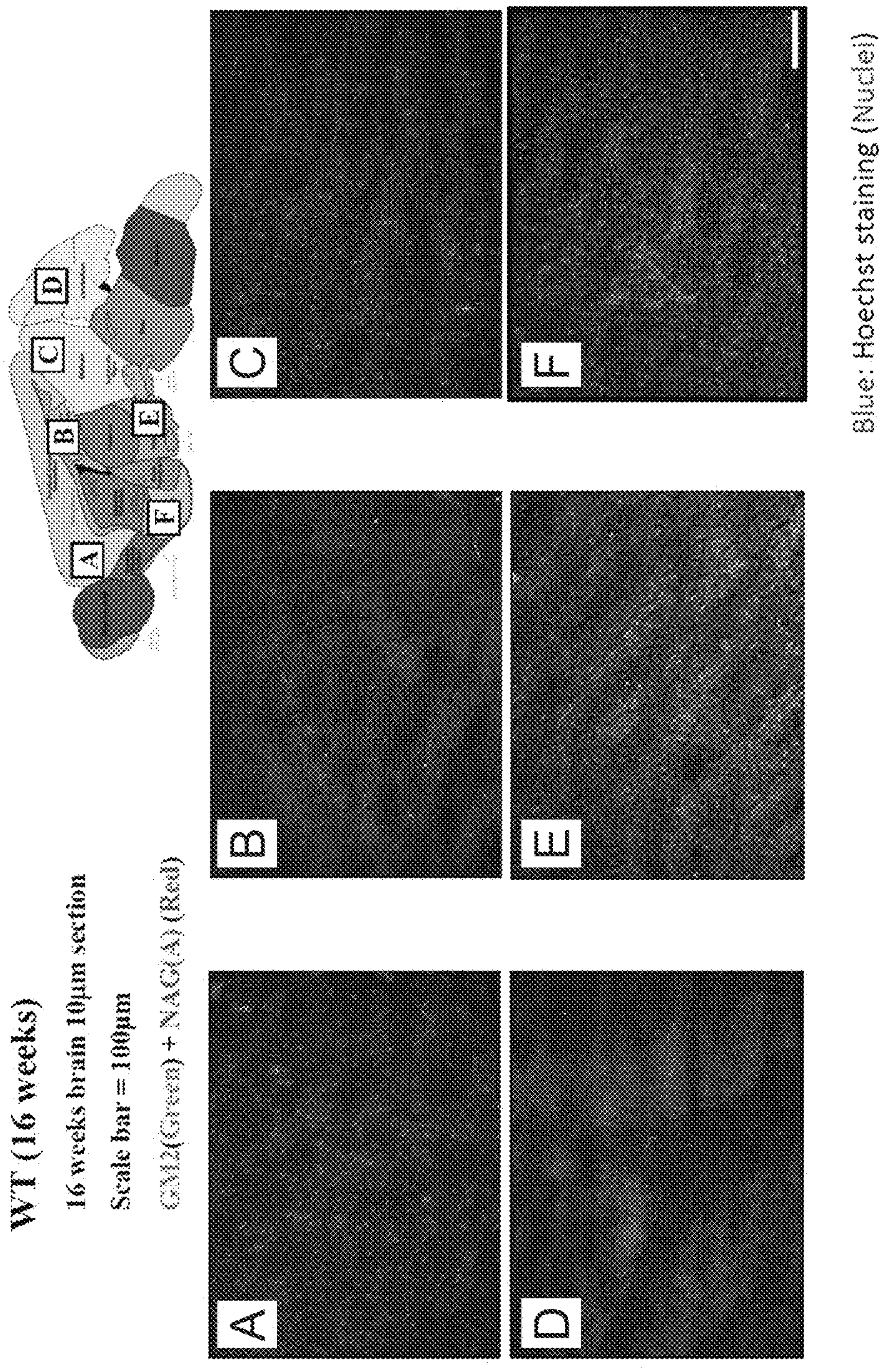
FIG. 3C shows the results of immunofluorescent and histochemical analysis of GM2 ganglioside (green) and modHEXB (red) in each brain region of the wild-type mouse (C57BL/6).

FIG. 3C shows the results of immunofluorescent and histochemical analysis of GM2 ganglioside (green) and modHEXB (red) in each brain region of the wild-type mouse (C57BL/6). The results demonstrate that the brain sections were slightly positive for anti-GM2 antibody staining and slightly positive for NAG (A) staining. GM2 ganglioside (green) was not accumulated. NAG (A) used as a primary antibody for modHEXB detection was found to have cross-stained mouse Hex.

2. Distribution of Green Fluorescent Protein Expression in Sandhoff Disease (Hexb+/−) Heterozygous Mouse Model Via Intraventricular Administration of AAV-CMV-GFP To a 15-week-old Sandhoff disease heterozygous mouse model (Hexb+/−, n=1), AAV-CMV-GFP ($5.5\times10^{11}$ vg) was administered intraventricularly (25 μl), the cerebral ventricle was extracted 1 week later, the frozen brain sections were prepared, and EGFP (Ex=488 nm, Em=514 nm) was monitored using the BIOREVO apparatus. As neural cell markers, NEUN (neuron marker), GFAP (astrocyte marker), and Iba1 (microglia marker) were subjected to immunofluorescence staining with the use of the primary antibody and the fluorescence-labeled secondary antibody (Alexa544-anti-rabbit IgG), and GFP-expressing cell types were analyzed.

Figure 4:
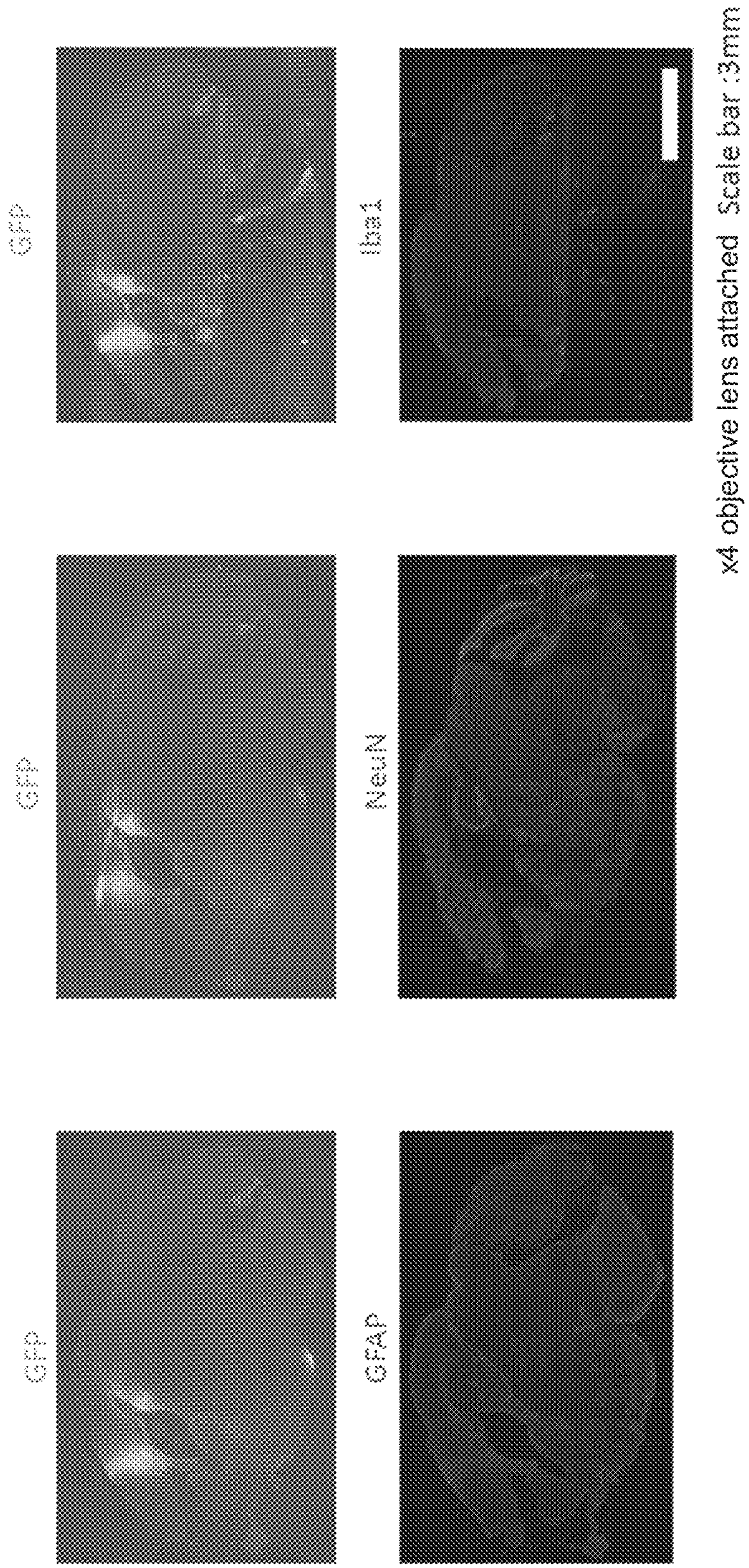
FIG. 4 shows the results of immunofluorescent and histochemical analysis of Example 1, Experiment 2.

FIG. 4 shows the results of immunofluorescent and histochemical analysis mentioned above. In FIG. 4, the upper images show GFP color development of each section, and the lower images show the results of staining of the sections shown in the upper images with NEUN (neuron marker), GFAP (astrocyte marker), and Iba1 (microglia marker). Because the sections were found to be positive for NEUN, GFAP, and Iba1, the sections were confirmed to comprise cerebral parenchyma-constituting cells. Since a region in the vicinity of the sites of administration of the sections were positive for GFP, AAV-CMV-GFP ($5.5\times10^{11}$ vg/mouse) was administered to a 15-week-old Sandhoff disease heterozygous mouse intraventricularly, and green fluorescence induced by GFP expressed in the vicinity of the site of administration was observed 1 week after administration. The results of observation verify that the AAV vector administered to the cerebral spinal fluid was introduced into cerebral parenchyma-constituting cells and that the GFP gene was expressed under the control of CMVP promoter.

3. Examination of Timing of Single Intraventricular Administration of AAV-CMV-modHEXB To the aforementioned 15-week-old SD mouse (the late stage of disease development), AAV-CMV-modHEXB (other name: AAV-CMV-mod2B) was administered once intraventricularly at $5.75\times10^{11}$ vg/25 μl PBS (phosphate buffer), and modHexB expression in the organs was analyzed 1 week later (at the age of 16 weeks). Further, AAV-CMV-modHEXB was administered once intraventricularly at $5.75\times10^{11}$ vg/25 μl PBS (phosphate buffer) to a 14-week-old SD mouse (the late stage of disease development), and modHexB expression was analyzed 1 week later (at the age of 15 weeks). In addition, AAV-CMV-modHEXB was administered once intraventricularly at $5.75\times10^{11}$ vg/25 μl PBS (phosphate buffer) to a 10-week-old SD mouse (the early stage of disease development) intraventricularly, and modHexB expression was analyzed 5 weeks later (at the age of 15 weeks). modHexB expression in each organ was evaluated in accordance with the procedure described in 1.1. above in which recovery of MUG-degrading activity was employed as the indicator.

Figure 5:
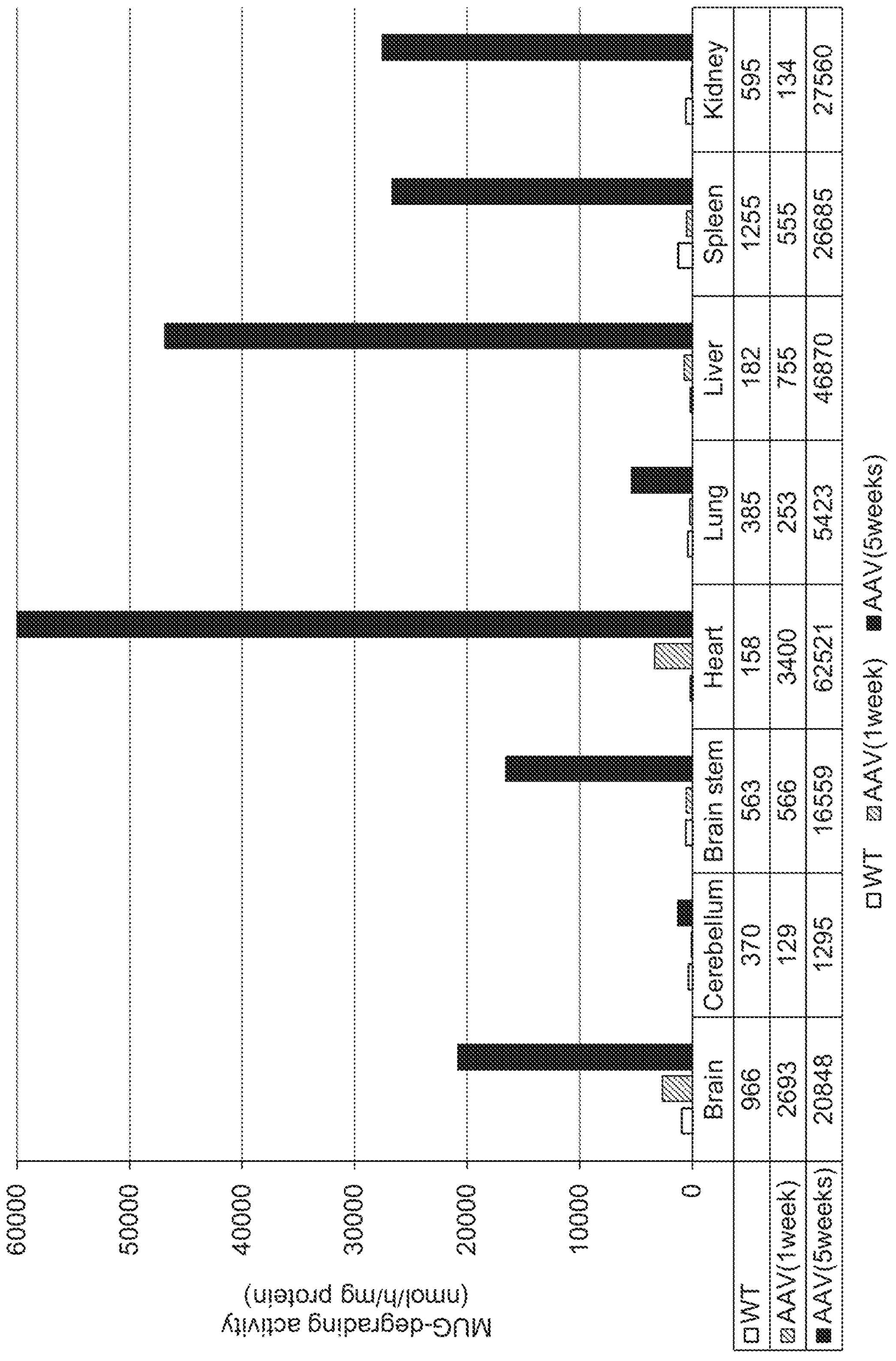
FIG. 5 shows the results of Example 1, Experiment 3.

The results are shown in FIG. 5. In the brain and in the heart, MUG-degrading activity, which was several times greater than that in wild-type mice, was observed 1 week after single intraventricular administration (administration at the age of 14 weeks and anatomy at the age of 15 weeks). Five weeks after single intraventricular administration (administration at the age of 10 weeks and anatomy at the age of 15 weeks), recovery of MUG-degrading activity was observed to a significant extent in the brain, the brain stem, the heart, the liver, the spleen, and the kidney. This indicates continuous expression of the introduced gene, stability of modHexB as an expression product in vivo, and incorporation of the secreted modHexB into the marginal cells (cross-correction effects).

4. Examination of Single Intraventricular Dose of AAV-CMV-modHEXB

AAV-CMV-modHEXB was administered once intraventricularly at $5.75\times10^{9}$ vg, $3.45\times10^{10}$ vg, and $5.75\times10^{11}$ vg/25 μl PBS (phosphate buffer), respectively, to 10-week-old SD mice (the early stage of disease development), and modHexB expression in each organ was analyzed 5 weeks later (at the age of 15 weeks). modHexB expression in each organ was evaluated in accordance with the procedure described in 1.1. above in which recovery of MUG-degrading activity was employed as the indicator.

Figure 6:
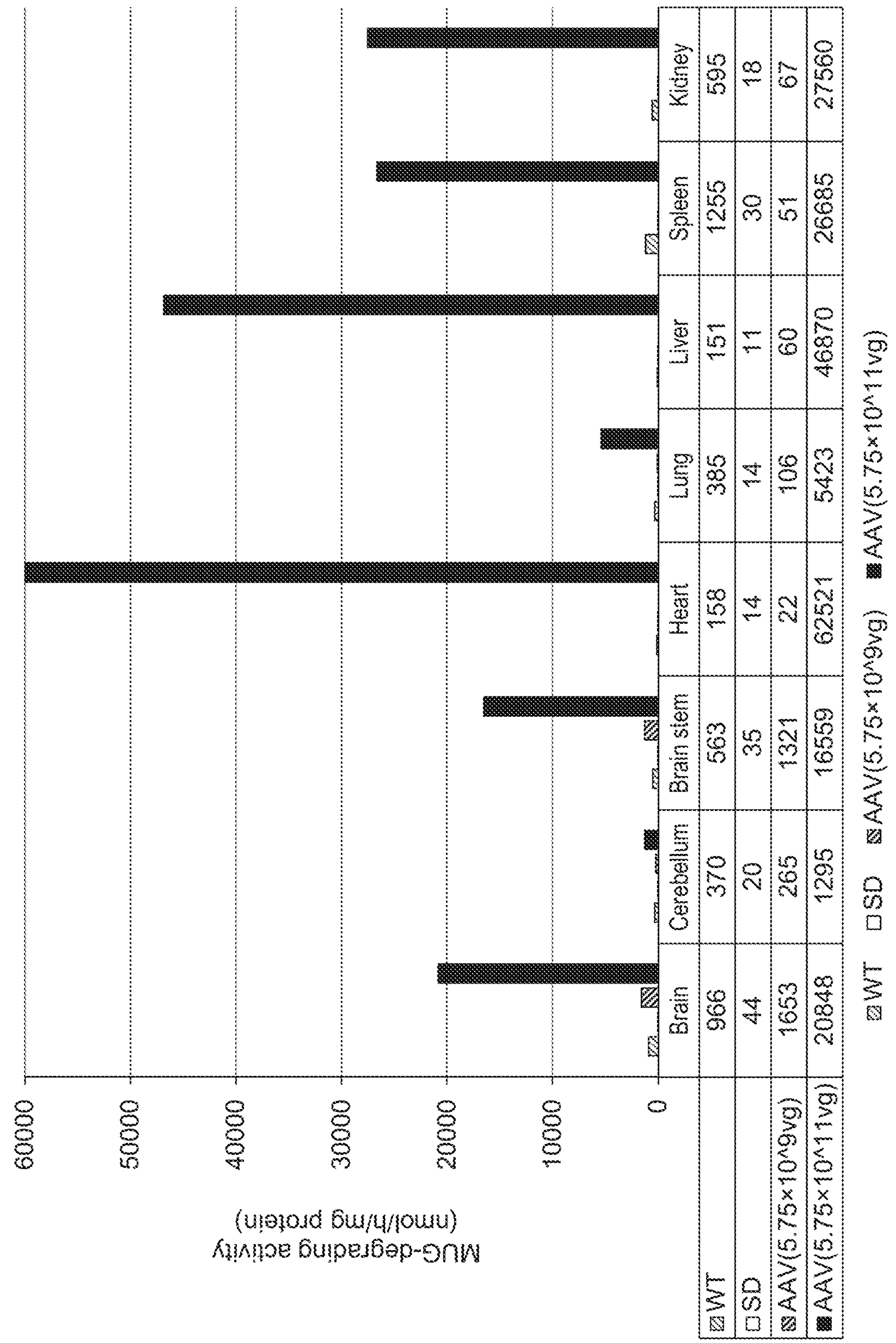
FIG. 6 shows the results of Example 1, Experiment 4.

The results are shown in FIG. 6 (FIG. 6 shows the results of single administration at $5.75\times10^{9}$ vg and $5.75\times10^{11}$ vg). When AAV-CMV-modHEXB was to be administered to 10-week-old SD mice (the early stage of disease development), the modHexB activity level in each organ was approximately equivalent to that observed in wild-type (WT) mice at any dose.

Summary of Experiments 1 to 4

In Experiment 2, AAV-CMV-GFP was administered intraventricularly at $5.5\times10^{11}$ vg/mouse to 15-week-old Sandhoff disease heterozygous mouse models, and green fluorescence of GFP expressed in the vicinity of the site of administration was observed 1 week later. The AAV vector administered to the cerebral spinal fluid was introduced into the cerebral parenchyma-constituting cells, and the GFP gene was expressed under the control of the CMVP promoter in the cells.

In Experiment 1.3., AAV-CMV-modHEXB was administered intraventricularly at $5.75\times10^{11}$ vg/mouse to a 15-week-old Sandhoff disease homozygous mouse (n=1), and immunofluorescence (red) to the anti-human Hex antibody was observed in a wide range of the cerebral region 1 week later (FIG. 2). That is, modHexB secreted from the modHEXB-expressing cells, as well as from the cells into which the AAV vector had been introduced, was incorporated into cells constituting other cerebral regions through the cerebral spinal fluid (i.e., cross-correction effects were suggested).

In Experiment 1.3., immunofluorescence (green) to the anti-GM2 antibody was observed in a wide region of the cerebral region of the 15-week-old Sandhoff disease homozygous mouse as a result of immunohistochemical staining involving the use of the anti-GM2 ganglioside antibody and the anti-human Hex antibody (FIG. 3A). As a result of intraventricular administration of AAV-CMV-modHEXB to the 15-week-old homozygous mice at $5.75\times10^{11}$ vg/mouse, a region exhibiting NAG (A)-positive immunofluorescence (red), attenuated immunofluorescence (green) to the anti-GM2 antibody, and a decreased amount of GM2 accumulated was observed (FIG. 3B). This indicates that modHexB derived from the AAV-expressing cells was incorporated into the peripheral neural cells, then the incorporated modHexB was transported to the lysosome, and the accumulated GM2 was degraded.

5. Efficacy of Single Intraventricular Administration of AAV-CMV-modHEXB to 8-Week-Old Sandhoff Disease Mouse Model 5.1. Recovery of Hex (MUG-Degradation) Activity in Each Organ by Single Intraventricular Administration of AAV-CMV-modHEXB to Sandhoff Disease Mouse Model After AAV-CMV-modHEXB was administered once intraventricularly at $5.75\times10^{11}$ vg/mouse to 8-week-old SD mice, the mice were subjected to autopsy at the age of 17 weeks, and Hex (MUG degradation) activity in each organ was assayed. The experimental procedure was the same as that in Experiments 1 to 3.

Figure 7:
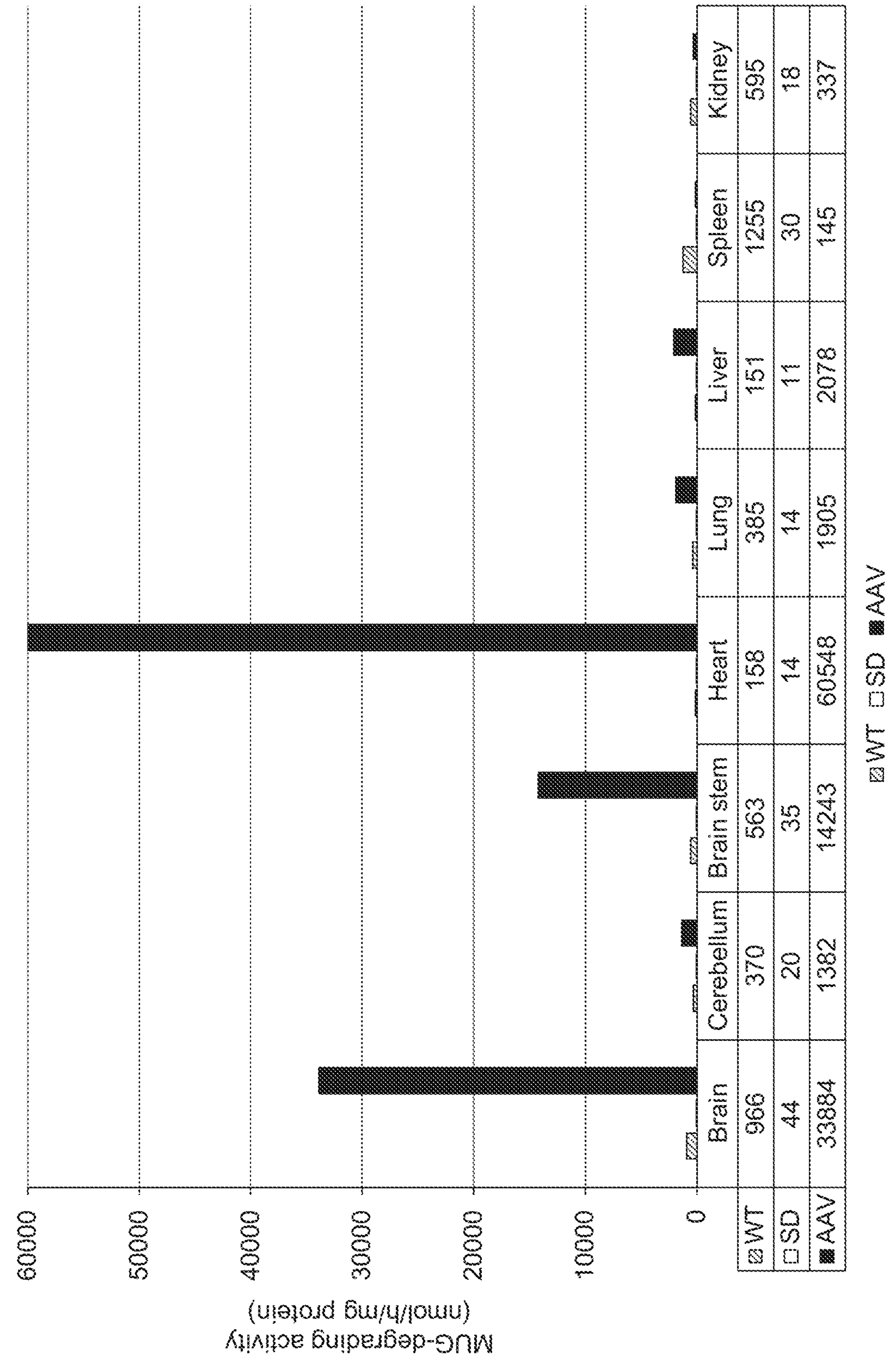
FIG. 7 shows the results of Example 1, Experiment 5.1.

The results are shown in FIG. 7. For comparison, the results of activity assays on wild-type mice (WT) and SD mice (SD) are shown. Hex activity was recovered to a significant extent in the brain, the brain stem, and the heart.

5.2. Distribution of HexB and Decrease of Accumulated GM2 Ganglioside in Brain Regions of Sandhoff Disease (SD) Mouse Models after Single Intraventricular Administration of AAV-CMV-modHEXB AAV-CMV-modHEXB was administered once intraventricularly at $5.75\times10^{11}$ vg/mouse to 8-week-old SD mice, the mice were subjected to autopsy at the age of 17 weeks, and the brain sections were subjected to immunostaining. The experimental procedure was the same as that in Experiments 1 to 3. Immunostaining was performed in accordance with the procedure described in Experiment 1.3.

Figure 8:
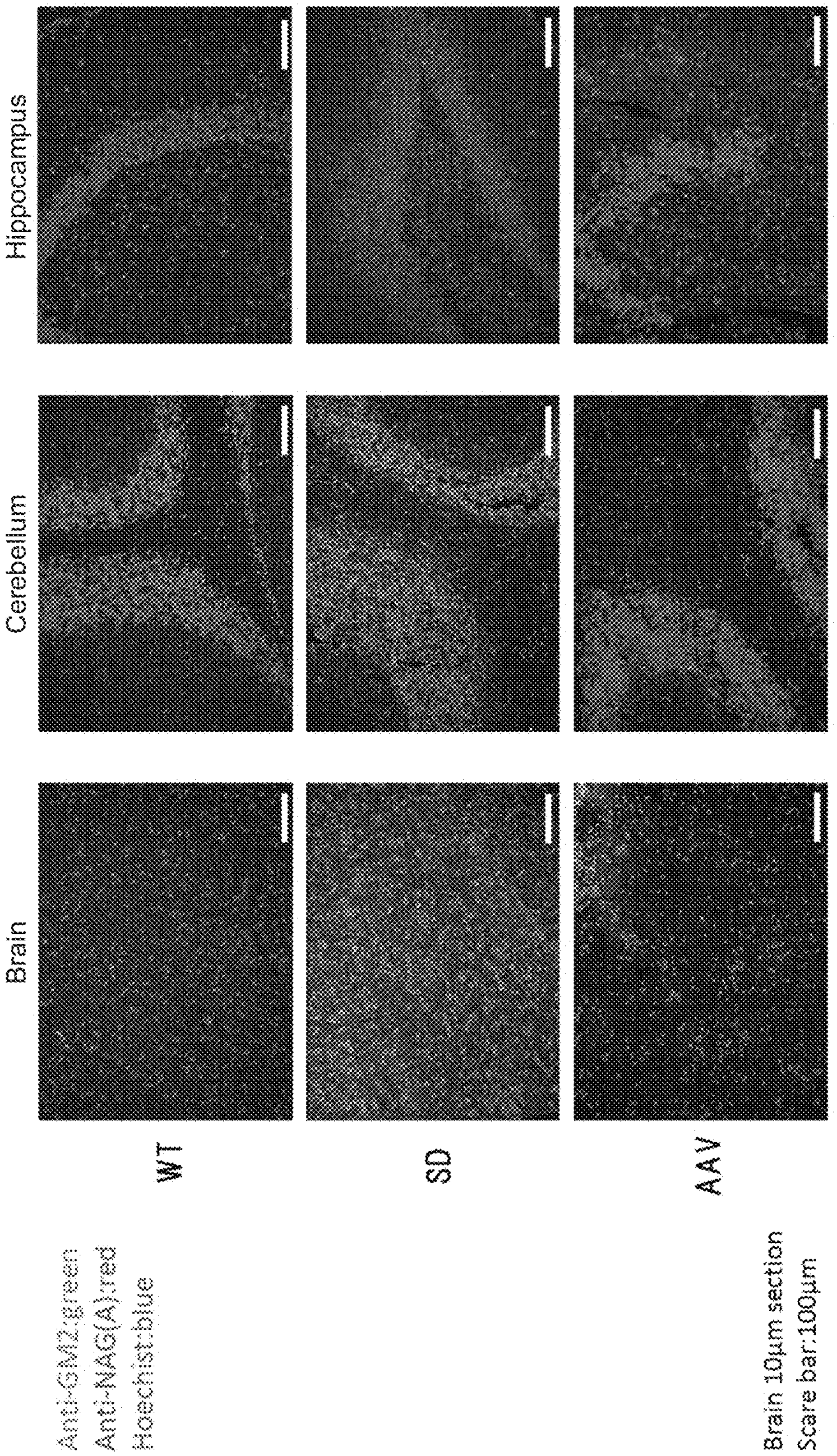
FIG. 8 shows the results of Example 1, Experiment 5.2.

FIG. 8 shows the results of immunofluorescent and histochemical analysis of the human modHEXB enzyme protein (with the use of NAG (A) as a primary antibody, red), GM2 ganglioside (with the use of anti-GM2 antibody as a primary antibody, green), and cell nuclei (Hoechst staining, blue) in regions (the brain, the cerebellum, and the hippocampus) in the brain section of the wild-type mouse (WT), the brain section of the SD mouse model (SD), and the brain section of the SD mouse model after intraventricular administration of AAV-CMV-modHEXB thereto (AAV). All the regions in the brain section of the wild-type mouse (WT) were found to be slightly positive for the human modHEXB enzyme protein (cross-staining of mouse Hex), negative for GM2 ganglioside, and positive for Hoechst staining. All the regions in the brain section of the SD mouse model (SD) were found to be negative for the human modHEXB enzyme protein, positive for GM2 ganglioside, and positive for Hoechst staining. After intraventricular administration of AAV-CMV-modHEXB, all the regions in the brain section of the SD mouse model (AAV) were found to be positive for the human modHEXB enzyme protein, slightly positive for GM2 ganglioside, and positive for Hoechst staining. While GM2 ganglioside had been accumulated in the brain of the SD mouse, decrease of GM2 ganglioside was observed as a result of administration of AAV-CMV-modHEXB.

5.3. Decrease of CD68-Positive Activated Microglia in the Cerebral Region of Sandhoff Disease Mouse Model Via Single Intraventricular Administration of AAV-CMV-modHEXB AAV-CMV-modHEXB was administered once intraventricularly at $5.75\times10^{11}$ vg/mouse to 8-week-old SD mice, the mice were subjected to autopsy at the age of 17 weeks, and the brain sections were subjected to immunostaining. The experimental procedure was the same as that in Experiments 1 to 3. Immunostaining was performed in accordance with the procedure descried in Experiment 1.3.

Figure 9:
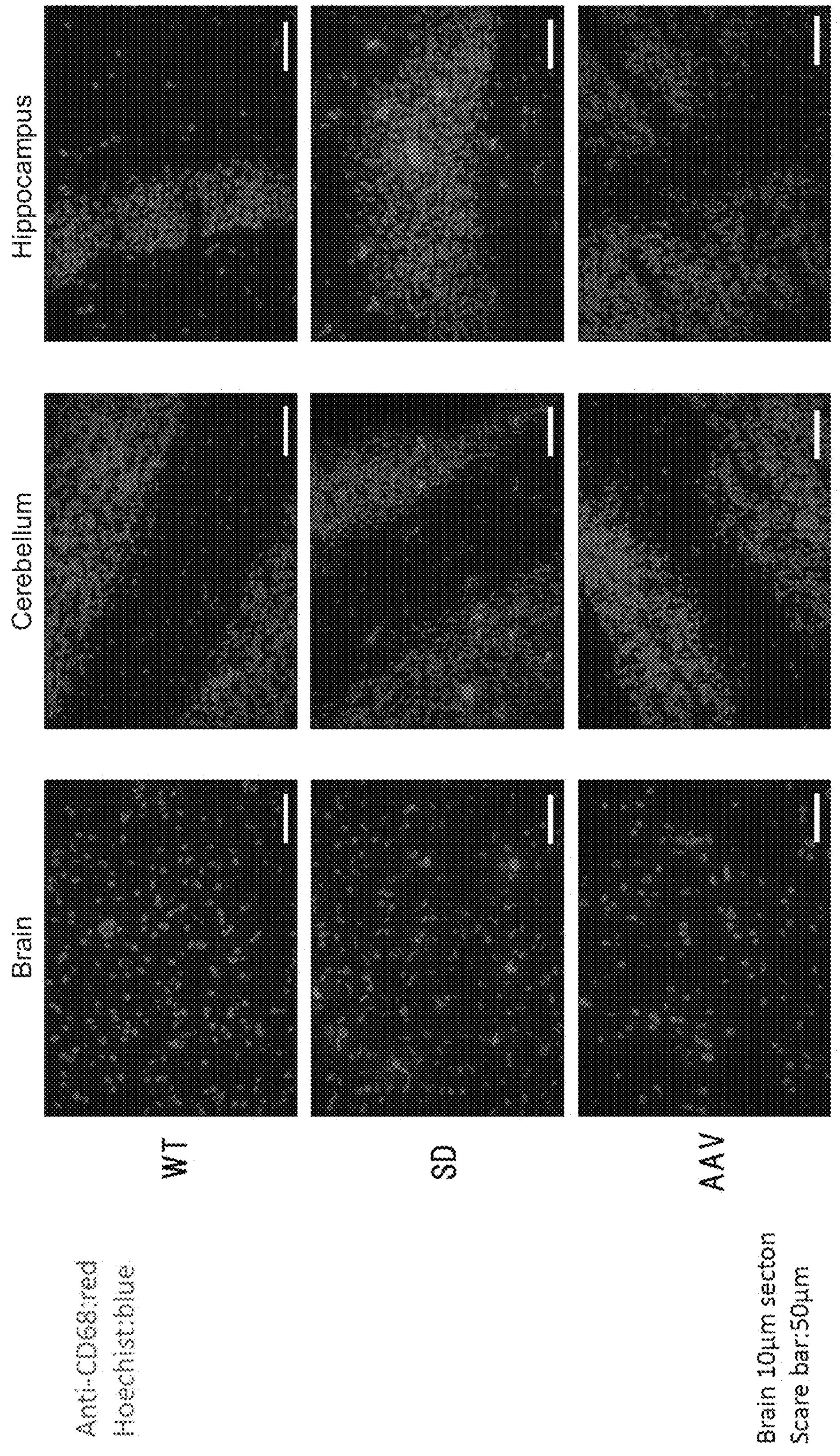
FIG. 9 shows the results of Example 1, Experiment 5.3.

FIG. 9 shows the results of immunofluorescent and histochemical analysis of CD68 (anti-CD68 antibody was used as the primary antibody, red) and cell nuclei (Hoechst staining, blue) in regions (the brain, the cerebellum, and the hippocampus) in the brain section of the wild-type mouse (WT), the brain section of the SD mouse model (SD), and the brain section of the SD mouse model after intraventricular administration of AAV-CMV-modHEXB thereto (AAV). All the regions in the brain section of the wild-type mouse (WT) were found to be slightly positive for CD68 and positive for Hoechst staining. All the regions in the brain section of the SD mouse model (SD) were found to be strongly positive for CD68 and positive for Hoechst staining. After intraventricular administration of AAV-CMV-modHEXB, all the regions in the brain section of the SD mouse model (AAV) were found to be slightly positive for CD68 and positive for Hoechst staining. While CD68 had been accumulated in the brain of the SD mouse, decrease of CD68 was observed as a result of administration of AAV-CMV-modHEXB.

5.4. Decrease of Inflammatory Chemokine (Mip1) in the Cerebral Region of Sandhoff Disease Mouse Model Via Single Intraventricular Administration of AAV-CMV-modHEXB AAV-CMV-modHEXB was administered once intraventricularly at $5.75\times10^{11}$ vg/mouse to 8-week-old SD mice, the mice were subjected to autopsy at the age of 17 weeks, and inflammatory chemokine (Mip1-α) in the brain, the cerebellum, and the brain stem was quantified. Mip1-α in the brain, the cerebellum, and the brain stem of the wild-type mice (WT) and the SD mouse models (SD) was quantified in the same manner. Mip1-α was quantified using the Mouse CCL3/MIP-1 alpha Quantikine ELISA Kit (R&D Systems). Other experimental procedure was the same as that in Experiments 1 to 3.

Figure 10:
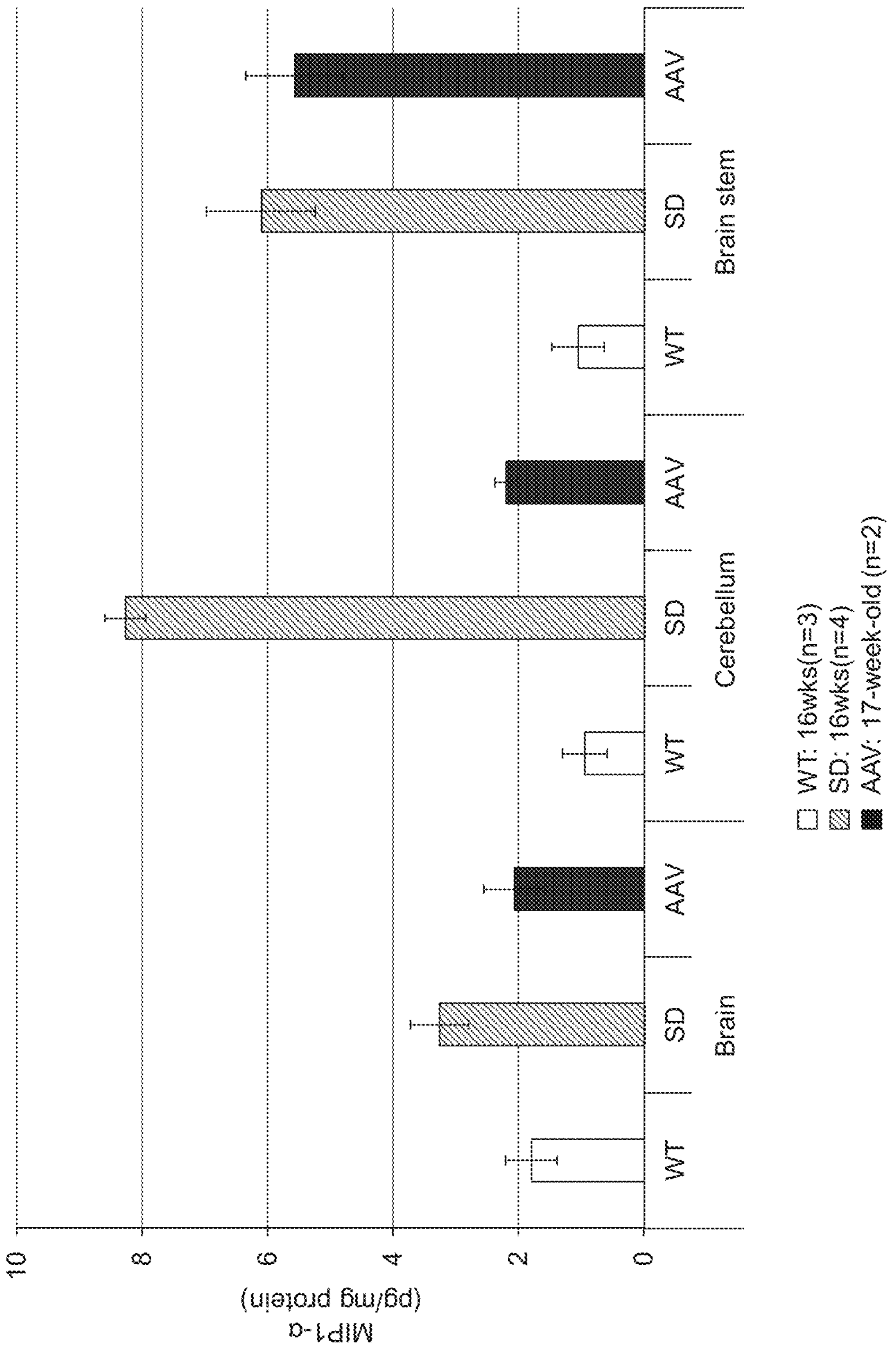
FIG. 10 shows the results of Example 1, Experiment 5.4.

The results are shown in FIG. 10. The amount of Mip1-α increased in the brain, the cerebellum, and the brain stem of the SD mice was found to have decreased to the level observed in the brain and the cerebellum of the wild-type mice as a result of single intraventricular administration of AAV.

6. Evaluation of effects on motor functions, body weight, and survival time by the rotarod performance test 6.1. Examination of single intraventricular dose of AAV-CMV-modHEXB to Sandhoff disease mouse models (Hexb−/−) for improvement of motor functions and body weight AAV-CMV-modHEXB was administered once intraventricularly at $5.75\times10^{10}$ vg/mouse or $5.75\times10^{11}$ vg/mouse to 8-week-old adult SD mice (the early stage of disease development), and the mice were subjected to the rotarod performance test every week starting at the age of 11 weeks.

The rotarod performance test was initiated at 4 round-per-minutes (rpm), the number of revolution was increased to 40 rpm in 120 seconds, each mouse was subjected to the test 6 times, and the average time until the mice fell from the rotarod was measured. The wild-type mice (WT) and the SD mice (SD) of the same age were subjected to the test under the same conditions. A practice test was performed 1 week before the actual test.

Body weight was measured and survival (survival time) was inspected at each time point.

Figure 11A:
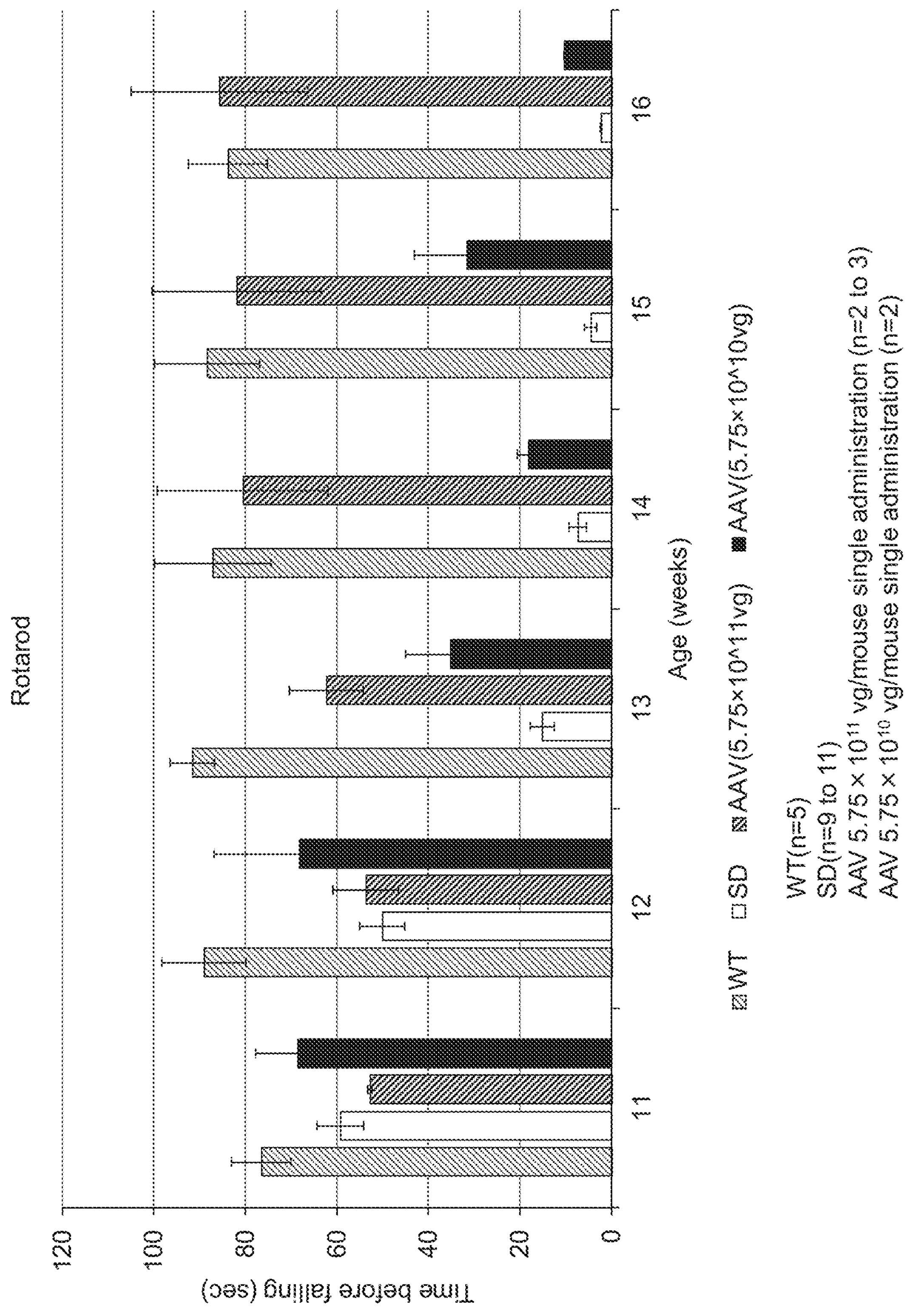
FIG. 11A shows the results of the rotarod performance test performed in Example 1, Experiment 6.1.
Figure 11B:
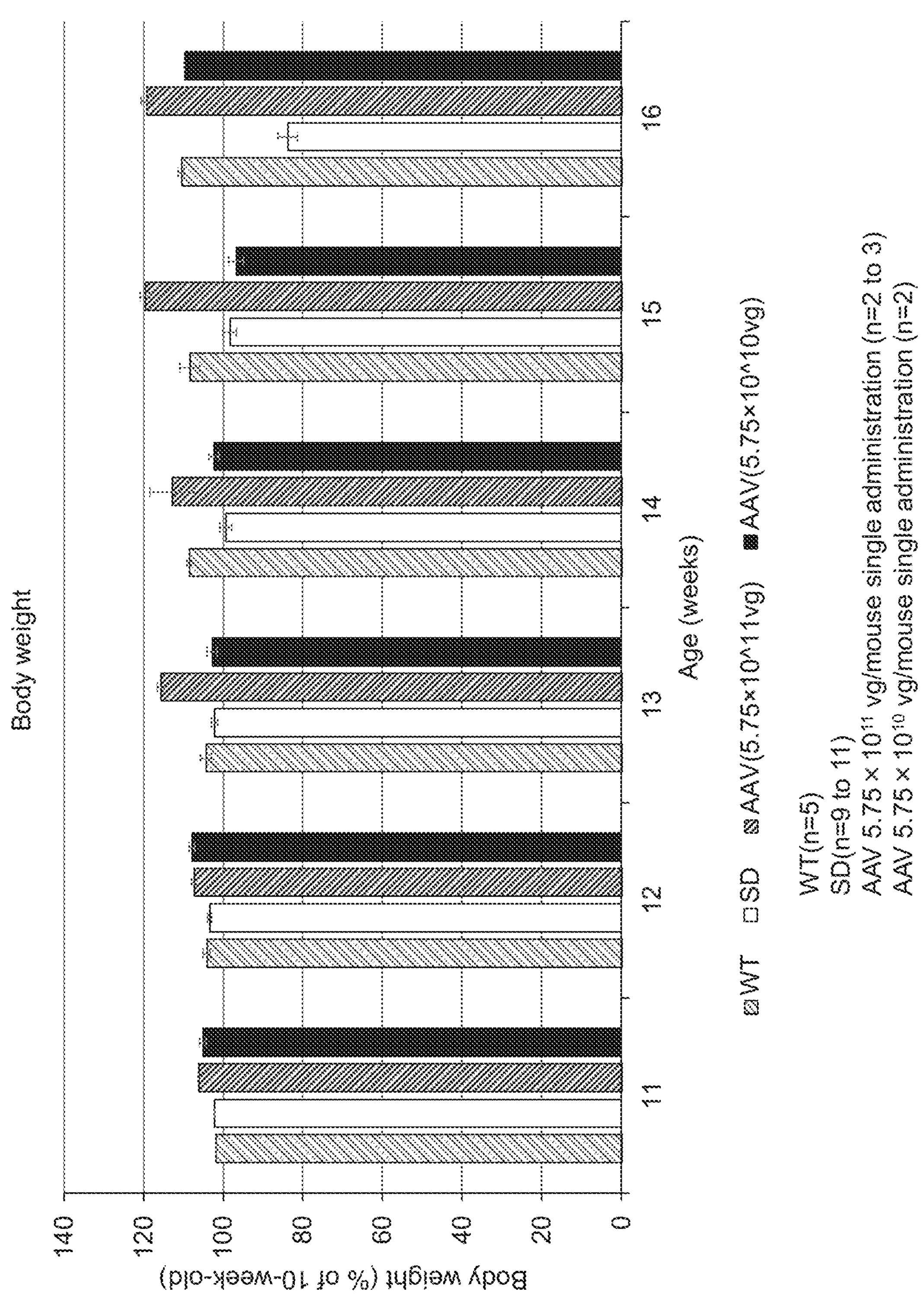
FIG. 11B shows the results of measurement of body weight performed in Example 1, Experiment 6.1.

FIG. 11A shows the results of the rotarod performance test, and FIG. 11B shows the results of body weight measurement. The SD mice to which AAV-CMV-modHEXB had been administered at $5.75\times10^{10}$ vg/mouse died at the age of 14 weeks.

As a result of single administration of AAV-CMV-modHEXB at $5.75\times10^{11}$ vg/mouse at the age of 8 weeks, the SD mice exhibited the rotarod performance equivalent to the wild-type mice. When a dose of AAV-CMV-modHEXB was $5.75\times10^{10}$ vg/mouse, in contrast, the disease development was slightly delayed, and the survival time was not prolonged.

6.2. Effects of Single Intraventricular Administration of AAV-CMV-modHEXB to 8-Week-Old Sandhoff Disease Mouse Models (Hexb−/−) on Motor Functions AAV-CMV-modHEXB was administered intraventricularly at $1.15\times10^{11}$ vg/mouse to 8-week-old SD mice. The rotarod performance test was performed in the same manner as in Experiment 6.1., and the average time until the mice fell from the rotarod was measured.

Figure 12:
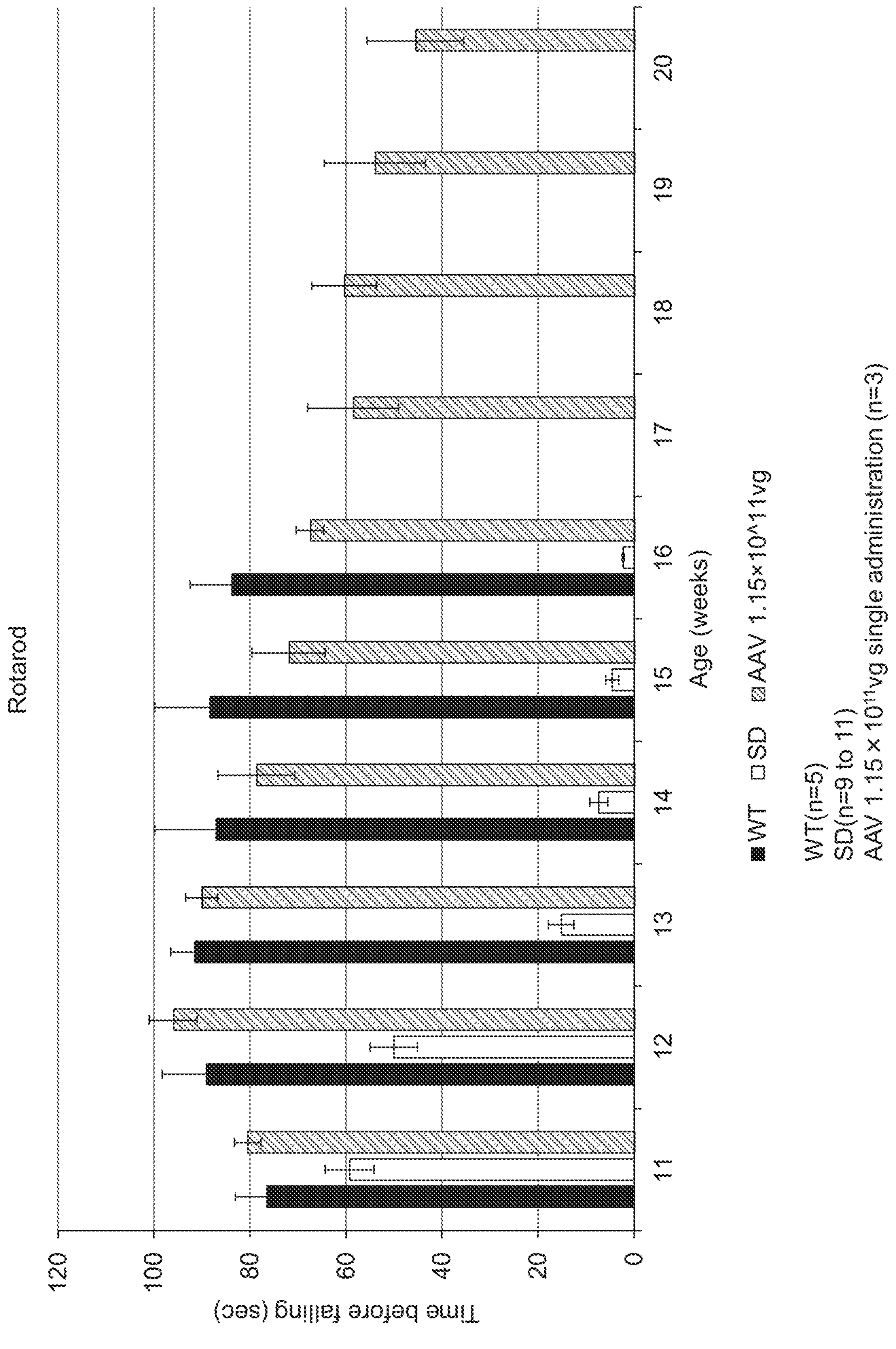
FIG. 12 shows the results of the rotarod performance test performed in Example 1, Experiment 6.2.

The results are shown in FIG. 12. As a result of single administration of AAV-CMV-modHEXB at $1.15\times10^{11}$ vg/mouse at the age of 8 weeks, the rotarod performance was deteriorated after the age of 14 weeks. This indicates that effects on motor functions were attenuated.

7. Hex Activity Enhancement in Organs Via Single Administration of AAV-CMV-modHEXB to the Brain Ventricle or the Temporal Vein of Sandhoff Disease Heterozygous (Hexb+/−) Newborn (P0 to P2) Mice After AAV-CMV-modHEXB was administered to the brain ventricle or the temporal vein of SD heterozygous mice, enhancement of β-hexosaminidase (Hex) activity in the brain and the organs was evaluated.

AAV-CMV-modHEXB was administered once at $1.15\times10^{11}$ vg/5 l PBS (phosphate buffer) or $1.15\times10^{10}$ vg/5 μl PBS to the brain ventricle or the temporal vein of newborn SD heterozygous mice (P0 to P1), the mice were perfused with PBS at the age of 10 weeks, the organs (the brain, the heart, the lung, the liver, the spleen, and the kidney) were extracted, and tissue was disrupted via sonication (probe sonicator and warm-bath sonicator, 10 minutes) in distilled water containing a protease/phosphatase inhibitor cocktail (final concentration: M leupeptin, 2 mM EDTA, 1 mM PMSF, 1 mM pepstatin A) (milliQ level) (wet tissue weight: 100 mg/0.3 ml). Following centrifugation at 4° C. and 12,000×g for 15 minutes, the supernatant (tissue extract) was prepared.

A given amount of an extract was assayed in respect of activity of degrading an artificial fluorescent substrate; i.e., 4-methylumbelliferyl β-D-glucosaminide (MUG), in 0.1 M sodium citrate buffer (pH 4.2). Also, protein concentration in the extract was assayed, and enzyme specific activity was determined.

Figure 13A:
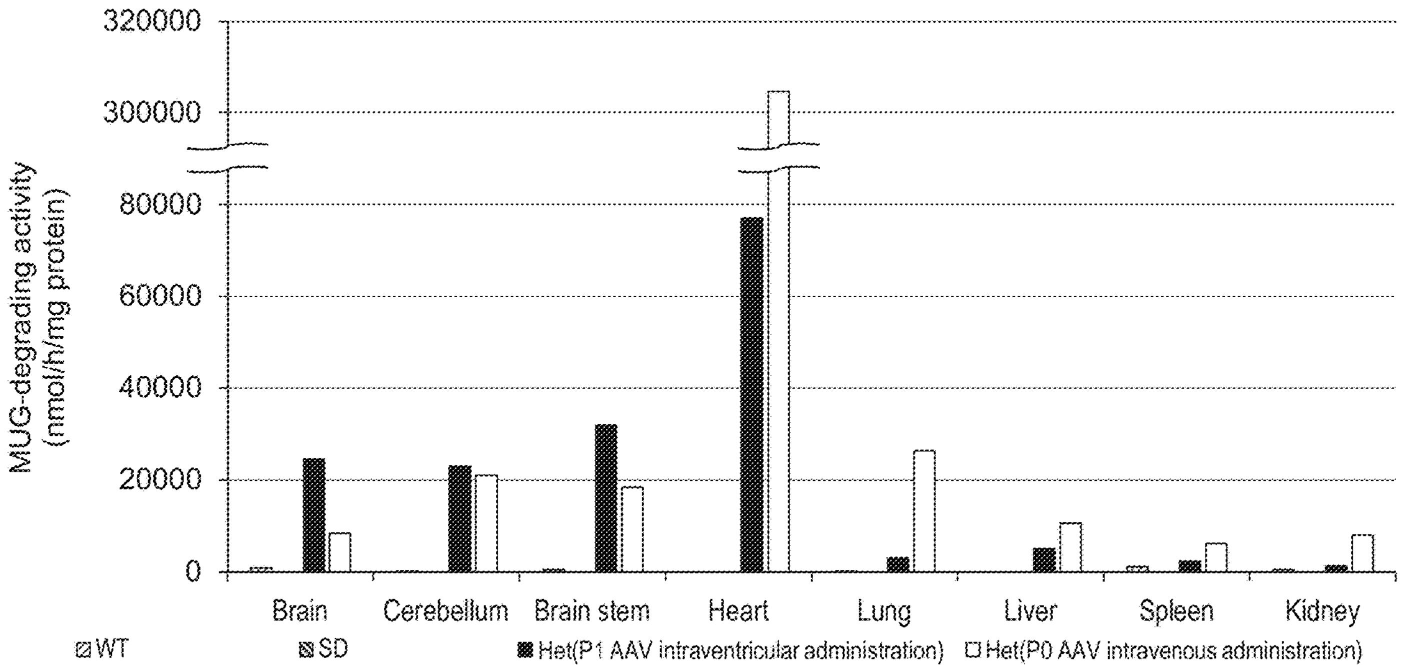
FIG. 13A shows specific activity of Hex activity (MUG-degrading activity) in each organ 10 weeks after single administration of AAV-CMV-modHEXB at $1.15\times10^{11}$ vg/mouse to the brain ventricle or the temporal vein of Sandhoff disease heterozygous (Hexb+/−) newborn (P0 to P2) mice.

FIG. 13A shows specific activity of Hex activity (MUG-degrading activity) in each organ 10 weeks after single administration of AAV-CMV-modHEXB at $1.15\times10^{11}$ vg/mouse to the brain ventricle or the temporal vein of Sandhoff disease heterozygous (Hexb+/−) newborn (P0 to P2) mice.

FIG. 13B shows specific activity of Hex activity (MUG-degrading activity) in each organ 10 weeks after single administration of AAV-CMV-modHEXB at $1.15\times10^{10}$ vg/mouse to the brain ventricle or the temporal vein of Sandhoff disease heterozygous (Hexb+/−) newborn (P0 to P2) mice.

8. Evaluation of Effects on Retention of Motor Functions, Maintenance of Body Weight, and Prolongation of Survival Time Via Single Administration of AAV-CMV-modHEXB to the Brain Ventricle or the Temporal Vein of Sandhoff Disease (Hexb−/−) Newborn (P0 to P2) Mice After single administration of AAV-CMV-modHEXB to the brain ventricle or the temporal vein of SD mice, coordinated motor functions were evaluated by the rotarod performance test.

AAV-CMV-modHEXB was administered once at $1.15\times10^{10}$ vg/5 l PBS (phosphate buffer) to the brain ventricle or the temporal vein of newborn SD mice (P0 to P1), and the mice were subjected to the rotarod performance test every week starting at the age of 11 weeks.

The rotarod performance test was initiated at 4 round-per-minutes (rpm), the number of revolution was increased to 40 rpm in 120 seconds, each mouse was subjected to the test 6 times, and the average time until the mice fell from the rotarod was measured. The wild-type mice (WT) and the SD mice (SD) of the same age were subjected to the test under the same conditions. A practice test was performed 1 week before the actual test.

Body weight was measured and survival (survival time) was inspected at each time point.

Figure 14A:
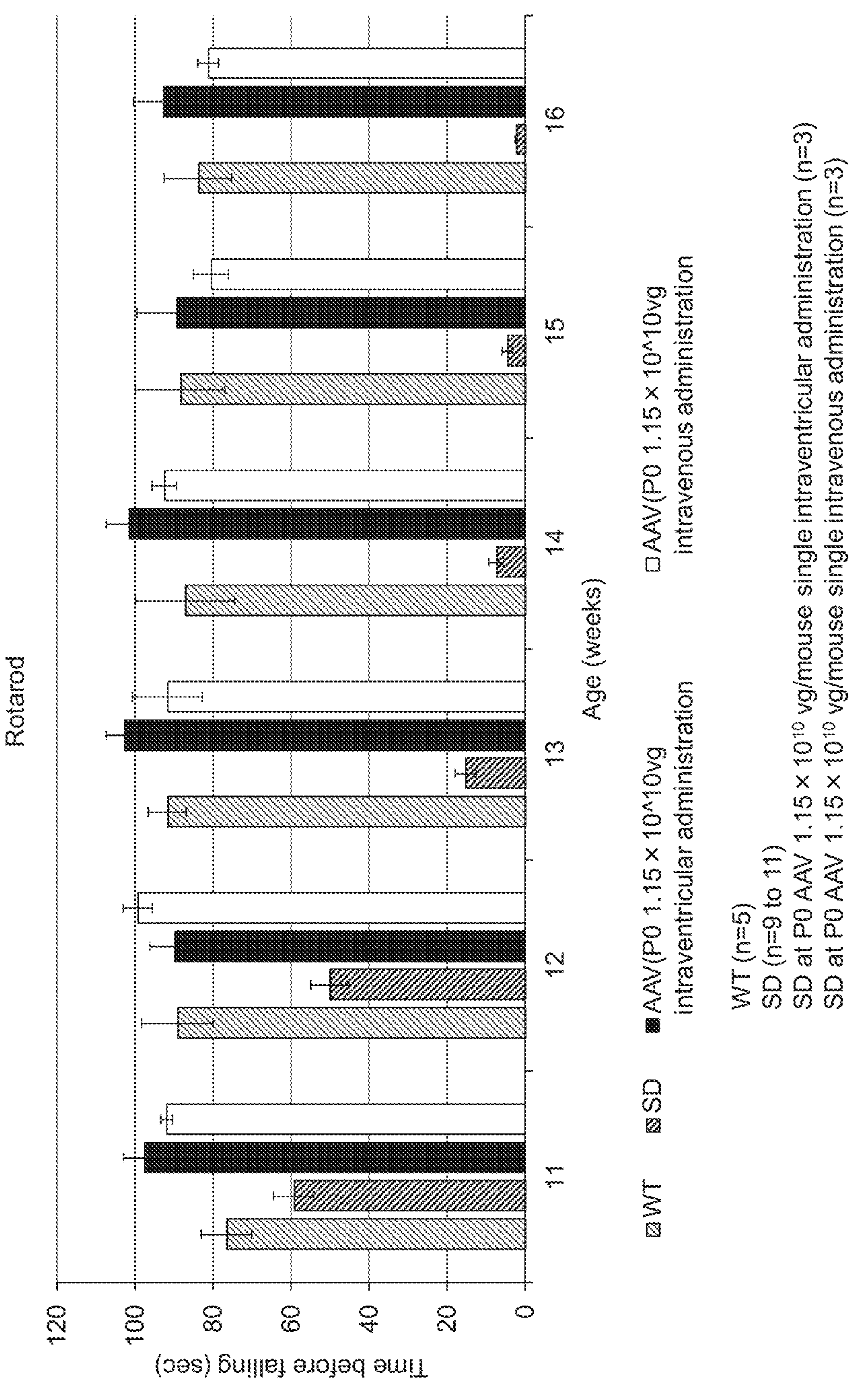
FIG. 14A shows the results of the rotarod performance test performed in Example 1, Experiment 8.
Figure 14B:
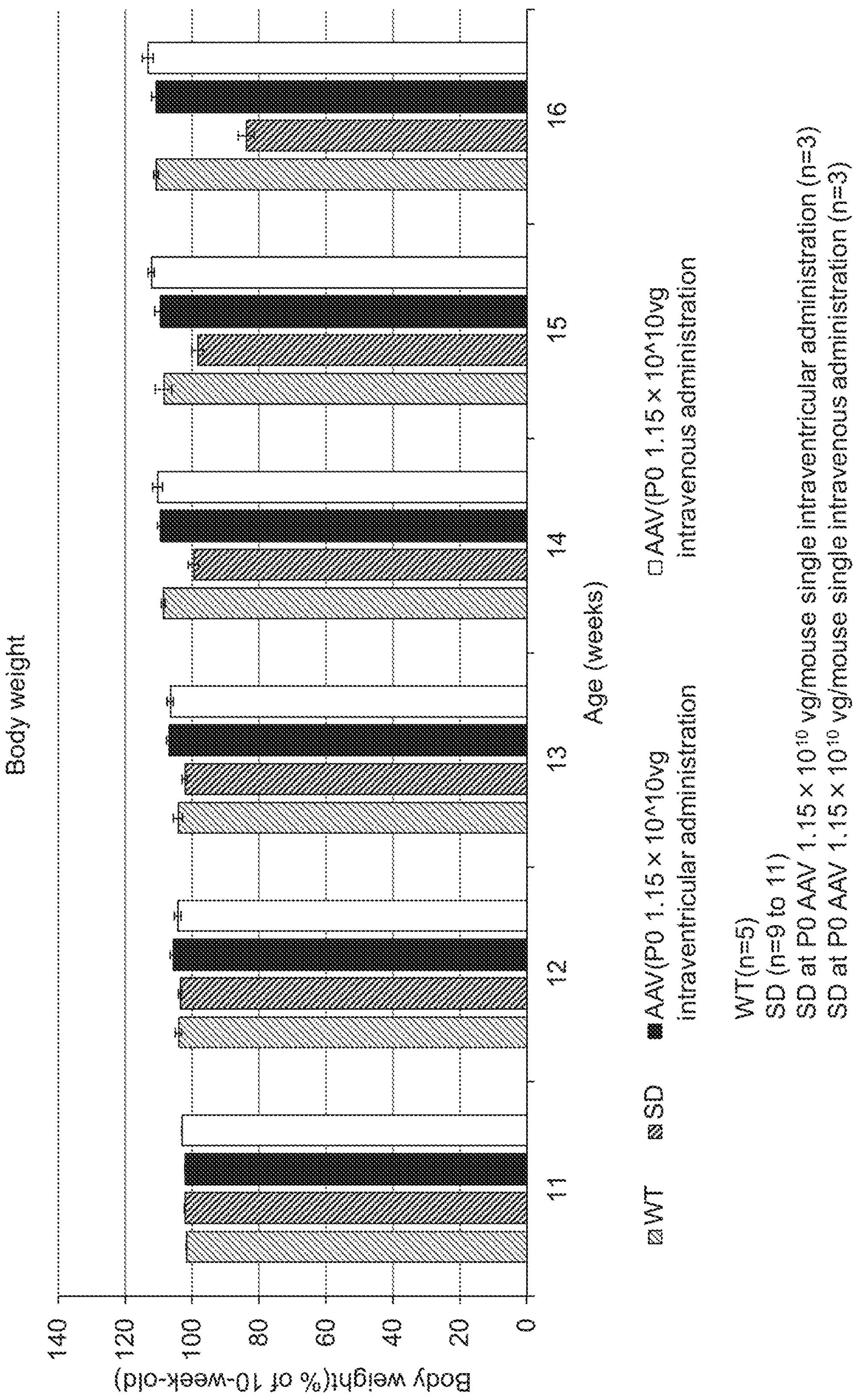
FIG. 14B shows the results of measurement of body weight performed in Example 1, Experiment 8.

FIG. 14A shows the results of measurement of the time until the mice fell in the rotarod performance test starting at the age of 11 weeks (coordinated motor functions) when AAV-CMV-modHEXB was administered once at $1.15\times10^{10}$ vg/mouse to the brain ventricle or the temporal vein of the Sandhoff disease (Hexb−/−) newborn mice (P0). FIG. 14B shows the results of measurement of body weight starting at the age of 10 weeks (the body weight at the age of 10 weeks: 100). As a result of single administration of AAV-CMV-modHEXB to the brain ventricle or the temporal vein of the SD mice, coordinated motor functions and body weight were maintained at the levels equivalent to those of the wild-type mice. While the SD mice to which AAV-CMV-modHEXB had been administered survived up to the age of 15 weeks, they died at the age of 16 weeks.

Example 2: Evaluation of Effects of Administration of AAV-CMV-modHEXB and AAV-SynI-modHEXB on Neural Cells Induced to Differentiate from iPS Cells of Patients with Tay-Sachs Disease and Cultured Human Neural Cells of Sandhoff Disease Models 1. Evaluation of effects of administration of AAV-CMV-modHEXB and AAV-SynI-modHEXB on neural cells induced to differentiate from iPS cells of patients with Tay-Sachs disease In accordance with the method reported in Kondo T. et al., Cell Stem Cell 12 (4): 487-496, 2013, neural cells were induced to differentiate from iPS cells of patients with Tay-Sachs disease (TSD) (TSD iPS cells). A given number of TSD iPS cells were subjected to float culture in DFK 5% DS medium supplemented with dorsomorphin, SB431542, and non-essential amino acids (NEAA) for 8 days, the cultured cells were subjected to adhesion culture in DFN2D medium supplemented with N2 supplement, dorsomorphin, and NEAA for 16 days, the cultured cells were further subjected to adhesion culture in NB27full medium supplemented with neurotrophic factors; BDNF, GDNF, and NT-3, and B-27 Supplement (free of vitamin A and glutamax) for 25 days or longer, the cultured cells were subjected to passage culture, and the resultants were then subjected to the experiment of AAV-CMV-modHEXB and AAV-SynI-modHEXB administration.

Figure 15:
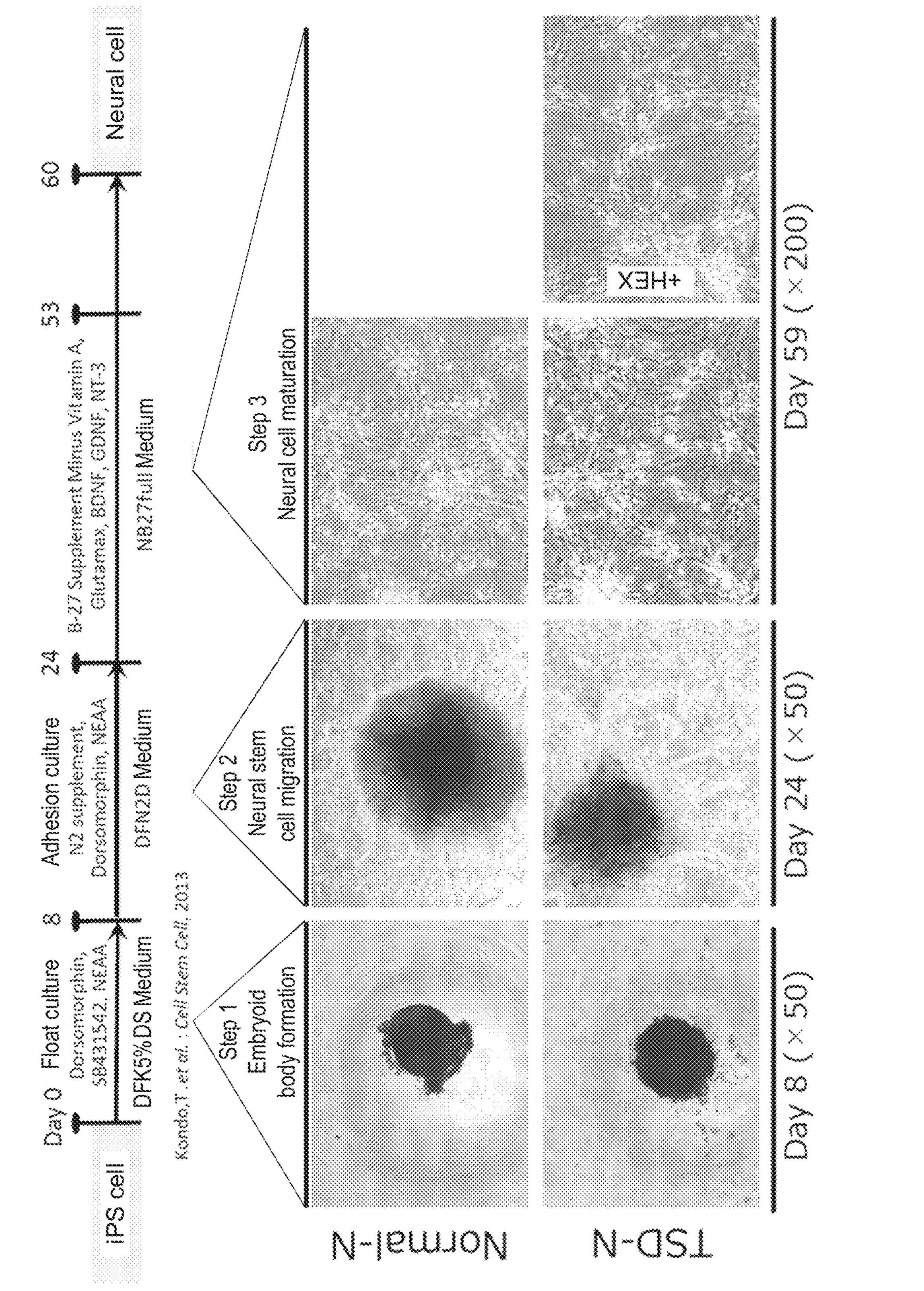
FIG. 15 shows a summary of induction of differentiation of iPS cells into neural cells.

FIG. 15 shows a summary of induction of iPS cells to differentiate into neural cells.

For immunocytochemical experiments, neural cells derived from healthy subjects and from TSD iPS cells sown on 8-well chamber slides were fixed in a 4% paraformaldehyde/PBS solution at room temperature for 1 hour. The slides were washed with PBS and subjected to blocking using 5% goat serum/PBS at room temperature for 1 hour.

1.1. Examination of Neural Cell Marker Expression and GM2 Ganglioside Accumulation In order to examine whether or not GM2 ganglioside (GM2) had been accumulated in the neural cells that had been induced to differentiate from the TSD iPS cells or iPS cells derived from healthy subjects, the cells were treated with the anti-GM2 mouse monoclonal IgM antibody (a 100-fold dilution) at 4° C. overnight.

As human neural cell markers, primary antibodies reacting with β-tubulin III (neurons), TBR1 (the cerebral cortex neurons), A2B5 (glial progenitor cells), and GFAP (astrocytes) were used. As secondary probes, biotin-labeled anti-mouse IGG+M antibody and the Cy3-labeled anti-rabbit IgG antibody were used. As a tertiary probe, FITC-streptavidin was used, and Hoechst 33258 was used for nuclear fluorostaining. Immunofluorescence was observed under a confocal laser scanning microscope (ZeissLSM700).

Figure 16:
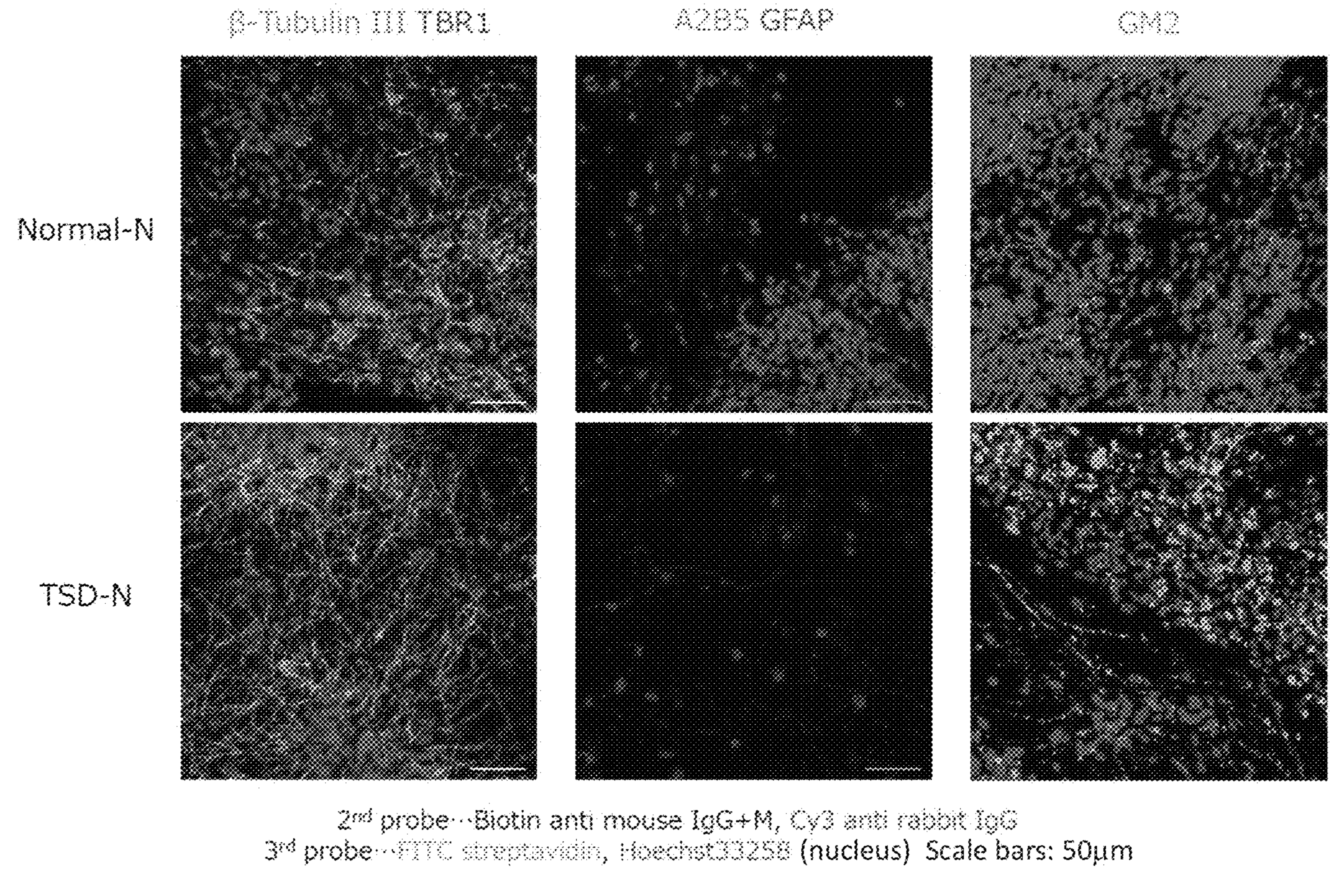
FIG. 16 shows the results of Example 2, Experiment 1.1.

The results are shown in FIG. 16. In the figure, each scale bar indicates 50 μm. Both the neural cells induced to differentiate from the TSD iPS cells (TSD-N) and the neural cells induced to differentiate from iPS cells derived from healthy human subjects (Normal-N) were positive for immunofluorescences β-tubulin III, TBR1, A2B5, and GFAP. While TSD-N was strongly positive for immunofluorescence of GM2 ganglioside, Normal-N was slightly positive for GM2 ganglioside. Thus, both the neural cells induced to differentiate from the TSD iPS cells (TSD-N) and the neural cells induced to differentiate from iPS cells derived from healthy human subjects (Normal-N) were found to each constitute a group of cells positive for neural cell markers. In TSD-N, accumulation of GM2 ganglioside was observed.

1.2. Introduction of modHexB into the Neural Cells Derived from the iPS Cells of the Patient with Tay-Sachs Disease (TSD-N) Using AAV-SynI-modHEXB and AAV-CMV-modHEXB For determining dose dependency of modHexB gene introduction into the neural cells derived from the iPS cells of the patient with Tay-Sachs disease via administration of AAV-SynI-modHEXB and AAV-CMV-modHEXB (79 days after the initiation of differentiation induction, Day 79), $0.1\times10^6$, $0.5\times10^6$, and $1.0\times10^6$ vg the AAV vector were administered to culture solutions per cell cultured on poly-ornithine/laminin-coated dishes, the culture solutions 7 days later (Day 86) were collected, the cells were washed and harvested, and the cell extracts were prepared.

Recovery of Hex activity was evaluated using artificial fluorescent substrates. Also, protein concentration in the extract was assayed, and enzyme specific activity was determined.

As artificial fluorescent substrates, 4-methylumbelliferyl β-D-glucosaminide (MUG) and 4-methylumbelliferyl 6-sulfo-β-D-glucosaminide (MUGS) were used. In general, cells lacking the Hex a subunit does not have MUGS-degrading activity, and cells lacking the Hex P subunit does not have MUG-degrading activity.

Figure 17:
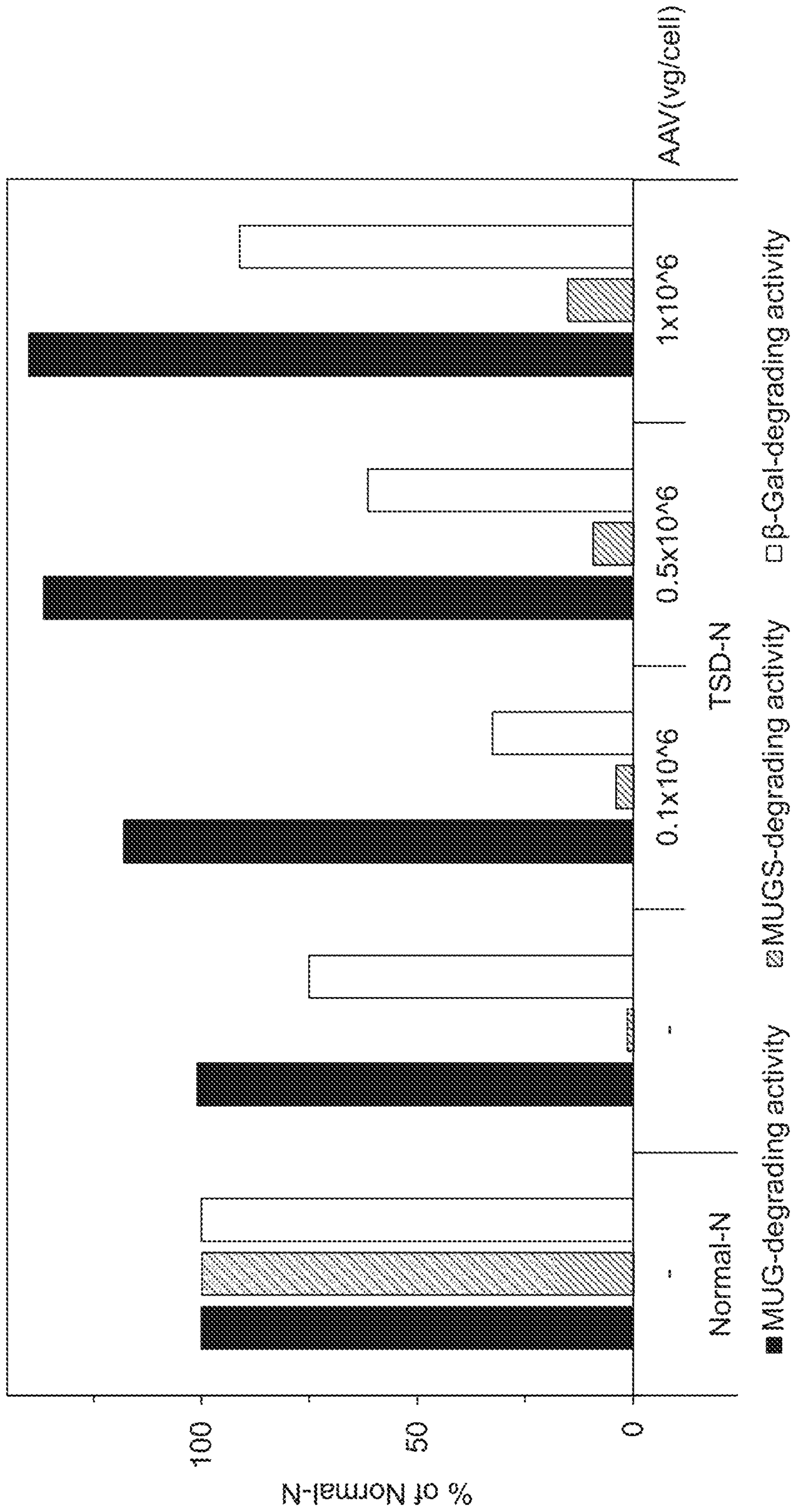
FIG. 17 shows the results of Example 2, Experiment 1.2.

FIG. 17 shows the results of analysis of effects of modHexB introduction into TSD-N using AAV-SynI-modHEXB and dose dependency (recovery of the lost Hex activity). FIG. 17 shows MUG-degrading activity, MUGS-degrading activity, and β-GAL-degrading activity in TSD-N treated with AAV-SynI-modHEXB at different doses relative to activity in Normal-N designated as 100%, which had been subjected to the same treatment. When TSD-N was treated with AAV-SynI-modHEXB at $1.0\times10^6$ vg/cell, MUGS-degrading activity was slightly recovered (15% relative to Normal-N).

Figure 18:
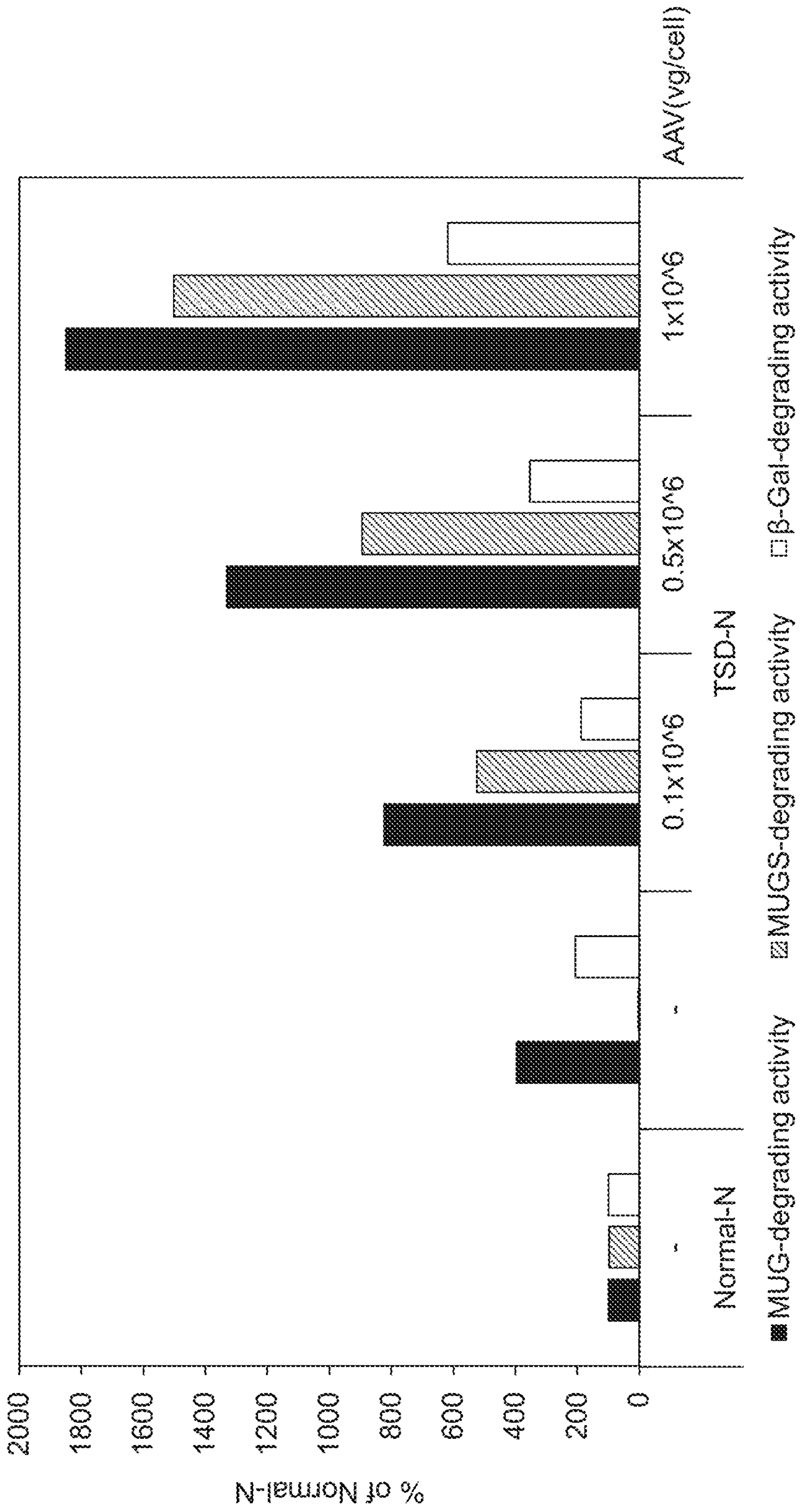
FIG. 18 shows the results of Example 2, Experiment 1.2.

FIG. 18 shows the results of analysis of effects of modHexB introduction into TSD-N using AAV-CMV-modHEXB and dose dependency (recovery of the lost Hex activity). FIG. 18 shows MUG-degrading activity, MUGS-degrading activity, and β-GAL-degrading activity in TSD-N treated with AAV-CMV-modHEXB at different doses relative to activity in Normal-N designated as 100%, which had been subjected to the same treatment. When TSD-N was treated with AAV-CMV-modHEXB at $0.1\times10^6$ vg/cell, MUGS-degrading activity was significantly recovered.

2. Evaluation of Effects of AAV-CMV-modHEXB and AAV-SynI-modHEXB Administration on Cultured Human Neural Cells of Sandhoff Disease Models Prepared Via Genome Editing 2.1. Preparation of Cultured Human Neural Cells of Sandhoff Disease Models Via Genome Editing The human HEXB knockout vector was prepared by designating the genome sequence: CGGCTTGGCCGAGACGCTCG, in Exon 1 of HEXB as a target sequence and using the GeneArt™ CRISPR Nuclease Vector with OFP Reporter Kit (Invitrogen #A21174). The vector was transfected into the human neuroblastoma; i.e., the SH-SY5Y cell line, via lipofection to perform HEXB KO via genome editing using the CRISPR/Cas9 system.

The SH-SY5Y cells into which the HEXB knockout vector had been introduced were subjected to FACS to sort OFP-expressing cells (CAS9-expressing cells), and maintenance culture was performed using DMEM/F12+10% FBS, 70 μg/100 μg/ml penicillin G/streptomycin medium. Through limiting dilution, defective strains having activity of degrading an artificial fluorescent substrate (MUG), which was decreased to 2% or lower of that of the parent strain, were selected.

The HEXB KO SH-SY5Y cells and the parent strain were fixed in a 4% paraformaldehyde/PBS solution at room temperature for 1 hour. The resultant was washed with PBS and subjected to blocking using 5% goat serum/PBS at room temperature for 1 hour. The accumulated substrate; i.e., GM2 ganglioside (GM2), was treated with the anti-GM2 mouse monoclonal IgM antibody (a 100-fold dilution) at 4° C. overnight. The resultant was washed, treated with a secondary antibody; i.e., the Cy3-labeled anti-rabbit IgG antibody, and Hoechst 33258 was used for nuclear fluorostaining. After washing, the resultant was enclosed in 50% glycerol/PBS, and immunofluorescence was observed under a confocal laser scanning microscope (ZeissLSM700).

Figure 19:
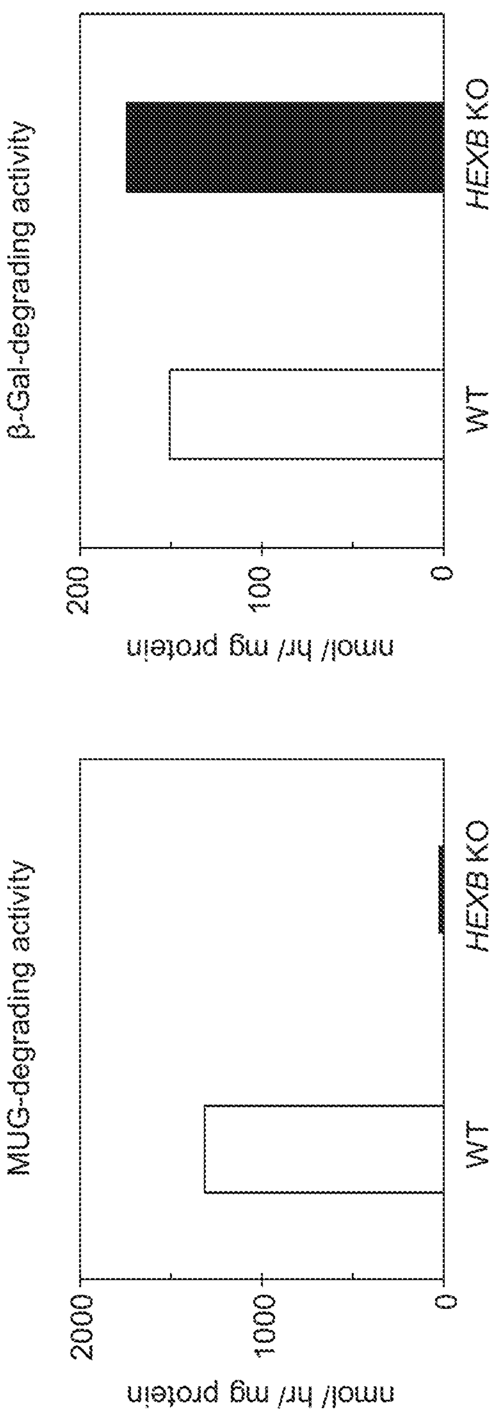
FIG. 19 shows the results of Example 2, Experiment 2.1.

FIG. 19 shows MUG-degrading activity and β-Gal-degrading activity (specific activity per unit protein amount) of the HEXB KO SH-SY5Y cells (HEXB KO) and the wild-type parent strain (WT).

Figure 20:
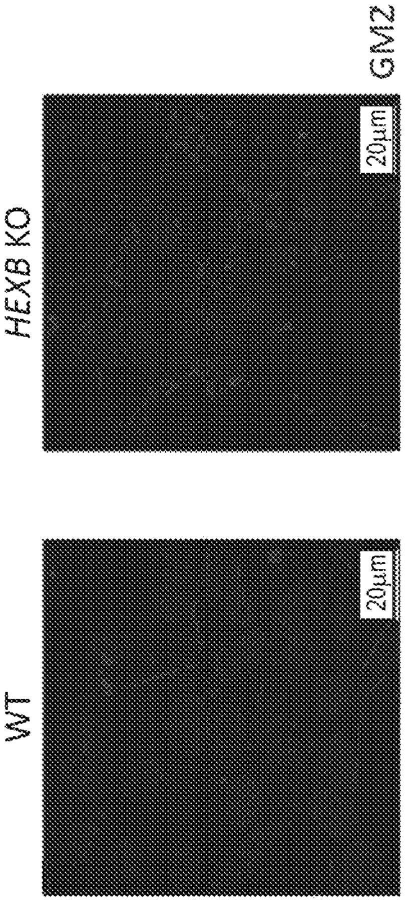
FIG. 20 shows the results of Example 2, Experiment 2.1.

FIG. 20 shows images of immunofluorescent observation of the HEXB KO SH-SY5Y cells (HEXB KO) and the wild-type parent strain (WT) in which GM2 ganglioside and cell nuclei were shown in red and blue respectively. The both images of observation of HEXB KO and WT shown in FIG. 20 include cell nuclei (blue). While the HEXB KO cells were shown to be strongly positive for GM2 ganglioside (red) immunofluorescence, the WT cells were shown to be slightly positive for GM2 ganglioside (red) immunofluorescence.

In the HEXB KO SH-SY5Y cells (HEXB KO), MUG-degrading activity lowered to approximately 2% that of the wild-type parent strain (WT) and accumulation of the substrate (GM2 ganglioside) were observed.

2.2. Induction of Differentiation of HEXB KO SH-SY5Y Cells into Neural Cells

HEXB KO SH-SY5Y cells (HEXB KO) were cultured in the presence of DMEM/F12+3% FBS, 70 μg/100 μg/ml penicillin G/streptomycin, and g/ml retinoic acid for 10 days or longer to induce the HEXB KO cells to differentiate into neural cells.

The differentiated neural cells were fixed in a 4% paraformaldehyde/PBS solution at room temperature for 1 hour. The fixed cells were washed in PBS and subjected to blocking with 5% goat serum/PBS at room temperature for 1 hour. The cells were treated with the primary antibodies reacting with Nestin (neural stem cell marker), PSA-NCAM (neural progenitor cell marker), and β-Tubulin III and NF-L (neuron) at 4° C. overnight. As a secondary probe, the Cy3-labeled anti-rabbit IgG antibody was used, and Hoechst 33258 was used for nuclear fluorostaining. After washing, the resultant was enclosed in 50% glycerol/PBS, and immunofluorescence was observed under a confocal laser scanning microscope (ZeissLSM700).

Figure 21:
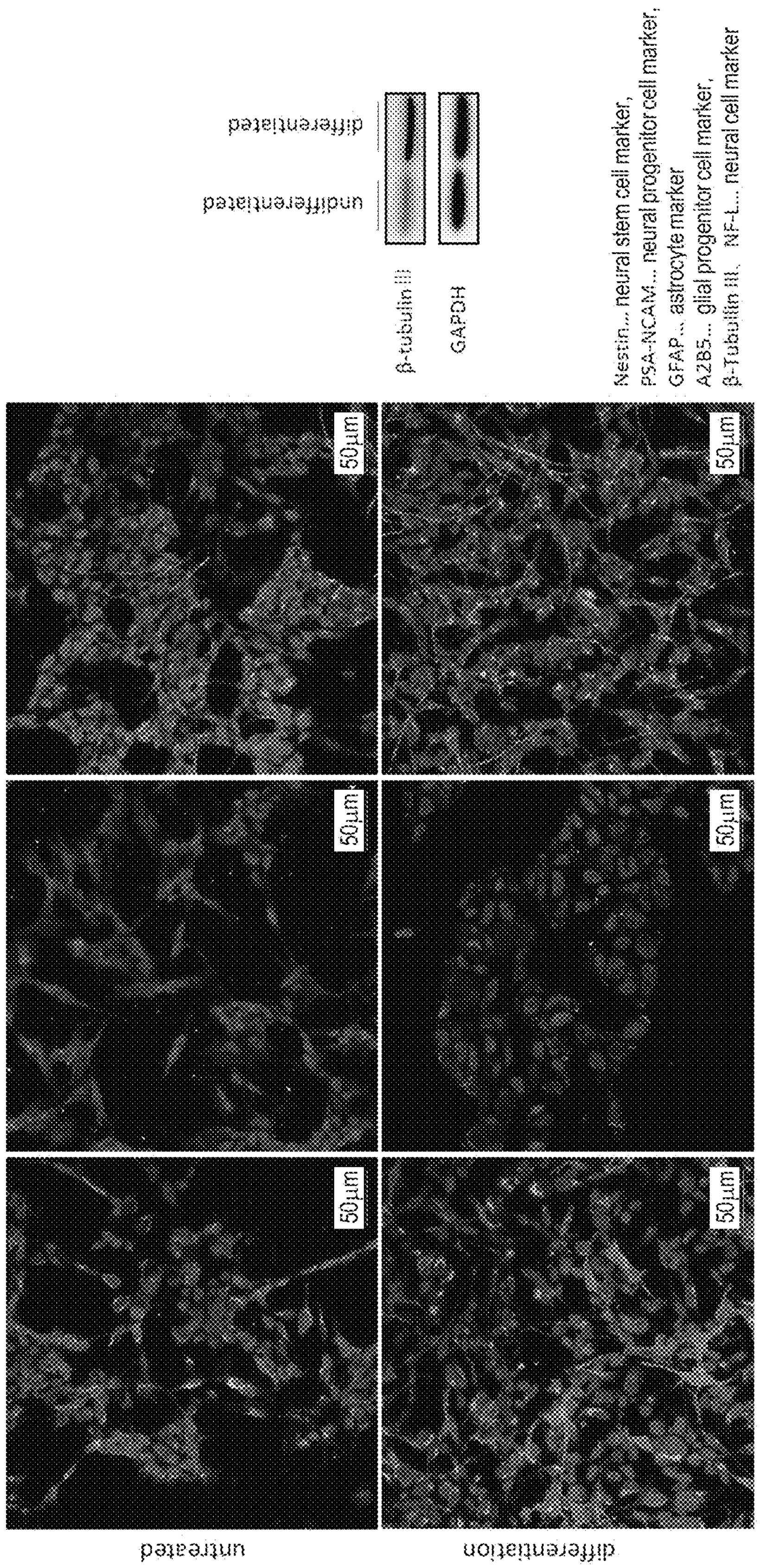
FIG. 21 shows the results of Example 2, Experiment 2.2.

FIG. 21 shows the results of immunofluorescent observation of the HEXB KO SH-SY5Y cells (HEXB KO) before differentiation induction (untreated, undifferentiated) and 12 days after the initiation of culture in a differentiation induction medium (differentiated). In FIG. 21, the HEXB KO cells before differentiation induction (untreated, undifferentiated) were positive for Nestin, positive for PSA-NCAM, positive for GFAP, slightly positive for A2B5, slightly positive for NF-L, slightly positive for β-Tubulin III, and positive for Hoechst 33258. In contrast, the HEXB KO cells 12 days after the initiation of culture in a differentiation induction medium (differentiated) were positive for Nestin, positive for PSA-NCAM, positive for GFAP, slightly positive for A2B5, strongly positive for NF-L, strongly positive for β-Tubulin III, and positive for Hoechst 33258. Specifically, expression of mature neural cell markers, such as NF-L and β-tubulin III, was enhanced as a result of differentiation induction.

2.3. modHexB Introduction into Human HEXBKO Cultured Neural Cells Using AAV-CMV-modHEXB and AAV-SynI-modHEXB Dose dependency of single administration of AAV-CMV-modHEXB and AAV-SynI-modHEXB into cultured human neural cells HEXB KO SH-SY5Y was determined by administering the AAV vector at $0.1\times10^5$, $0.5\times10^5$, $1\times10^5$, and $1.0\times10^6$ vg/cell to the human HEXB KO cultured neural cells (SH-SY5Y cells, $1.0\times10^6$ cells) 8 days after differentiation induction, collecting the culture supernatant and the cells 7 days later, preparing cell extracts, and evaluating development of Hex activity using artificial fluorescent substrate MUG inside and outside the cells. Also, protein concentration in the cell extracts was assayed, and enzyme specific activity was determined.

Figure 22:
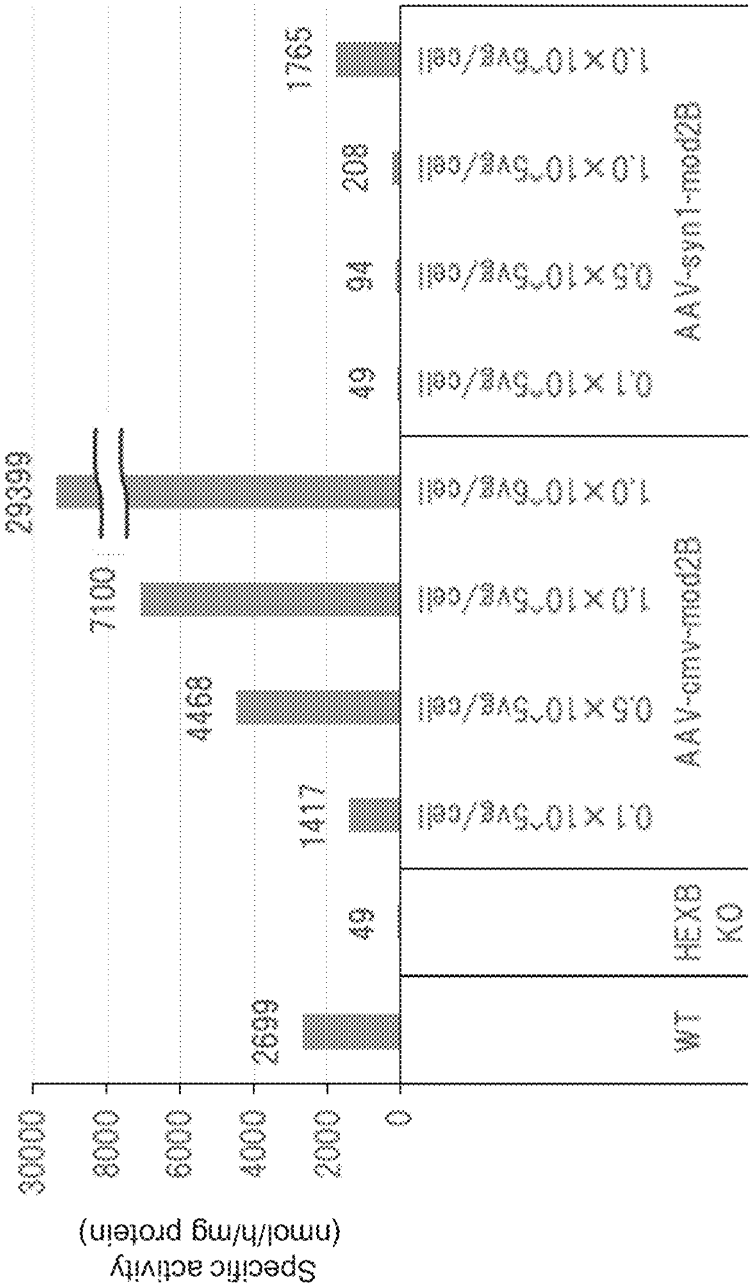
FIG. 22 shows the results of Example 2, Experiment 2.3.

FIG. 22 shows MUG-degrading specific activity (Hex activity) inside the cultured human neural cells HEXB KO SH-SY5Y (the cell extract) treated with the AAV vectors at different doses. AAV-CMV-modHEXB exhibited higher expression efficiency than AAV-SynI-modHEXB.

Figure 23:
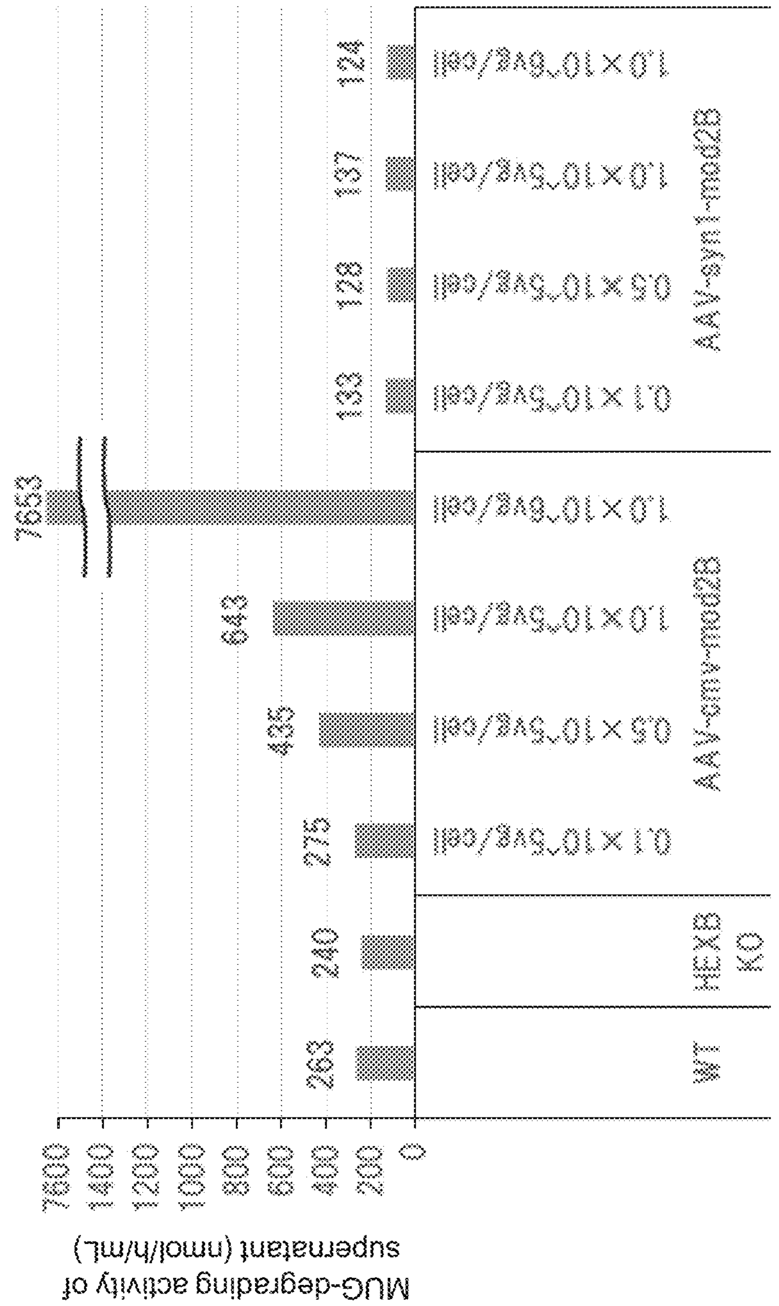
FIG. 23 shows the results of Example 2, Experiment 2.3.

FIG. 23 shows MUG-degrading specific activity (Hex activity) outside the cultured human neural cells HEXB KO SH-SY5Y (the culture supernatant) treated with the AAV vectors at different doses. It was found that AAV-CMV-modHEXB would exhibit higher expression efficiency than AAV-SynI-modHEXB and that the expressed modHexB was secreted extracellularly.

2.4. Western Blot Analysis of modHexB Secreted Extracellularly

The AAV-CMV-modHEXB vectors obtained in Experiment 2.3. above were administered at relevant doses to cultured human neural cells HEXB KO SH-SY5Y, a given amount of the protein in the culture supernatant (10 μg each) 7 days later was subjected as a sample to SDS-PAGE involving the use of 10% polyacrylamide gel, and human modHexB was subjected to Western blot analysis. After electrophoresis, the gel was transcribed to a PVDF membrane at a constant voltage, and the membrane was treated with a blocking agent for 1 hour. The resultant was treated with the anti-human HexA (αβ) rabbit polyclonal antibody NAG (A) as a primary antibody (a 1,000-fold dilution) at 4° C. overnight, washed with a Tris buffer, treated with the peroxidase-labeled anti-rabbit IgG antibody as a secondary antibody, washed, and subjected to detection of the human modHexB-derived protein using a chemiluminescence kit (ECLplus) and LAS4000mini (GEHealthcare).

Figure 24:
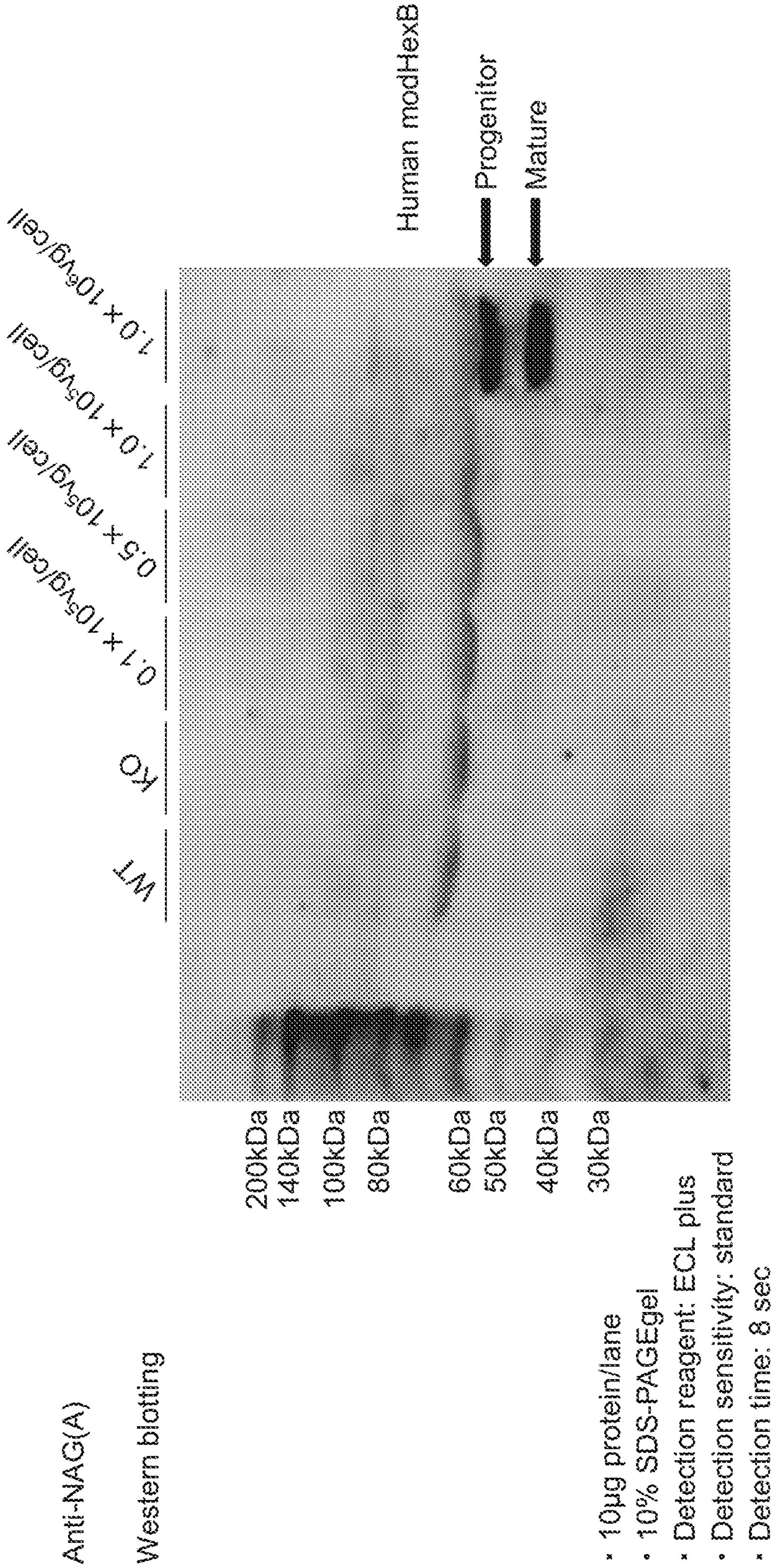
FIG. 24 shows the results of Example 2, Experiment 2.4.

FIG. 24 shows the results of Western blot analysis. It was confirmed that the modHEXB gene product introduced into the human neural cells was secreted extracellularly as a progenitor protein.

3. Summary of Example 2

As a result of gene introduction using AAV-SynI-modHEXB comprising the modHEXB gene ligated to a region downstream of the neural cell-specific expression promoter, MUGS-degrading activity in the neural cells derived from the iPS cells of the patient with Tay-Sachs disease and MUG-degrading activity in the cultured human neuroblastoma SH-SY5Y HEXB KO of Sandhoff disease model were slightly recovered.

When AAV-CMV-modHEXB comprising the modHEXB gene ligated to a region downstream of the ubiquitous expression promoter (CMVP) was used, MUGS-degrading activity in the neural cells derived from the iPS cells of the patient with Tay-Sachs disease and MUG-degrading activity in the cultured human neuroblastoma SH-SY5Y HEXB KO of Sandhoff disease model were significantly recovered.

When AAV-CMV-modHEXB was administered to the cultured human neuroblastoma SH-SY5Y HEXB KO of Sandhoff disease model at $1\times10^6$ vg/cell, the recombinant human modHexB progenitor protein expressed in the neural cells was secreted extracellularly. Thus, this suggests cross-correction effects.

Example 3: Preparation of AAV-CMV-modHEXB (1) Modification of AAV Coat (Capsid) Protein VP1

Concerning type 9AAV (AAV9), the pAAV9-RC plasmid comprising a nucleotide sequence encoding the coat protein VP1 was used as a template. This plasmid is derived from AAV3 Rep/VP described in the literature (Handa et al., J. Gen. Virol., 81: 2077-2084, 2000) and comprises the AAV3 Rep sequence (Muramatsu et al., Virology 221, 208-217, 1996). The nucleotide sequence of AAV9 VP1 has already been registered under Accession No. AY530579 at GenBank (shown in SEQ ID NO: 5). The primers shown below were synthesized, and tyrosine (Y) at position 446 in the amino acid sequence of AAV9 VP1 (SEQ ID NO: 6) was substituted with phenylalanine (F) using the Quick Change II XL site-directed mutagenesis kit (Stratagene). The pAAV9-yfRC plasmid comprising a polynucleotide encoding the substituted amino acid sequence AAV9-yfVP1-3 (SEQ ID NO: 12) was prepared. pAAV9-yfRC comprises the nucleotide sequence encoding AAV2 Rep (SEQ ID NO: 15).

```
yfAAV9-F:
                                    (SEQ ID NO: 21)
5'-CGACCAATACTTGTACTTTCTCTCAAAGAC-3'

yfAAV9-R:
                                    (SEQ ID NO: 22)
3'-GCTGGTTATGAACATGAAAGAGAGTTTCTG-5'
```

(2) Preparation of rAAV Vector (a) Preparation of Vector Genome Plasmid

The pAAV-CMV-modHEXB plasmid comprising, between hairpin DNA sequences referred to as 5'- and 3'-inverted terminal repeat inverted terminal repeats (ITRs) of the pAAV3 plasmid comprising the DNA sequence of type 3AAV (AAV3), a DNA sequence comprising the CMV promoter, the first intron of the human growth hormone (hGH), modHEXB (DNA encoding the amino acid sequence as shown in SEQ ID NO: 25), WPRE (the woodchuck hepatitis virus post-transcriptional regulatory element), and the SV40 polyadenylation sequence inserted in that order from the 5' terminus toward the 3' terminus was prepared. SEQ ID NO: 26 shows the nucleotide sequence of the expression cassette from 5' ITR to 3' ITR of pAAV-CMV-modHEXB. In the nucleotide sequence as shown in SEQ ID NO: 26, a region of nucleotides 1 to 146 constitutes the 5' ITR, a region of nucleotides 382 to 951 constitutes the CMV promoter sequence, a region of nucleotides 1049 to 1369 constitutes the first intron sequence of hGH, a region of nucleotides 1428 to 3026 constitutes the modHEXB sequence, a region of nucleotides 3046 to 3634 constitutes the WPRE sequence, a region of nucleotides 3728 to 3862 constitutes the SV40 polyadenylation sequence, and a region of nucleotides 3939 to 4083 constitutes the 3' ITR sequence. The basic structure of this plasmid is described in Li et al., Mol. Ther., 13: 160-166, 2006.

(b) Transfection into HEK293 Cell

<Day 1>

The HEK293 cells ($1.5\times10^6$ cells) were seeded in a 225-$cm^2$ flask and cultured in 10% FCS-DMEM/F12 medium in the presence of 5% $CO_2$ at 37° C.

<Day 3>

Transfection was performed by the calcium phosphate method.

The AAV helper plasmid (pAAV9-yfRC), the AAV vector genome plasmid (pAAV-CMV-modHEXB), and the helper plasmid comprising the nucleotide sequence of Adenovirus (AdV) (pHelper, AAV Helper-Free System, Catalog No. 240071, Agilent Technologies) (25 μg each, 75 μg in total) were mixed with each other in 0.3 M $CaCl_2$).

Thereafter, 2×HBS (80 mM NaCl, 50 mM Hepes buffer, 1.5 mM $Na_2HPO_4$, pH 7.10) was added to prepare DNA-calcium phosphate. The culture medium in the flask was replaced with a medium supplemented with DNA-calcium phosphate, culture was conducted for several hours, and the medium was then replaced with a fresh medium.

<Day 6>

The virus virions (rAAV virions) were collected. The cells were peeled from the culture dish with the addition of 0.5 M EDTA and suspended in TBS (100 mM Tris HCl, pH 8.0, 150 mM NaCl). With the use of a dry ice-ethanol bath and a water bath (37° C.), a freeze-thaw process was repeated 3 times to disrupt the cells. Following centrifugation at 10,000×g for 10 minutes, the supernatant was collected, and coarse debris was removed.

(c) Preparation of Virus Vector

In accordance with the procedure described below, ultracentrifugation was performed by cesium chloride CsCl density gradient to purify the rAAV vector. In the ultracentrifugation tube, 1.5 M CsCl and 1.25 M CsCl were superposed to prepare density gradient. After the cell debris solution containing the rAAV vector was superposed, ultracentrifugation was performed at 30,000 rpm for 2.5 hours. The refractive index (RI) was measured and a fraction containing the rAAV vector with RI of 1.365 to 1.380 was collected. This fraction was superposed again on the CsCl solution, and ultracentrifugation was performed at 36,000 rpm for 2.5 hours to obtain a fraction containing rAAV.

(d) Measurement of Virus Vector Titer (Real-Time PCR)

A serial dilution series of $10^{-2}$ to $10^{-6}$ of purified rAAV was prepared. Quantification was carried out with the use of a set of primers involving the use of the WPRE sequence as the standard and the Applied Biosystems 7900HT Fast Real-time PCR System (Applied Biosystems).

Example 4: Preparation of AAV-SynI-modHEXB

AAV-SynI-modHEXB was prepared in the same manner as the method for preparation of AAV-CMV-modHEXB described in Example 3, except for the use of the vector genome plasmid comprising an expression cassette modified from the expression cassette of AAV-CMV-modHEXB by substitution of the CMV promoter sequence composed of nucleotides 382 to 951 in the nucleotide sequence as shown in SEQ ID NO: 26 with the SynI promoter sequence as shown in SEQ ID NO: 23.

Example 5: Preparation of AAV-CMV-GFP

AAV-CMV-GFP was prepared in the same manner as the method for preparation of AAV-CMV-modHEXB described in Example 3, except for the use of the vector genome plasmid comprising an expression cassette modified from the expression cassette of AAV-CMV-modHEXB by substitution of the modHEXB sequence composed of nucleotides 1428 to 3026 in the nucleotide sequence as shown in SEQ ID NO: 26 with the known GFP sequence.

Example 6: Administration of AAV-CMV-modHEXB to Crab-Eating Macaque

AAV-CMV-modHEXB prepared in the manner described in Example 3 was administered once intraspinally to five 2-week-old healthy crab-eating macaques (*Macaca fascicularis*) at $2.0\times10^{12}$ vg per kg of body weight. The 5 individuals were designated as Identification Numbers: #1 to #5. These individuals were observed for 3 months after administration, and no adverse effects were observed in terms of appetite, body weight, and behavior.

(Preparation of Tissue Extract)

Tissues indicated below were extracted 3 months after administration.

Parietal cortex
Temporal cortex
Entothinal cortex
Hippocampus
Putamen
Cerebellum
Brain stem
Cervical spinal cord (C4-C6)
Thoracic spinal cord (Th6-Th8)
Lumber spinal cord (L2-L4)
Heart
Lung
Liver
Spleen
Kidney 300 µl of ultrapure water was added based on 100 mg each of the wet tissue, and ultrasonic disintegration treatment involving the use of an ultrasonic disintegrator for 2 minutes was repeated 10 times to obtain a cell debris solution.

Subsequently, the cell debris solution was ultrasonically treated using an ultrasonic washing apparatus (water bath) for 10 minutes.

The resulting debris solution was centrifuged at 4° C. and 12,000×g for 15 minutes, and the supernatant was collected as an enzyme activity assay sample (tissue extract).

(Assay of Hex Activity of Tissue Extract)

A given amount each of the tissue extracts was subjected to assays of activity of degrading artificial fluorescent substrates; i.e., 4-methylumbelliferyl (3-D-glucosaminide (MUG) and 4-methylumbelliferyl 6-sulfo-β-D-glucosaminide (MUGS). Also, protein concentration in the tissue extracts was assayed, and substrate-degrading activity per unit protein amount; i.e., specific activity, was determined.

Substrate-degrading activity was assayed by subjecting a given amount of the tissue extract adequately diluted with ultrapure water and a MUG or MUGS solution to incubation at 37° C. for 30 minutes, adding 370 µl of 0.2 M glycine-NaOH (pH 10.7) to terminate the reaction, fractionating the solution at 200 µl/well to a 96-well plate, and performing fluorescent assay (excitation: 355 nm; detection: 460 nm). In order to prepare a calibration curve, 4-MU (4-methylumbelliferone) diluted to 0.5 nmol to 5 nmol in 0.2 M glycine-NaOH (pH 10.7) was also fractionated at 200 µl/well to a 96-well plate, and fluorescent assay was performed.

Figure 25:
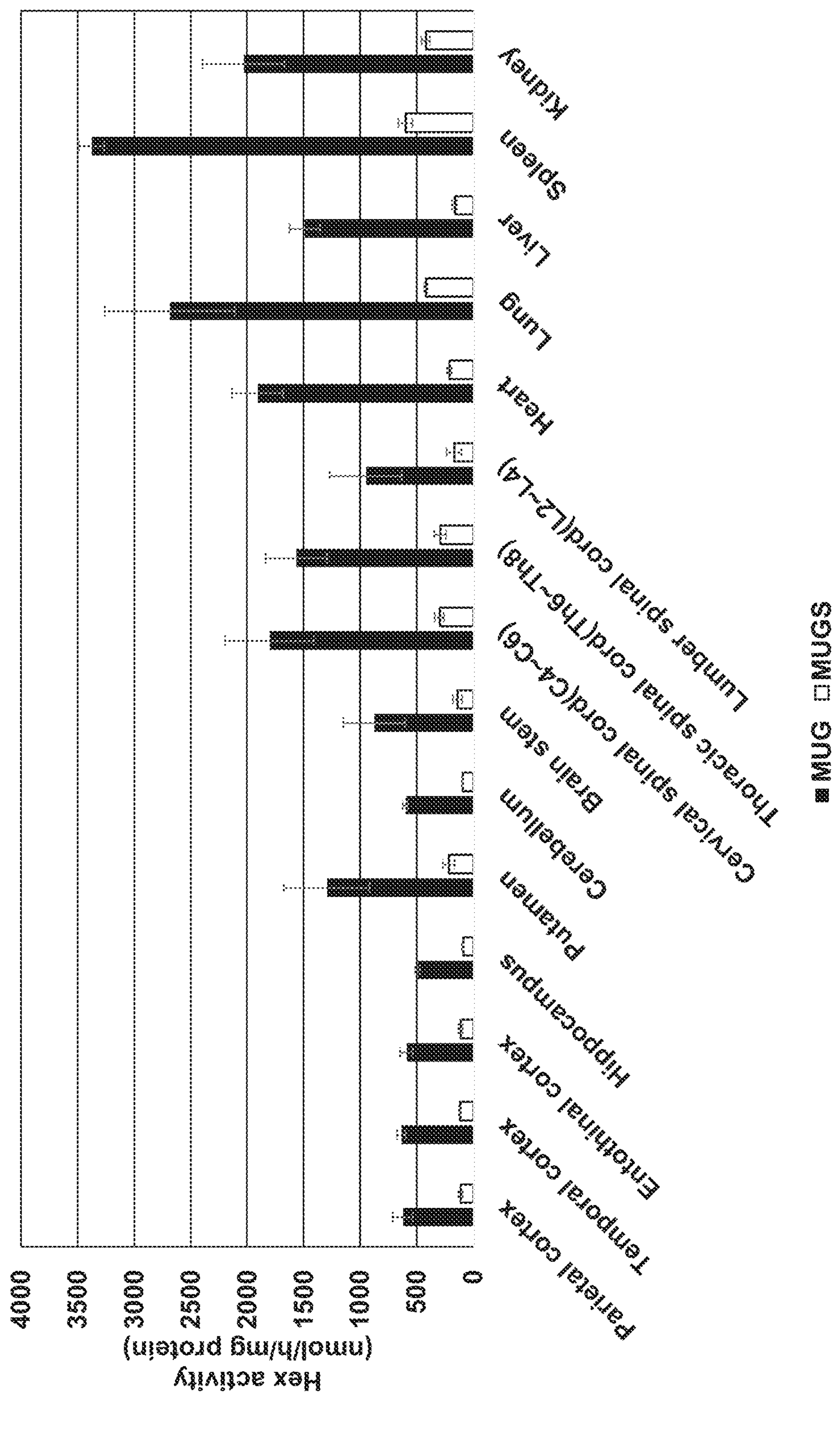
FIG. 25 shows activity of the tissue extracts for degrading MUG (4-methylumbelliferyl β-D-glucosaminide) and MUGS (4-methylumbelliferyl 6-sulfo-β-D-glucosaminide) 3 months after administration of AAV-CMV-modHEXB to crab-eating macaques performed in Example 6.

The results are shown in FIG. 25. Among the tissues of the central nervous system, Hex activity distribution was observed at relatively high levels in the putamen, the brain stem, the cervical spinal cord (C4-C6), the thoracic spinal cord (Th6-Th8), and the lumber spinal cord (L2-L4).

(Assay of Plasma Hex Activity)

Blood samples were obtained before AAV-CMV-modHEXB administration and 12 weeks after administration (immediately before euthanasia) to prepare plasma samples.

The blood plasma diluted to 10-fold with ultrapure water (15 µl) and 15 µl of the MUGS solution were incubated at 37° C. for 30 minutes, 370 µl of 0.2 M glycine-NaOH (pH 10.7) was added to terminate the reaction, the solution was fractionated at 200 µl/well to a 96-well plate, and fluorescent assay (excitation: 355 nm; detection: 460 nm) was performed. In order to prepare a calibration curve, 4-MU (4-methylumbelliferone) diluted to 0.5 nmol to 5 nmol in 0.2 M glycine-NaOH (pH 10.7) was also fractionated at 200 µl/well to a 96-well plate, and fluorescent assay was performed.

Figure 26:
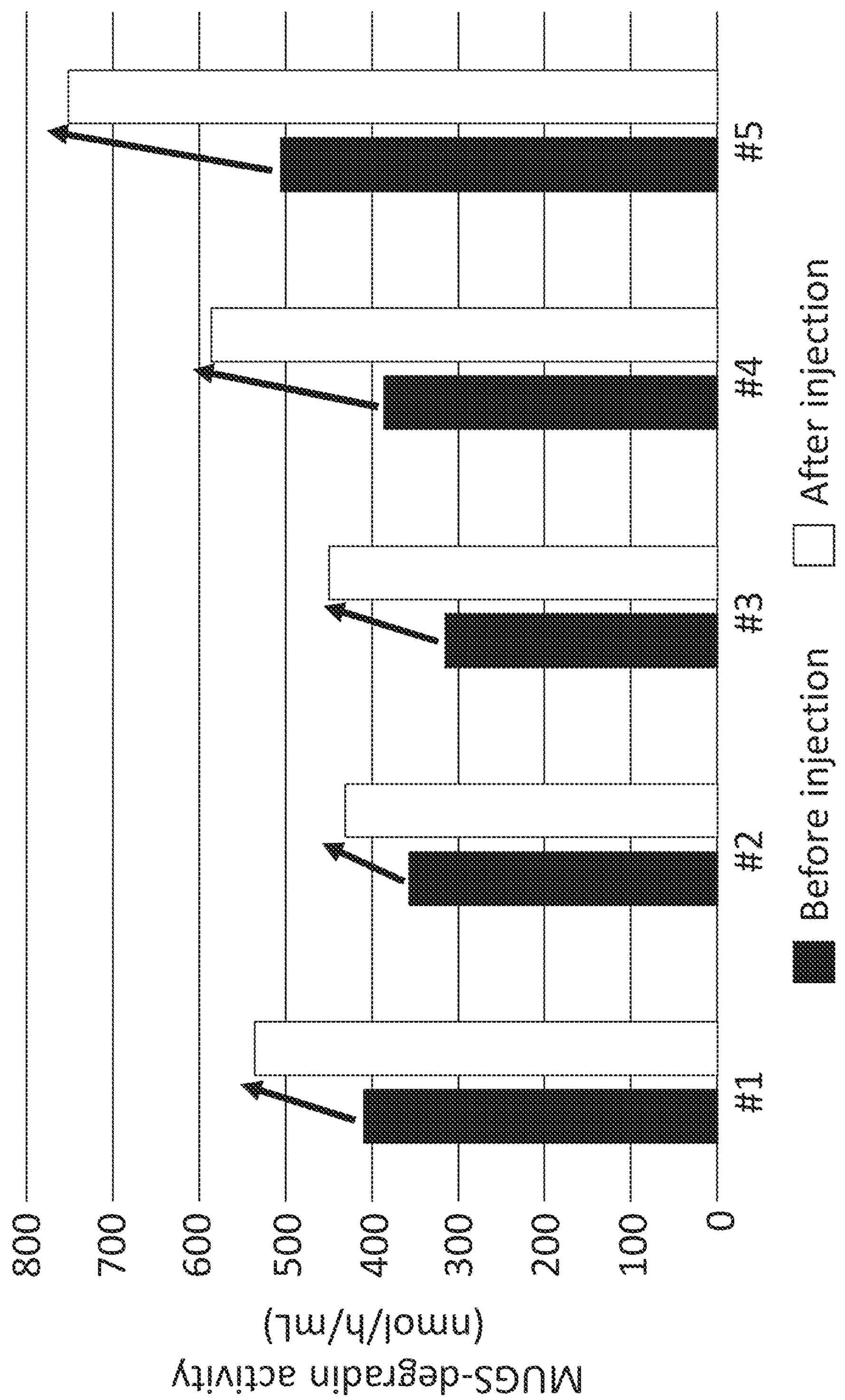
FIG. 26 shows activity of the blood plasma for degrading MUGS (4-methylumbelliferyl 6-sulfo-β-D-glucosaminide) before and 12 weeks after administration of AAV-CMV-modHEXB to crab-eating macaques performed in Example 6.

FIG. 26 shows the results of MUGS-degrading activity assay of the plasma samples of Individuals #1 to #5 before AAV-CMV-modHEXB administration and 12 weeks after administration (immediately before euthanasia). As a result of administration of AAV-CMV-modHEXB to a primate species, the crab-eating macaque, the blood Hex activity level was found to have elevated.

Example 7: Administration of AAV-CMV-GFP to Crab-Eating Macaque

AAV-CMV-GFP prepared in the manner described in Example 5 was administered once intraspinally to two 2-week-old healthy crab-eating macaques (*Macaca fascicularis*) at $2.0\times10^{12}$ vg per kg of body weight. These individuals were observed for 3 months after administration, and no adverse effects were observed in terms of appetite, body weight, and behavior.

(Preparation of Tissue Extract)

Tissues indicated below were extracted 3 months after administration.

Parietal cortex
Temporal cortex
Entothinal cortex
Hippocampus
Putamen
Cerebellum
Brain stem
Spinal cord (C4-C6)

Spinal cord (Th6-Th8)

Spinal cord (L2-L4)

RIPA buffer (300 μl, 50 mM Tris-HCl (pH ya 7.5), 150 mM NaCl, 0.5% sodium deoxycholate, 0.1% SDS, 1% NP-40) was added based on 100 mg each of wet tissue, and ultrasonic disintegration treatment involving the use of an ultrasonic disintegrator for 2 minutes was repeated 10 times to obtain a cell debris solution.

Subsequently, the cell debris solution was ultrasonically treated using an ultrasonic washing apparatus (water bath) for 10 minutes.

The resulting cell debris solution was centrifuged at 4° C. and 12,000×g for 15 minutes, and the supernatant was collected as a GFP detection sample (tissue extract) via Western blotting.

(Detection of GFP in Tissue Extract Via Western Blotting)

The tissue extracts were each adjusted to contain 30 μg of the protein, and ultrapure water 6× dye(+) were added to bring the total amount of the solution to 18 μl.

The samples with the modified volume were boiled for 3 minutes, the total amount of the solutions were applied to 15% SDS-PAGE gel, and electrophoresis was performed at 15 mA to 20 mA.

After electrophoresis, the gel was transcribed to a PVDF membrane at a constant voltage of 15 V for 1 hour.

After transcription, the PVDF membrane was treated with a blocking agent comprising Blocking One and TBS (Tris-buffered saline) at 1:1 for 1 hour.

A primary anti-GFP antibody, 1,000-fold diluted mouse-derived Anti-GFP Clontech jl-8 (Clontech), was subjected to incubation with the blocked PVDF membrane at 4° C. overnight.

Following the treatment with the primary antibody, the PVDF membrane was washed with TBS/0.1% Tween 20 for 5 minutes, and this washing process was performed 3 times.

The washed PVDF membrane was subjected to incubation with the secondary antibodies, the HRP-labeled anti-mouse Ig antibody (Anti-Mouse Ig HRP-linked lot: 32, 1,000-fold diluted) and the HRP-labeled anti-biotin antibody (Anti-Biotin HRP-linked lot: 32, 1,000-fold diluted, for detection of the molecular weight marker), for 1 hour.

Following the treatment with the secondary antibodies, the PVDF membrane was washed with TBS/0.1% Tween 20 for 5 minutes, and this washing process was performed 3 times.

The band intensity was detected using the BIORAD ChemiDoc XRS system.

Figure 27:
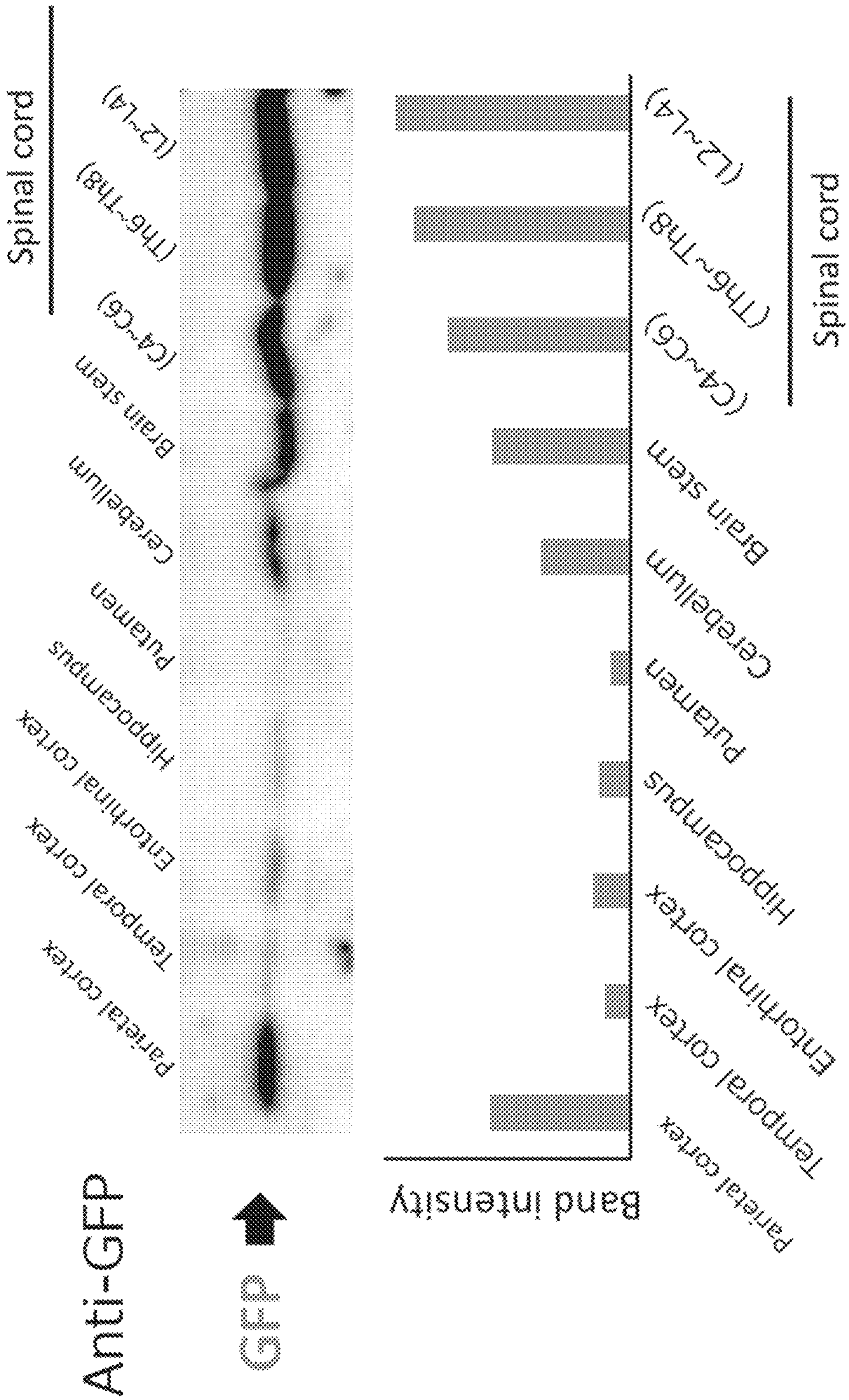
FIG. 27 shows the results of GFP assays via Western blotting of the tissue extracts 3 months after administration of AAV-CMV-GFP to crab-eating macaques performed in Example 7.

The results are shown in FIG. 27. Through administration of AAV-CMV-GFP to a primate species, the crab-eating macaque, the GFP gene was introduced into tissues in the central nervous system. [Sequence Listing Free Text]

SEQ ID NO: 1: the nucleotide sequence of the wild-type AAV1-derived capsid protein AAV1-VP1 (GenBank: NC_002077.1)

SEQ ID NO: 2: the amino acid sequence of the wild-type AAV1-derived capsid protein AAV1-VP1 (GenBank: NC_2077.1)

SEQ ID NO: 3: the nucleotide sequence of the wild-type AAV2-derived capsid protein AAV2-VP1 (GenBank: NC_001401.2)

SEQ ID NO: 4: the amino acid sequence of the wild-type AAV2-derived capsid protein AAV2-VP1 (GenBank: NC_001401.2)

SEQ ID NO: 5: the nucleotide sequence of the wild-type AAV9-derived capsid protein AAV9-VP1 (GenBank: AY530579.1)

SEQ ID NO: 6: the amino acid sequence of the wild-type AAV9-derived capsid protein AAV9-VP1 (GenBank: AY530579.1)

SEQ ID NO: 7: the nucleotide sequence of the AAV1-derived capsid protein mutant AAV1-yfVP1

SEQ ID NO: 8: the amino acid sequence of the AAV1-derived capsid protein mutant AAV1-yfVP1

SEQ ID NO: 9: the nucleotide sequence of the AAV2-derived capsid protein mutant AAV2-yfVP1

SEQ ID NO: 10: the amino acid sequence of the AAV2-derived capsid protein mutant AAV2-yfVP1

SEQ ID NO: 11: the nucleotide sequence of the AAV9-derived capsid protein mutant AAV9-yfVP1

SEQ ID NO: 12: the amino acid sequence of the AAV9-derived capsid protein mutant AAV9-yfVP1

SEQ ID NO: 13: the nucleotide sequence of AAV3-derived 5' ITR (GenBank: NC_001729-derived)

SEQ ID NO: 14: the nucleotide sequence of AAV3-derived 3' ITR

SEQ ID NO: 15: the nucleotide sequence of the AAV2-derived rep gene

SEQ ID NO: 16: the amino acid sequence of the AAV2-derived protein

SEQ ID NO: 17: the nucleotide sequence of the mutagenesis primer 1 (yfAAV1-F)

SEQ ID NO: 18: the nucleotide sequence of the mutagenesis primer 2 (yfAAV1-R)

SEQ ID NO: 19: the nucleotide sequence of the mutagenesis primer 3 (yfAAV2-F)

SEQ ID NO: 20: the nucleotide sequence of the mutagenesis primer 4 (yfAAV2-R)

SEQ ID NO: 21: the nucleotide sequence of the mutagenesis primer 5 (yfAAV9-F)

SEQ ID NO: 22: the nucleotide sequence of the mutagenesis primer 6 (yfAAV9-R)

SEQ ID NO: 23: the Synapsin I promoter sequence (GenBank: M55300.1)

SEQ ID NO: 24: the myelin basic protein promoter sequence (GenBank: M63599 (human)-derived)

SEQ ID NO: 25: the amino acid sequence of modHEXB

SEQ ID NO: 26: the nucleotide sequence of the CMV-modHEXB expression cassette

SEQ ID NO: 27: the nucleotide sequence of the wild-type human β-hexosaminidase β-subunit SEQ ID NO: 28: the amino acid sequence of the wild-type human β-hexosaminidase β-subunit SEQ ID NO: 29: the amino acid sequence, GSEPSGT All publications, patents, and patent applications cited herein are incorporated herein by reference in their entirety.

The invention claimed is:

1. A recombinant adeno-associated virus (AAV) virion comprising:

(1) a capsomere comprising a protein capable of forming an AAV virion, wherein the protein comprises:

a) the amino acid sequence of SEQ ID NO: 12; or b) an amino acid sequence derived from the amino acid sequence of SEQ ID NO: 12 by deletion, substitution, insertion, and/or addition of 1 to 5 amino acids other than the amino acids 444 to 446 of SEQ ID NO: 12; and (2) a polynucleotide packaged in the capsomere, wherein the polynucleotide comprises a systemic promoter sequence operably linked to a nucleotide sequence, wherein the nucleotide sequence encodes:

(A) a first amino acid sequence, wherein the sequence encodes a signal peptide; and (B) a second amino acid sequence derived from the β-subunit of human β-hexosaminidase (HEXB), wherein the HEXB-derived sequence comprises:

(a) amino acids corresponding to amino acids 55 to 556 of SEQ ID NO: 28; and (b) a substitution of the amino acids corresponding to amino acids 312 to 318 of SEQ ID NO: 28 with GSEPSGT (SEQ ID NO: 29), wherein the signal peptide is linked to the N terminus of the HEXB-derived sequence.

2. The AAV virion according to claim 1, wherein the first amino acid sequence comprises a substitution of at least one of the amino acid 452 with asparagine and the amino acid 453 with arginine in the amino acid sequence comprising amino acids 55 to 556 of SEQ ID NO: 28.

3. The AAV virion according to claim 2, wherein the first amino acid sequence comprises any of the amino acid sequences selected from (A) to (C):

(A) the amino acid sequence comprising amino acids 31 to 532 of SEQ ID NO: 25;

(B) an amino acid sequence derived from the amino acid sequence comprising amino acids 31 to 532 of SEQ ID NO: 25 by deletion, substitution, or addition of 1 to several amino acids other than the amino acids at the sites of substitution, wherein a protein comprising the amino acid sequence has an activity derived from the wild-type human β-hexosaminidase α-subunit and protease resistance; and (C) an amino acid sequence having at least 90% sequence identity to the amino acid sequence comprising amino acids 31 to 532 of SEQ ID NO: 25, wherein a protein comprising the amino acid sequence has an activity derived from the wild-type human β-hexosaminidase α-subunit and protease resistance, provided that the amino acids at the site of substitution are identical to those in the amino acid sequence of SEQ ID NO: 25.

4. The AAV virion according to claim 1, wherein the second amino acid sequence is:

the amino acid sequence composed of amino acids 1 to 30 of SEQ ID NO: 25, or the amino acid sequence composed of amino acids 1 to 54 of SEQ ID NO: 28.

5. The AAV virion according to claim 1, wherein the 5' terminus and the 3' terminus of the polynucleotide comprise the 5' terminal inverted terminal repeat (ITR) sequence and the 3' terminal inverted terminal repeat (ITR) sequence derived from AAV1, AAV2, AAV3, or AAV4.

6. The AAV virion according to claim 1, wherein the 5' terminus and the 3' terminus of the polynucleotide comprise the nucleotide sequence of SEQ ID NO: 13 and the nucleotide sequence of SEQ ID NO: 14, respectively.

7. The AAV virion according to claim 1, wherein the promoter sequence is a systemic promoter or neural cell-specific promoter sequence.

8. The AAV virion according to claim 7, wherein the promoter sequence is a sequence of a systemic promoter selected from the group consisting of cytomegalovirus (CMV) promoter, EF-1α promoter, SV40 promoter, and CAG promoter.

9. A method for treatment of Tay-Sachs disease and/or Sandhoff disease comprising administering the AAV virion according to claim 1 to a patient in need of the treatment of Tay-Sachs disease and/or Sandhoff disease.

* * * * *

UNITED STATES PATENT AND TRADEMARK OFFICE

CERTIFICATE OF CORRECTION

PATENT NO. : 12,064,460 B2
APPLICATION NO. : 16/964142
DATED : August 20, 2024
INVENTOR(S) : Kohji Itoh et al.

It is certified that error appears in the above-identified patent and that said Letters Patent is hereby corrected as shown below:

On the Title Page

In the title, Item (54) and in the Specification, Column 1, Lines 1-3, please delete "ADENO-ASSOCIATED VIRUS VIRION FOR TREATMENT OF TAY-SACHS DISEASE AND SANDHOFF DISEASE" and replace with --NOVEL ADENO-ASSOCIATED VIRUS VIRION FOR TREATMENT OF TAY-SACHS DISEASE AND SANDHOFF DISEASE--

Signed and Sealed this
Fifteenth Day of October, 2024

Katherine Kelly Vidal

Katherine Kelly Vidal
*Director of the United States Patent and Trademark Office*